US010059694B2

(12) United States Patent
Ding et al.

(10) Patent No.: US 10,059,694 B2
(45) Date of Patent: Aug. 28, 2018

(54) 2-AMINOPYRIMIDINE COMPOUND AND PHARMACEUTICAL COMPOSITION AND USE THEREOF

(71) Applicants: Shanghai Institute of Materia Medica, Chinese Academy of Sciences, Shanghai (CN); GUANGZHOU INSTITUTES OF BIOMEDICINE AND HEALTH, CHINESE ACADEMY OF SCIENCES, Guangzhou (CN)

(72) Inventors: Ke Ding, Guangzhou (CN); Jian Ding, Shanghai (CN); Shingpan Chan, Guangzhou (CN); Meiyu Geng, Shanghai (CN); Xiaomei Ren, Guangzhou (CN); Hua Xie, Shanghai (CN); Zhengchao Tu, Guangzhou (CN); Yi Chen, Shanghai (CN)

(73) Assignees: Shanghai Institute of Materia Medica, Chinese Academy of Sciences, Shanghai (CN); GUANGZHOU INSTITUTES OF BIOMEDICINE AND HEALTH, CHINESE ACADEMY OF SCIENCES, Guangzhou (CN)

( * ) Notice: Subject to any disclaimer, the term of this patent is extended or adjusted under 35 U.S.C. 154(b) by 0 days.

(21) Appl. No.: 15/529,333

(22) PCT Filed: Nov. 18, 2015

(86) PCT No.: PCT/CN2015/094954
§ 371 (c)(1),
(2) Date: May 24, 2017

(87) PCT Pub. No.: WO2016/082713
PCT Pub. Date: Jun. 2, 2016

(65) Prior Publication Data
US 2017/0283398 A1    Oct. 5, 2017

(30) Foreign Application Priority Data

Nov. 24, 2014  (CN) .......................... 2014 1 0682756

(51) Int. Cl.
*C07D 239/48* (2006.01)
*C07D 401/12* (2006.01)
(Continued)

(52) U.S. Cl.
CPC ........ *C07D 403/12* (2013.01); *A61K 31/4523* (2013.01); *A61K 31/505* (2013.01);
(Continued)

(58) Field of Classification Search
CPC .. C07D 239/48; C07D 401/10; C07D 401/14; C07D 403/10; C07D 403/14;
(Continued)

(56) References Cited

U.S. PATENT DOCUMENTS 8,338,439 B2    12/2012   Singh et al.
8,450,335 B2     5/2013   Singh et al.
(Continued)

FOREIGN PATENT DOCUMENTS

CN    102083800 A    6/2011
CN    102740847 A   10/2012
(Continued)

OTHER PUBLICATIONS

Remon et al. Cancer Treatment Reviews 40 (2014) 723-729.*
(Continued)

*Primary Examiner* — Venkataraman Balasubramanian
(74) *Attorney, Agent, or Firm* — Wolf, Greenfield & Sacks, P.C.

(57) ABSTRACT

Disclosed are a 2-aminopyrimidine compound and pharmaceutical composition and use thereof. The structure of the 2-aminopyrimidine compound is as represented by formula I, in the formula, $R_1$, $R_2$, $R_3$, $R_4$, $R_5$, X, Y, Z, W, (i) being as defined in the specification and the claims. Such compounds effectively inhibit the growth of a variety of tumor cells and have inhibitory effects on EGFR and IGF1R protease, and can be used for preparing antineoplastic drugs and overcome the tolerance induced by the existing drugs such as gefitinib, erlotinib and the like. The compound has selectivity for tumors, in particular the wild-type non-small cell lung cancer and have good pharmacokinetic characteristics.

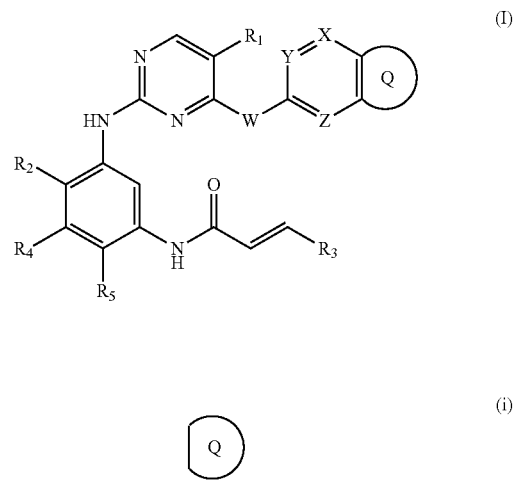

15 Claims, 2 Drawing Sheets

(51) Int. Cl.
*C07D 403/12* (2006.01)
*A61K 31/505* (2006.01)
*A61K 31/506* (2006.01)
*A61K 31/53* (2006.01)
*A61K 31/5377* (2006.01)
*A61K 31/4523* (2006.01)
*A61P 35/00* (2006.01)
*A61K 31/551* (2006.01)

(52) U.S. Cl.
CPC ............ *A61K 31/506* (2013.01); *A61K 31/53* (2013.01); *A61K 31/551* (2013.01); *C07D 239/48* (2013.01); *C07D 401/12* (2013.01)

(58) Field of Classification Search
CPC .. C07D 413/10; C07D 413/14; A61K 31/506; A61K 31/4523; A61K 31/5377; A61K 31/53; A61K 31/551
USPC ....... 544/114, 116, 183, 184, 235, 236, 245, 544/296, 322, 323, 324; 540/553; 514/218, 231.5, 243, 248, 258.1, 275
See application file for complete search history.

(56) References Cited

U.S. PATENT DOCUMENTS

2004/0063705 A1  4/2004  Harmange et al.
2014/0323464 A1  10/2014 Taunton, Jr. et al.

FOREIGN PATENT DOCUMENTS

| CN | 103717602 A | 4/2014 |
| WO | WO 2007/035309 A1 | 3/2007 |
| WO | WO 2008/128231 A1 | 10/2008 |
| WO | WO 2009/158571 A1 | 12/2009 |
| WO | WO 2013/169401 A1 | 11/2013 |

OTHER PUBLICATIONS

Juchu et al. Drug Resistance Updates 20 (2015) 12-28.*
Tan et al. Lung Cancer 93 (2016) 59-68.*
Cecil Textbook of Medicine, edited by Bennet, J.C., and Plum F., 20th edition, vol. 1, 1004-1010, 1996.*
Cohen et al., Current Opinion in Chemical Biology, 3,459-465, 1999.*
Dermer et al., Bio/Technology, 1994, 12:320.*
Freshney et al., Culture of Animal Cells, A Manual of Basic Technique, Alan R. Liss, Inc., 1983, New York, p. 4.*
Golub et al., Science, 286, 531-537, 1999.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
PCT/CN2015/094954, Feb. 4, 2016, International Search Reports and Written Opinion.
PCT/CN2015/094954, Jun. 8, 2017, International Preliminary Report on Patentability.
EP 15863532.6, Apr. 24, 2018, Extended European Search Report.
EP 15863532.6, May 14, 2018, Supplementary European Search Report.

* cited by examiner

2-AMINOPYRIMIDINE COMPOUND AND PHARMACEUTICAL COMPOSITION AND USE THEREOF

CROSS-REFERENCE TO RELATED APPLICATIONS

This application is a national stage filing under 35 U.S.C. § 371 of international application PCT/CN2015/094954, filed Nov. 18, 2015, which claims priority to Chinese Application No. 201410682756.9, filed Nov. 24, 2014, the disclosures of each of which are incorporated by reference here in in their entirety.

FIELD OF INVENTION

The present invention belongs to field of chemical pharmaceutical, especially relates to the 2-aminopyrimidine compound, pharmaceutical composition, and use thereof.

BACKGROUND OF THE INVENTION

Tumor molecular targeted therapy is a treatment method based on the key molecules closely related to the tumor growth through chemical or biological means so as to selectively kill tumor cells. Targeted therapy is characterized by high specificity, strong selectivity and mild side effects; when used in combination, it can enhance the efficacy of traditional chemotherapy, radiotherapy, and reduce postoperative recurrence. Tumor targeted therapy is a hotspot and trend of tumor therapy.

Protein tyrosine kinases (PTKs) are a class of protein enzymes that catalyzes the phosphorylation of phenolic hydroxyl groups on tyrosine residues of various important proteins, thereby activating the function of functional proteins. Studies have shown that more than half of proto-oncogenes and oncogenes are associated with protein tyrosine kinases. The research of anti-tumor drugs with tyrosine kinases as a target becomes a hotspot in the world, and is also the focus of the research of pharmaceutical development institutions.

Epidermal growth factor receptor (EGFR), a receptor tyrosine protein kinases, regulates cell proliferation, survival, adhesion, migration and differentiation. EGFR is over activated or constitutively activated in various tumor cells, such as lung cancer, breast cancer, prostate cancer and so on. Blocking the activation of EGFR and Erb-B2 is clinically confirmed as a dominant approach to targeted therapy of tumor cells. Two small molecule inhibitors targeting EGFR, gefitinib and erlotinib, have been get a quick approval of US FDA for the treatment of patients with advanced non-small cell lung cancer (NSCLC) who have lost response to conventional chemotherapy.

Multiple prospective clinical studies have confirmed that EGFR-TKI (EGFR-tyrosine kinases inhibitors) response rate in NSCLC patients with EGFR activated mutation positive is significantly higher than that in NSCLC patients with EGFR wild-type, while progression-free survival (PFS) and overall survival (OS) also significantly prolonged. Nevertheless, PFS of the majority of patients with EGFR mutation positive is no more than 12 to 14 months, that is to say, resistance to TKI has been occurred in them. The mechanism of acquired resistance and its clinical coping strategies is another hotspot in the field of targeted therapy.

For drug resistance, the strategy used in clinical practice is: Strategy 1: continue to use EGFR-TKI, cross-use gefitinib and erlotinib. In short, continue using TKI after the TKI progress is of some, but very limited benefits. Strategy 2: Developing new EGFR-TKI. Strategy 3: treating for other target sites. As the "alternative pathway" plays an important role in EGFR-TKI resistance, targeted drugs for these pathways are continuously appearing. However, currently the EGFR-TKI is still unable to solve the clinical stress caused by drug resistance, and most of the existing drugs are EGFR reversible or irreversible inhibitor in which the basic nucleus is quinazoline or quinoline amine, and the toxic side effects caused by the poor selectivity for wild-type cells are also unavoidable.

Therefore, there is an urgent need to provide new types of compounds, particularly novel skeletons, to solve problems such as drug resistance, poor selectivity, and poor pharmacological properties.

SUMMARY OF THE INVENTION

The object of the present invention is to provide a novel 2-aminopyrimidine compound and pharmaceutical compositions and use thereof.

In the first aspect of the present invention, a compound of formula I, or a pharmaceutically acceptable salt or stereoisomer thereof or a prodrug thereof is provided,

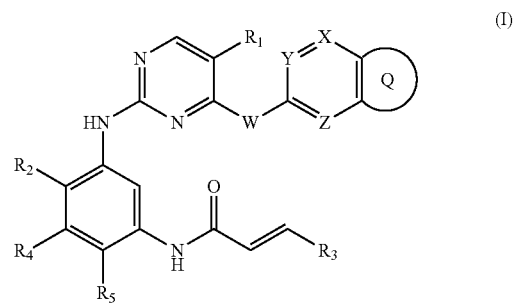

Wherein $R_1$ and $R_2$ are each independently H, halogen, cyano, substituted or unsubstituted $C_1$-$C_6$ alkyl, substituted or unsubstituted $C_3$-$C_6$ cycloalkyl, substituted or unsubstituted $C_1$-$C_6$ alkoxy, and substituted or unsubstituted $C_3$-$C_6$ cycloalkoxy;

$R_3$ is H or —$(CH_2)_m NR_8 R_9$; $R_4$ and $R_5$ are independently H, substituted or unsubstituted $C_1$-$C_6$ alkyl, substituted or unsubstituted $C_1$-$C_6$ alkoxy, halogen, —$(CH_2)_m NR_8 R_9$, and —$(CH_2)_m CR_6 R_8 R_9$; wherein each m is independently 0, 1, 2 or 3; $R_6$ is H or $C_1$-$C_3$ alkyl; each $R_8$ and each $R_9$ are independently selected from H, substituted or unsubstituted $C_1$-$C_6$ alkyl, or $R_8$, $R_9$ and attached N or C together form an unsubstituted or substituted 3-8 membered monocyclic or fused ring containing 1, 2 or 3 heteroatoms selected from O, N, S.

W is NH, N($C_1$-$C_3$ alkyl), O or S;

X, Y, Z are each independently N or —$CR_{10}$, wherein $R_{10}$ is H, halogen, substituted or unsubstituted $C_1$-$C_3$ alkyl, and substituted or unsubstituted $C_1$-$C_3$ alkoxy;

is a substituted or unsubstituted 5 to 7 membered aromatic ring containing 0, 1, 2 or 3 heteroatoms selected from O, N or S;

Wherein each substituted independently means substituted by substituents selected from the group consisting of: halogen, hydroxy, amino, $C_1$-$C_3$ alkyl, $C_1$-$C_3$ alkoxy, —NH($C_1$-$C_3$ alkyl), —N($C_1$-$C_3$ alkyl)($C_1$-$C_3$ alkyl), and —C(=O)($C_1$-$C_3$ alkyl).

In another preferred embodiment, the salt is selected from tinorganic acid salts or organic acid salts such as hydrochloride, sulfate, hydrobromide, phosphate, nitrate, acetate, maleate, p-toluene sulfonate, methanesulfonate or trifluoroacetic acid.

In another preferred embodiment, the substitutions are independently mono-substituted, disubstituted, tri-substituted or tetra-substituted.

In another preferred embodiment, the unsubstituted or substituted 3-8 membered monocyclic or fused ring optionally contains 1, 2 or 3 heteroatoms selected from O, N, S, the substituted means substituted by substituents selected from the group consisting of: halogen, $C_1$-$C_3$ alkyl, —NH($C_1$-$C_3$ alkyl), —N($C_1$-$C_3$ alkyl)($C_1$-$C_3$ alkyl), and —C(=O)($C_1$-$C_3$ alkyl).

In another preferred embodiment, W is NH, O, S or —N(CH$_3$).

In another preferred embodiment, X is N or —CH—.

In another preferred embodiment, Y is —CH—.

In another preferred embodiment, Z is —CH—.

In another preferred embodiment, $R_1$ and $R_2$ are each independently H, halogen, cyano, $C_1$-$C_6$ alkyl, $C_1$-$C_6$ alkoxy, $C_3$-$C_6$ cycloalkyl, $C_3$-$C_6$ cycloalkoxy, $C_1$-$C_6$ haloalkyl or $C_1$-$C_6$ haloalkoxy.

In another preferred embodiment, $R_1$ is H, fluoro, chloro, bromo, cyano, $C_1$-$C_4$ alkyl, $C_1$-$C_3$ fluoroalkyl, $C_1$-$C_3$ fluoroalkoxy or $C_1$-$C_3$ alkoxy.

In another preferred embodiment, the $C_1$-$C_3$ fluoroalkyl is trifluoromethyl group.

In another preferred embodiment,

is phenyl, furanyl, thienyl, pyrrolyl, pyrazolyl, thiazolyl, isothiazolyl, oxazolyl, isoxazolyl, pyrazinyl, pyridazinyl, pyridyl, imidazolyl or pyrimidinyl.

In another preferred embodiment,

is phenyl, pyrrolyl, or pyridyl.

In another preferred embodiment, the compound of formula I have one or more of the following characteristics:

(1) $R_3$ is H, —(CH$_2$)sN($C_1$-$C_3$ alkyl)($C_1$-$C_3$ alkyl), or

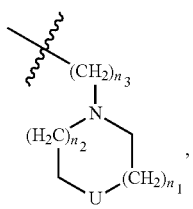

wherein s is 1 or 2 or 3;

(2) $R_4$ is H, $C_1$-$C_3$ alkyl, $C_1$-$C_3$ haloalkyl, $C_1$-$C_3$ alkoxy, $C_1$-$C_3$ haloalkoxy, halogen, —(CH$_2$)$_m$NR$_8$R$_9$, or

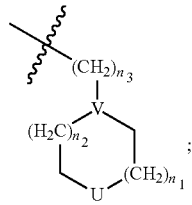

(3) $R_5$ is H, $C_1$-$C_3$ alkyl, $C_1$-$C_3$ haloalkyl, $C_1$-$C_3$ alkoxy, $C_1$-$C_3$ haloalkoxy, halogen, —(CH$_2$)$_m$NR$_8$R$_9$,

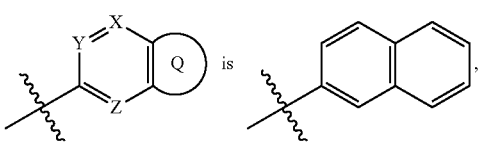

Wherein each m is independently 0, 1, 2 or 3;

Each $R_8$ and each $R_9$ are independently selected from H, substituted or unsubstituted $C_1$-$C_3$ alkyl, the term substituted means substituted by substituents selected from the group consisting of: halogen, —NH($C_1$-$C_3$ alkyl), —N($C_1$-$C_3$ alkyl)($C_1$-$C_3$ alkyl), and —C(=O)($C_1$-$C_3$ alkyl);

Each $n_1$, each $n_2$, and each $n_3$ are independently 0, 1, 2 or 3;

Each V is independently CH, C($C_1$-$C_3$ alkyl) or N;

Each U is independently none, O, S, CR$_{11}$R$_{12}$ or NR$_{13}$, wherein R$_{11}$, R$_{12}$, R$_{13}$ are independently H, $C_1$-$C_3$ alkyl, $C_3$-$C_6$ cycloalkyl, —NH($C_1$-$C_3$ alkyl), —N($C_1$-$C_3$ alkyl)($C_1$-$C_3$ alkyl) or —C(=O)($C_1$-$C_3$ alkyl).

In another preferred embodiment,

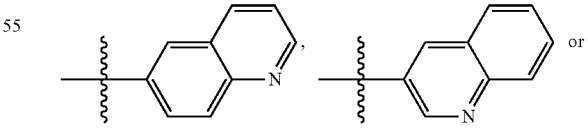

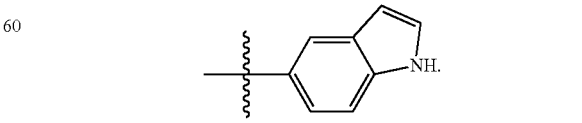

In another preferred embodiment, the compound of formula I has one or more of the following characteristics:

(1) R₃ is H,

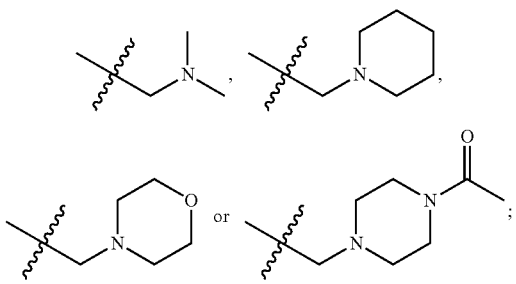

(2) R₄ is H, —CH₃,

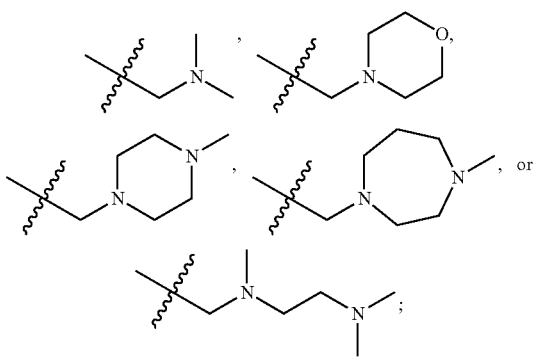

(3) R₅ is H, —CH₃, F,

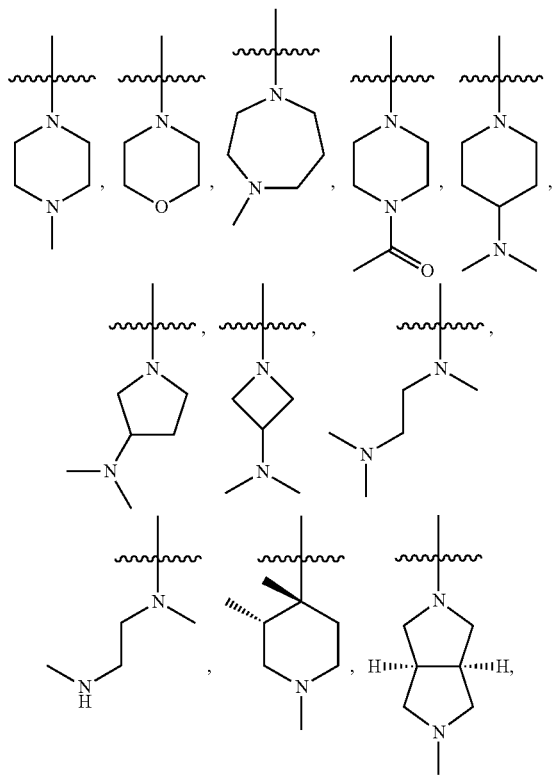

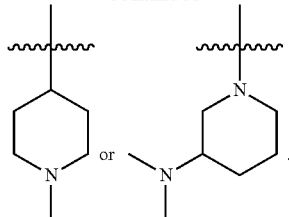

In another preferred embodiment, W is NH; X, Y and Z are CH;

is benzene ring, the structure of the compound of formula I is formula II:

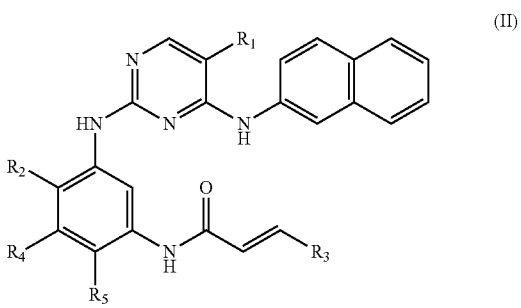

(II)

Wherein R₁, R₂, R₃, R₄ and R₅ are as defined above.

In another preferred embodiment, each substituent in the compound of formula I is a substituent at the corresponding position in each of the specific compounds in the embodiments.

In another preferred embodiment, the compound of formula I is:

(E)-N-((3-((5-chloro-4-((naphthalen-2-yl)amino))pyrimidine-2-yl)amino)-4-methoxyphenyl)-4-(dimethylamino)-2-butenamide;

(E)-N-((3-((5-chloro-4-((quinoline-6-yl)amino))pyrimidine-2-yl)amino)-4-methoxyphenyl)-4-(dimethylamino)-2-butenamide;

(E)-N-((3-((5-chloro-4-((quinoline-3-yl)amino))pyrimidine-2-yl)amino)-4-methoxyphenyl)-4-(dimethylamino)-2-butenamide;

(E)-N-((3-((5-chloro-4-((indole-5-yl)amino))pyrimidine-2-yl)amino)-4-methoxyphenyl)-4-(dimethylamino)-2-butenamide;

(E)-N-((3-((5-chloro-4-(N-methyl-(naphthalen-2-yl)amino))pyrimidine-2-yl)amino)-4-methoxyphenyl)-4-(dimethylamino)-2-butenamide;

(E)-N-((3-((5-chloro-4-((naphthalen-2-yl)oxy))pyrimidine-2-yl)amino)-4-methoxyphenyl)-4-(dimethylamino)-2-butenamide;

(E)-N-((3-((5-chloro-4-((naphthalen-2-yl)thioro))pyrimidine-2-yl)amino)-4-methoxyphenyl)-4-(dimethylamino)-2-butenamide;

(E)-N-((3-(4-((naphthalen-2-yl)amino)pyrimidine-2-yl)amino)-4-methoxyphenyl)-4-(dimethylamino)-2-butenamide;

(E)-N-((3-((5-bromo-4-((naphthalen-2-yl)amino))pyrimidine-2-yl)amino)-4-methoxyphenyl)-4-(dimethylamino)-2-butenamide;
(E)-N-((3-((5-fluoro-4-((naphthalen-2-yl)amino))pyrimidine-2-yl)amino)-4-methoxyphenyl)-4-(dimethylamino)-2-butenamide;
(E)-N-((3-((5-methyl-4-((naphthalen-2-yl)amino))pyrimidine-2-yl)amino)-4-methoxyphenyl)-4-(dimethylamino)-2-butenamide;
(E)-N-((3-((5-methoxy-4-((naphthalen-2-yl)amino))pyrimidine-2-yl)amino)-4-methoxyphenyl)-4-(dimethylamino)-2-butenamide;
(E)-N-((3-((5-cyano-4-((naphthalen-2-yl)amino))pyrimidine-2-yl)amino)-4-methoxyphenyl)-4-(dimethylamino)-2-butenamide;
(E)-N-((3-((5-trifluoromethyl-4-((naphthalen-2-yl)amino))pyrimidine-2-yl)amino)-4-methoxyphenyl)-4-(dimethylamino)-2-butenamide;
(E)-N-((3-((5-isopropyl-4-((naphthalen-2-yl)amino))pyrimidine-2-yl)amino)-4-methoxyphenyl)-4-(dimethylamino)-2-butenamide;
(E)-N-((3-((5-chloro-4-((naphthalen-2-ylamino))pyrimidine-2-yl)amino)phenyl)-4-(dimethylamino)-2-butenamide;
(E)-N-((3-((5-chloro-4-((naphthalen-2-ylamino))pyrimidine-2-yl)amino)-4-methylphenyl)-4-(dimethylamino)-2-butenamide;
(E)-N-((3-((5-chloro-4-((naphthalen-2-ylamino))pyrimidine-2-yl)amino)-4-fluorophenyl)-4-(dimethylamino)-2-butenamide;
(E)-N-((3-((5-chloro-4-((naphthalen-2-ylamino))pyrimidine-2-yl)amino)-4-ethoxyphenyl)-4-(dimethylamino)-2-butenamide;
(E)-N-((3-((5-chloro-4-((naphthalen-2-ylamino))pyrimidine-2-yl)amino)-4-isopropoxyphenyl)-4-(dimethylamino)-2-butenamide;
(E)-N-((3-((5-chloro-4-((naphthalen-2-ylamino))pyrimidine-2-yl)amino)-5-methylphenyl)-4-(dimethylamino)-2-butenamide;
(E)-N-((5-((5-chloro-4-((naphthalen-2-ylamino))pyrimidine-2-yl)amino)-2-methylphenyl)-4-(dimethylamino)-2-butenamide;
(E)-N-((5-((5-chloro-4-((naphthalen-2-ylamino))pyrimidine-2-ylamino)-2-fluoro-4-methoxyphenyl)-4-(dimethylamino)-2-butenamide;
(E)-N-((3-((5-bromo-4-((naphthalen-2-ylamino))pyrimidine-2-yl)amino)phenyl)-4-(dimethylamino)-2-butenamide;
(E)-N-((3-((5-bromo-4-((naphthalen-2-ylamino))pyrimidine-2-yl)amino)-4-methylphenyl)-4-(dimethylamino)-2-butenamide;
(E)-N-((3-((5-bromo-4-((naphthalen-2-ylamino))pyrimidine-2-yl)amino)-4-fluorophenyl)-4-(dimethylamino)-2-butenamide;
(E)-N-((3-((5-bromo-4-((naphthalen-2-ylamino))pyrimidine-2-yl)amino)-4-ethoxyphenyl)-4-(dimethylamino)-2-butenamide;
(E)-N-((3-((5-bromo-4-((naphthalen-2-ylamino))pyrimidine-2-ylamino)-4-isopropoxyphenyl)-4-(dimethylamino)-2-butenamide;
(E)-N-((3-((5-bromo-4-((naphthalen-2-ylamino))pyrimidine-2-yl)amino)-5-methylphenyl)-4-(dimethylamino)-2-butenamide;
(E)-N-((5-((5-bromo-4-((naphthalen-2-yl)amino))pyrimidine-2-yl)amino)-2-methylphenyl)-4-(dimethylamino)-2-butenamide;
(E)-N-((5-((5-bromo-4-((naphthalen-2-yl)amino))pyrimidine-2-yl)amino)-2-fluoro-4-methoxyphenyl)-4-(dimethylamino)-2-butenamide;
N-((3-((5-chloro-4-((naphthalen-2-yl)amino))pyrimidine-2-yl)amino)-4-methoxyphenyl)acrylamide
(E)-N-((3-((5-chloro-4-((naphthalen-2-yl)amino))pyrimidine-2-yl)amino)-4-methoxyphenyl)-4-(piperidine-1-yl)-2-butenamide;
(E)-N-((3-((5-chloro-4-((naphthalen-2-yl)amino))pyrimidine-2-yl)amino)-4-methoxyphenyl)-4-(morpholine-1-yl)-2-butenamide;
(E)-N-((3-((5-chloro-4-((naphthalen-2-yl)amino))pyrimidine-2-yl)amino)-4-methoxyphenyl)-4-(4-acetylpiperazine-1-yl)-2-butenamide;
N-((3-((5-chloro-4-((naphthalen-2-yl)amino))pyrimidine-2-yl)amino)-5-morpholine methylphenyl)acrylamide;
N-((3-((5-chloro-4-((naphthalen-2-yl)amino))pyrimidine-2-yl)amino)-5-(dimethylaminomethyl)phenyl)acrylamide;
N-((3-((5-chloro-4-((naphthalen-2-yl)amino))pyrimidine-2-yl)amino)-5-((N-methyl-N-dimethylaminoethyl)methylamine)phenyl)acrylamide;
N-((3-((5-chloro-4-((naphthalen-2-yl)amino))pyrimidine-2-yl)amino)-5-((4-methylpiperazine-1-yl)methyl)phenyl)acrylamide;
N-((3-((5-chloro-4-((naphthalen-2-yl)amino))pyrimidine-2-yl)amino)-5-((4-methylhomopiperazine-1-yl)methyl)phenyl)acrylamide;
N-((5-((5-chloro-4-((naphthalen-2-yl)amino))pyrimidine-2-yl)amino)-2-((N-methyl-N-dimethylaminoethyl)amino)-4-methoxyphenyl)acrylamide;
N-((5-((5-chloro-4-((naphthalen-2-yl)amino))pyrimidine-2-yl)amino)-2-(4-acetylpiperazine)-4-methoxyphenyl)acrylamide;
N-((5-((5-chloro-4-((naphthalen-2-yl)amino))pyrimidine-2-yl)amino)-2-(4-methylpiperazine)-4-methoxyphenyl)acrylamide;
N-((5-((5-chloro-4-((naphthalen-2-yl)amino))pyrimidine-2-yl)amino)-2-morpholiyl-4-methoxyphenyl)acrylamide;
N-((5-((5-chloro-4-((naphthalen-2-yl)amino))pyrimidine-2-yl)amino)-2-(4-methylhomopiperazinyl)-4-methoxyphenyl)acrylamide;
N-((5-((5-chloro-4-((naphthalen-2-yl)amino))pyrimidine-2-yl)amino)-2-(4-dimethylaminopiperidine)-4-methoxyphenyl)acrylamide;
N-((5-((5-chloro-4-((naphthalen-2-yl)amino))pyrimidine-2-yl)amino)-2-(3-dimethylaminopyrrolidine-1-yl)-4-methoxyphenyl)acrylamide;
N-((5-((5-chloro-4-((naphthalen-2-yl)amino))pyrimidine-2-yl)amino)-2-(3-dimethylaminoazetidine-1-yl)-4-methoxyphenyl)acrylamide; or
N-((5-((5-chloro-4-(naphthalen-2-ylamino)pyrimidine-2-yl)amino)-4-methoxy-2-(methyl(2-methylamino)ethyl)amino)phenyl)acrylamide.

In the second aspect of the present invention, a preparation method of a compound of formula I of the first aspect of the present invention is provided, a compound of formula III or a salt thereof is used to react with a compound of formula A or a salt thereof, or with a compound of formula or a salt thereof so as to obtain a compound of formula I,

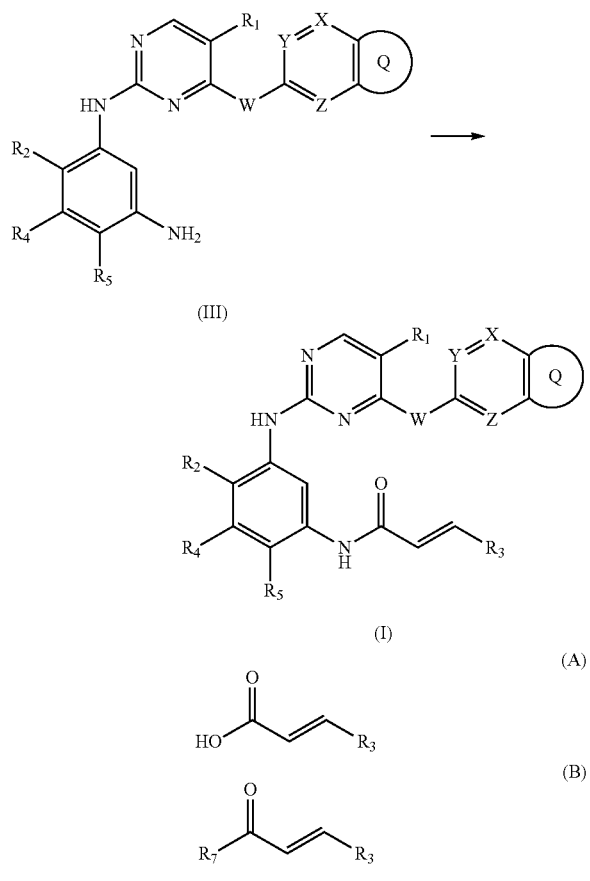

(III)

(I)

(A)

(B)

Wherein $R_1$, $R_2$, $R_3$, $R_4$, $R_5$, W, X, Y and Z and

are as defined above;

R7 is halogen, —$OCOR_{14}$ or $OR_{14}$, $R_{14}$ is $C_1$-$C_6$ alkyl, $C_1$-$C_6$ haloalkyl, C6-C10 aryl or C6-C10 aryl $C_1$-$C_6$ alkyl, preferably $C_1$-$C_3$ alkyl, $C_1$-$C_3$ haloalkyl, phenyl or phenyl $C_1$-$C_3$ alkyl.

In the third aspect of the present invention, a pharmaceutical composition is provided, wherein comprises:

The compound of formula I, the pharmaceutically acceptable salt or stereoisomer thereof, or the prodrug thereof of the first aspect of the present invention; and a pharmaceutically acceptable carrier.

In the fourth aspect of the present invention, the use of the compound of formula I, the pharmaceutically acceptable salt or stereoisomer thereof, or the prodrug thereof of the first aspect of the present invention, or the pharmaceutical composition of the third aspect of the present invention is provided, wherein used in the:

(1) preparation of medicine for treatment of tumor;
(2) preparation of EGFR protease inhibitor medicine;
(3) preparation of IGF1R protease inhibitor medicine.

In another preferred embodiment, the tumor is selected from the group consisting of: non-small cell lung cancer, small cell lung cancer, lung adenocarcinoma, lung squamous cell carcinoma, pancreatic cancer, breast cancer, prostate cancer, liver cancer, skin cancer, epithelial cell carcinoma, gastrointestinal stromal tumor, leukemia, histiocytic lymphoma, nasopharyngeal carcinoma, head and neck cancer, colon cancer, rectal cancer, glioma.

In the fifth aspect of the present invention, a method for the treatment of tumor is provided, wherein comprising administering the compound of formula I, the pharmaceutically acceptable salt or stereoisomer thereof, or the prodrug thereof of the first aspect of the present invention, or the pharmaceutical composition of the third aspect of the present invention to a subject in need.

In the sixth aspect of the present invention, a method of inhibiting EGFR proteases is provided, comprising administering the compound of formula I, the pharmaceutically acceptable salt or stereoisomer thereof, or the prodrug thereof of the first aspect of the present invention, or the pharmaceutical composition of the third aspect of the present invention to a subject in need.

In the seventh aspect of the present invention, a method of inhibiting IGF1R proteases is provided, comprising administering the compound of formula I, the pharmaceutically acceptable salt or stereoisomer thereof or the prodrug thereof of the first aspect of the present invention, or the pharmaceutical composition of the third aspect of the present invention to a subject in need. In another preferred embodiment, the subject in need is nonhuman mammal or human, preferably a human, mouse or rat.

In the eighth aspect of the present invention, a compound of formula III or a salt thereof is provided:

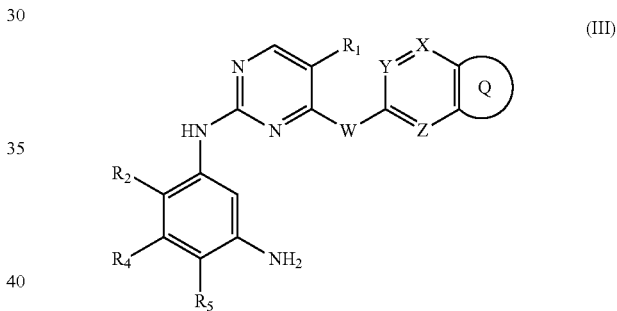

(III)

Wherein $R_1$, $R_2$, $R_4$, $R_5$,

W, X, Y and Z are defined as above, with the proviso that the compound of formula III does not include the following structure:

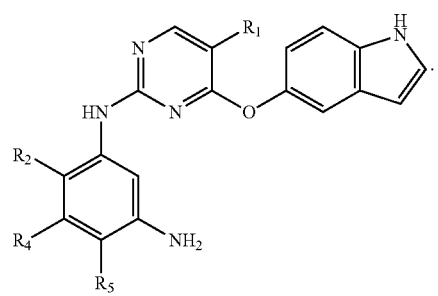

In another preferred embodiment, the salt is selected from the group consisting of inorganic acid salts or organic acid salts, such as hydrochloride, sulfate, hydrobromide, phosphate, nitrate, acetate, maleate, p-toluene sulfonate, methanesulfonate or trifluoroacetic acid.

In a preferred embodiment,

is phenyl, pyrrolyl or pyridyl. In a preferred embodiment,

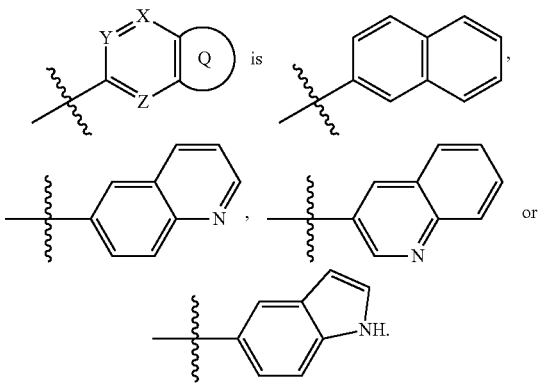

The compounds of formula I and pharmaceutically acceptable salts thereof of the present invention can inhibit the growth of various tumor cells, inhibit EGFR and Her family proteases, and are particularly capable of selectively acting on EGFR$^{L858R/T790M}$ and EGFR$^{Del\ E745\_A750}$ lung cancer cells, to which the compounds have 30-fold greater selectivity than wild-type cancer cells. The compounds can be used to prepare antitumor drugs, and can overcome the resistance induced by existing drugs like gefitinib, erlotinib, which being a new type of protein kinase inhibitor which can overcome the resistance to existing EGFR tyrosine kinase inhibitor and possess selectivity and good pharmacological properties. As commonly understood by those skilled in the art, the compounds and pharmaceutically acceptable salts thereof of the present invention are useful for the preparation of medicine for the treatment of hyperproliferative diseases such as tumors in humans and other mammals.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Figure 1:
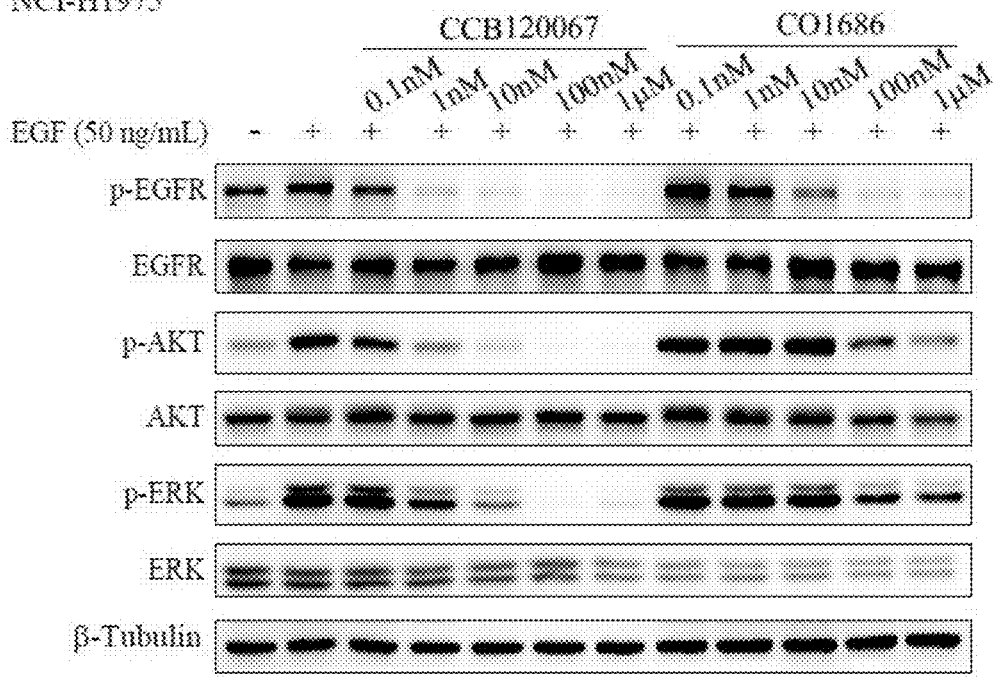
FIG. 1 shows the effect of compound CCB120067 and CO1686 on the phosphorylation of EGFR$^{T790M/L858R}$ kinase and its downstream signaling pathway protein in NCI-H1975 cells containing EGFR$^{T79M/L858R}$ mutations.

Through long-term and intensive studies, the inventors have unexpectedly prepared a novel 2-aminopyrimidine compound which is capable to solve problems such as drug resistance, poor selectivity, poor pharmacological properties. The present invention is completed based on this discovery.

In the compounds of the present invention, when any variable (for example $R_8$, $R_9$) appears more than once in any component, the definition of each occurrence is independent from the other occurrences. Likewise, a combination of substituents and variables is allowed as long as the combination stabilizes the compound. The lines from the substituents into the ring system represent that the referred bond can be attached to any substitutable ring atoms. If the ring system is a polycyclic, it means that the bond is attached to only any suitable carbon atom of the adjacent rings. It should be understood that those skilled in the art can select the substituents and substitution pattern of the compounds of the present invention to provide compounds which are chemically stable and easily synthesizable from readily available materials by techniques in the art and the methods set forth below. If a substituent itself is substituted by more than one group, it should be understood that these groups may be on the same carbon atom or on different carbon atoms as long as the structure is stable. The phrase "substituted with substituents selected from the group" is considered to be equivalent to the phrase "substituted with at least one substituent", and in this case the preferred embodiment will have 1-4 substituents.

As used herein, the term "alkyl" means a branched or linear saturated aliphatic alkyl comprising a specific number of carbon atoms. For example, the definition of "$C_1$-$C_6$" in the "$C_1$-$C_6$ alkyl" includes a group having 1, 2, 3, 4, 5 or 6 carbon atoms in a linear chain or branched chain. For example, "$C_1$-$C_6$ alkyl" specifically includes methyl, ethyl, n-propyl, isopropyl, n-butyl, tert-butyl, isobutyl, pentyl and hexyl. The term "cycloalkyl" refers to a monocyclic saturated aliphatic alkyl having a specific number of carbon atoms. For example, "cycloalkyl" includes cyclopropyl, cyclobutyl, cyclopentyl or cyclohexyl. The term "alkoxy" means a group having an —O-alkyl structure such as —OCH$_3$, —OCH$_2$CH$_3$, —OCH$_2$CH$_2$CH$_3$, —O—CH$_2$CH(CH$_3$)$_2$, —OCH$_2$CH$_2$CH$_2$CH$_3$, —O—CH(CH$_3$)$_2$ and the like. As used herein, the term "5 to 7 membered aromatic ring containing 0, 1, 2 or 3 heteroatoms selected from O, N or S" means a benzene ring or a heteroaromatic ring, and the heteroaromatic ring within the present invention disclosure includes, but is not limited to, imidazolyl, triazolyl, pyrazolyl, furyl, thienyl, oxazolyl, isoxazolyl, pyrazinyl, pyridazinyl, pyridyl, pyrimidinyl, pyrrolyl.

As used herein, "halo" ("halo") or "halogen" as used herein means chlorine, fluorine, bromine and iodine as understood by those skilled in the art.

The present invention provides a compound of formula I, or a pharmaceutically acceptable salt or stereoisomer thereof or a prodrug thereof,

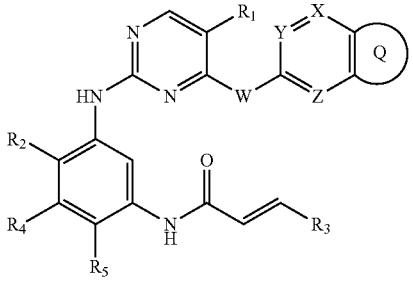

Wherein $R_1$, $R_2$, $R_3$, W, $R_4$, $R_5$, X, Y, Z and

are as defined above.

The present invention includes the free form of compounds of formula I, including pharmaceutically acceptable salts and stereoisomers thereof. Some of the specific exemplary compounds herein are protonated salts of amine compounds. The term "free form" refers to an amine compound in a non-salt form. Included pharmaceutically acceptable salts include not only exemplary salts of specific compounds described herein but also typical pharmaceutically acceptable salts of all forms of compounds of formula I. The free form of the compound specific salt can be isolated using techniques known in the art. For example, the free form can be regenerated by treating the salt with a suitable alkali dilute aqueous solution such as NaOH dilute aqueous solution, dilute aqueous solution of potassium carbonate, dilute aqueous ammonia and dilute aqueous solution of sodium hydrogencarbonate. The free form are somewhat different from the respective salt forms thereof in some physical properties, such as in polar solvents. However, for the purposes of this invention, the acid salts and base salts are comparable to their respective free forms in other pharmaceutical aspects.

The pharmaceutically acceptable salts of the present invention can be synthesized from compounds of the present invention containing a basic or acidic moiety by conventional chemical means. Typically, salts of the basic compound are prepared by ion exchange chromatography or by reaction of free bases and stoichiometric or excessive salt form of inorganic or organic acid in a suitable solvent or combination of several solvents. Similarly, salts of the acidic compounds are formed by reaction with an appropriate inorganic or organic base.

Thus, the pharmaceutically acceptable salts of the compounds of the present invention include conventional non-toxic salts of the compounds of the invention formed by the reaction of a basic compound of the present invention with an inorganic or organic acid. For example, conventional non-toxic salts include salts derived from inorganic acids such as hydrochloric acid, hydrobromic acid, sulfuric acid, sulfamic acid, phosphoric acid, and nitric acid, as well as from organic acids such as acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, p-aminobenzenesulfonic acid, 2-acetoxy-mono-benzoic acid, fumaric acid, toluenesulfonic acid, methanesulfonic acid, ethane disulfonic acid, oxalic acid, isethionic acid, trifluoroacetic acid and the like.

If the compounds of the present invention are acidic, suitable "pharmaceutically acceptable salts" refers to salts prepared by pharmaceutically acceptable non-toxic bases, including inorganic and organic bases. Salts derived from inorganic bases include aluminum salts, ammonium salts, calcium salts, copper salts, iron salts, ferrous salts, lithium salts, magnesium salts, manganese salts, manganaous salts, potassium salts, sodium salts and zinc salts. Particularly preferred are ammonium salts, calcium salts, magnesium salts, potassium salts and sodium salts. Salts derived from pharmaceutically acceptable organic non-toxic bases, the bases include salts of primary amines, secondary amines and tertiary amines, substituted amines including naturally occurring substituted amines, cyclic amines and basic ion exchange resins such as arginine, betaine, caffeine, choline, N, N'-dibenzylethylenediamine, diethylamine, 2-diethylaminoethanol, 2-dimethylaminoethanol, aminoethanol, ethanolamine, ethylenediamine, N-ethylmorpholine, N-ethylpiperidine, glucosamine, glucosamine, histidine, hydroxycobalamin, isopropylamine, lysine, methylglucosamine, morpholine, piperazine, piperidine, piperidine, polyamine resin, procaine, purine, theobromine, triethylamine, trimethylamine, tripropylamine, tromethamine and the like. Berg et al., "Pharmaceutical Salts" J. Pharm. Sci. 1977: 66: 1-19 describes the preparation of pharmaceutically acceptable salts and other typical pharmaceutically acceptable salts described above in more detail.

Since the acidic moiety, such as the carboxyl, which is deprotonated in the compound under physiological conditions, may be anionic and this charge then be counterbalanced by the basic moiety with internal cationic which is protonated or alkylated, such as tetravalent nitrogen atoms. It should be noted that the compounds of the present invention are potential inner salts or zwitterions. In addition to the standard methods known in the literature or exemplified in the experimental procedure, the compounds of the present invention can be prepared by the reactions shown in the following embodiments. Accordingly, the following illustrative embodiments are for purposes of illustration and not limited to the compounds listed or by any particular substituents. The number of substituents shown in the embodiments is not necessarily to be used in the claims. For the sake of clarity, formula I compound having multiple substituents is allowed for the compounds which is shown as being monosubstituted in the below definition.

Compounds of formula I as described in the invention can be prepared by the following reaction procedure:

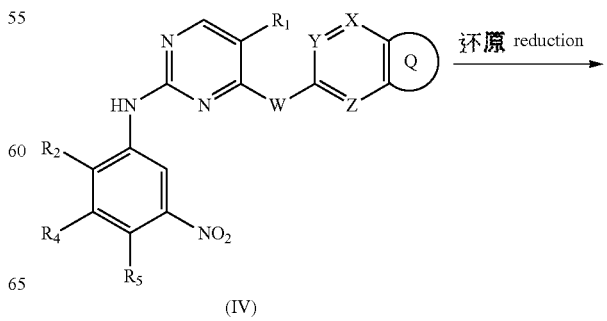

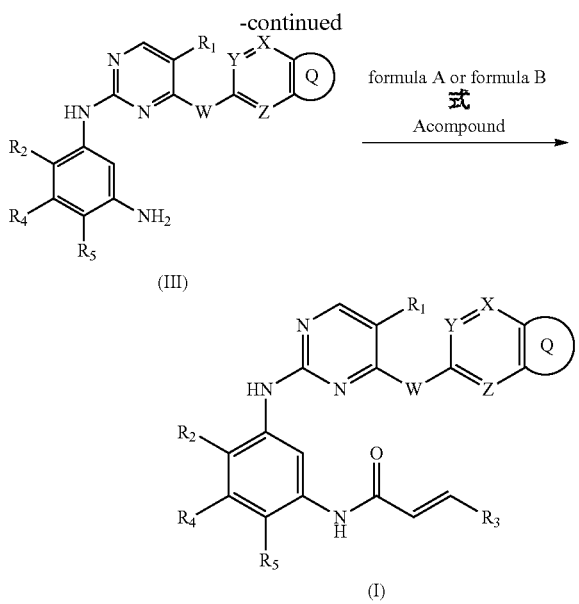

(III)

formula A or formula B
式
A compound (I)

Wherein the compound of formula A and the compound of formula B are as follows:

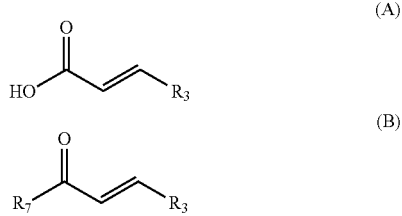

(A)

(B)

Wherein $R_1$, $R_2$, $R_3$, $R_4$, $R_5$, W, X, Y, Z and

are as defined above;
$R_7$ is halogen, —$OCOR_{14}$ or $OR_{14}$, $R_{14}$ is $C_1$-$C_6$ alkyl, $C_1$-$C_6$ haloalkyl, $C_6$-$C_{10}$ aryl or $C_6$-$C_{10}$ aryl $C_1$-$C_6$ alkyl, preferably $C_1$-$C_3$ alkyl, $C_1$-$C_3$ haloalkyl, phenyl or $C_1$-$C_3$ phenylalkyl.
Reduction The compound of formula IV is reduced to give a compound of formula III or a salt thereof. The conditions for the reduction reaction may be: adding a reducing agent such as iron powder, zinc powder or stannous chloride; or in the presence of a hydrogenation catalyst, pumping in hydrogen to carry out the reaction, and the hydrogenation catalyst may be palladium-carbon, active nickel or platinum dioxide. The solvent for the reduction reaction is one or more of acetic acid, hydrochloric acid, sulfuric acid, methanol, ethanol, water, ethyl acetate, acetonitrile and tetrahydrofuran.

The reaction of a compound of formula III or a salt thereof with a compound of formula A or a salt thereof is carried out in a suitable solvent in the presence of a condensing agent and a suitable base, in the presence or absence of a catalyst. The condensing agent is preferably selected from one or more of the group consisting of N,N'-dicyclohexylcarbodiimide (DCC), N-(3-dimethylaminopropyl)-N'-ethylcarbodiimide or its hydrochloride (EDC or EDC.HC1), carbonyldiimidazole (CDI), N,N'-diisopropylcarbodiimide (DIC), O-benzotriazole-N,N,N',N'-tetramethyluronium tetrafluoroborate (TBTU), O-(7-azobenzotriazole)-N,N,N',N'-tetramethyluronium hexafluorophosphate (HATU), Benzotriazole-N,N,N',N'-tetramethyluronium hexafluorophosphate (HBTU), benzotriazol-1-yloxytris(dimethylamino)phosphonium hexafluoride phosphate (BOP) and benzotriazol-1-yloxytripyrrolidinyl hexafluorophosphate (PyBOP); the catalyst is 1-hydroxy-benzotriazole (HOBt) or 4-dimethylaminopyridine (DMAP); the base is preferably selected from one or more of the group consisting of triethylamine, diethylamine, tri-n-butylamine, tripropylamine, diisopropylamine, diisopropylethylamine (DIPEA), trimethylamine, pyridine, 2,6-dimethylpyridine, 4-dimethylaminopyridine, piperidine, pyrrolidine, quinoline, morpholine, N-methylmorpholine (NMM), N-ethylmorpholine, diisopropylamine, diisopropylethylamine, 1,8-diazacyclo[5,4,0]undecene-7 and 1,5-diazabicyclo[4.3.0]-non-5-ene; the reaction solvent is preferably selected from the group consisting of benzene, xylene, toluene, dichloromethane, chloroform, tetrahydrofuran, ether, acetone, 1,4-dioxane, N,N-dimethylformamide, N,N-diethylformamide, N,N-dimethylacetamide, acetonitrile, dimethylsulfoxide or the mixtures thereof, more preferably is tetrahydrofuran, acetonitrile, dichloromethane, N,N-dimethylformamide, N,N-dimethylacetamide, dimethylsulfoxide or the mixtures thereof; the reaction temperature is preferably −20° C. to 200° C., more preferably −10° C. to 100° C.

The reaction of a compound of formula III or a salt thereof with a compound of formula B or a salt thereof is carried out in a suitable solvent in the presence of a base; preferably, the base is selected from one or more of the group consisting of pyridine, piperidine, pyrrolidine, imidazole, morpholine, N-methylmorpholine, quinoline, 4-dimethylaminopyridine, triethylamine, diethylamine, tri-n-butylamine, tripropylamine, diisopropylamine, diisopropylethylamine, sodium methoxide, sodium ethoxide, potassium tert-butoxide, butyllithium, 1,8-diazacyclo[5,4,0]undecene-7, N-methylmorpholine, quinoline, 4-dimethylaminopyridine, sodium hydride, sodium hydroxide, potassium hydroxide, lithium hydroxide, sodium bicarbonate, potassium bicarbonate, sodium carbonate and potassium carbonate; preferably, the solvent of the reaction is selected from the group consisting of aromatic solvent, ether solvent, halogenated hydrocarbon solvent, other solvent or the combinations thereof; preferably, the aromatic solvent is selected from one or more of the group consisting of benzene, toluene, xylene and the like; and the ether solvent is selected from one or more of the group consisting of tetrahydrofuran, ether, ethylene glycol dimethyl ether, diethylene glycol dimethyl ether, ethylene glycol monomethyl ether and dioxane; the halogenated hydrocarbon solvent is selected from one or more of the group consisting of dichloromethane, chloroform, carbon tetrachloride, dichloroethane; the other solvent is selected from one or more of the group consisting of methanol, ethanol, ethylene glycol, n-hexane, cyclohexane, N,N-dimethylformamide, N,N-dimethylacetamide, dimethylsulfoxide, N-methylpyrrolidone, acetone, acetonitrile, ethyl acetate, and water; the temperature of the reaction is preferably −30° C. to 150° C., more preferably −10° C. to 120° C.; the time of the reaction is preferably 10 minutes to 24 hours.

Salts of the compounds of formula III, salts of compounds of formula A and salts of compounds of formula B are selected from inorganic salts or organic acid salts such as hydrochloride, sulfate, hydrobromide, phosphate, nitrate, acetate, maleate, p-toluenesulfonate, methanesulfonate or trifluoroacetic acid.

In one embodiment, the present application provides a method of treating hyperproliferative diseases or condition, such as tumors in human or other mammal by using a compound of formula I or pharmaceutically acceptable salts thereof.

In one embodiment, the compounds and pharmaceutically acceptable salts of the present invention may be used for treating or controlling hyperproliferative diseases such as non-small cell lung cancer, small cell lung cancer, lung adenocarcinoma, lung squamous cell carcinoma, pancreatic cancer, breast cancer, prostate cancer, liver cancer, skin cancer, epithelial cell carcinoma, gastrointestinal stromal tumor, leukemia, histiocytic lymphoma, nasopharyngeal carcinoma, head and neck cancer, colon cancer, rectal cancer, glioma, and the like.

Drug Metabolites and Prodrugs

The metabolites of the compounds and pharmaceutically acceptable salts thereof described herein, as well as prodrugs which can be converted in vivo to the structures of the compounds and pharmaceutically acceptable salts thereof, are also included in the claims of the present application.

Pharmaceutical Composition

The present invention also provides a pharmaceutical composition comprising an active ingredient in a safe and effective amount, and pharmaceutically acceptable carriers.

The term "active ingredient" as used herein refers to a compound of formula I as described herein.

The term "active ingredient" and pharmaceutical compositions described herein can be used as EGFR and IGF1R protease inhibitors. In another preferred embodiment, it can be used for the preparation of a medicine for the prevention and/treatment of tumors.

The term "safe and effective amount" means that the amount of active ingredient is sufficient to significantly improve the condition without causing serious side effects. Generally, the pharmaceutical composition contains 1-2000 mg active ingredient per dose, preferably, 10-200 mg active ingredient per dose. Preferably, the "one dose" is a tablet.

"Pharmaceutically acceptable carrier" means one or more compatible solid or liquid fillers, or gelatinous materials which are suitable for human use and should be of sufficient purity and sufficiently low toxicity.

"Compatibility" refers herein that the components of the composition can be blended with the active ingredients of the present invention and between them without significantly reducing the efficacy of the active ingredient.

Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

In another preferred embodiment, the compounds of formula I of the present invention may form complexes with macromolecular compounds or macromolecules by non-bonded interactions. In another preferred embodiment, the compounds of formula I of the present invention may also be linked to macromolecular compounds or macromolecules by chemical bonds as small molecules. The macromolecular compounds may be biomacromolecules such as high polysaccharides, proteins, nucleic acids, polypeptides, and the like.

There is no special limitation of administration method for the active ingredient or pharmaceutical composition of the present invention, and the representative administration method includes (but is not limited to): oral, intratumoral, rectal, parenteral (intravenous, intramuscular or subcutaneous), and the like.

Solid dosage forms for oral administration include capsules, tablets, pills, powders and granules. In these solid dosage forms, the active ingredient is mixed with at least one conventional inert excipient (or carrier), such as sodium citrate or dicalcium phosphate, or mixed with the following ingredients:

(A) fillers or compatibilizers, for example, starch, lactose, sucrose, glucose, mannitol and silicic acid;
(B) binders such as hydroxymethylcellulose, alginates, gelatin, polyvinylpyrrolidone, sucrose and acacia;
(C) humectants such as glycerol;
(D) disintegrating agents such as agar, calcium carbonate, potato starch or tapioca starch, alginic acid, certain composite silicates, and sodium carbonate;
(E) retarding solvent, such as paraffin;
(F) absorption accelerators, for example, quaternary amine compounds;
(G) wetting agents such as cetyl alcohol and glyceryl monostearate;
(H) adsorbents, for example, kaolin; and
(I) lubricants, for example, talc, calcium stearate, magnesium stearate, solid polyethylene glycol, sodium dodecyl sulfate, or mixtures thereof. In capsules, tablets and pills, the dosage form may also contain buffering agents.

The solid dosage forms described may also be prepared using coatings and shell materials, such as casings and other materials known in the art. They can contain an opaque agent, and the release of the active ingredient in the compositions can be released in a delayed mode in a given portion of the digestive tract. Examples of the embedding components include polymers and waxes. Liquid dosage forms for oral administration include pharmaceutically acceptable emulsions, solutions, suspensions, syrups or tinctures. In addition to the active ingredient, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof. Besides these inert diluents, the composition may also contain additives such as wetting agents, emulsifiers, and suspending agent, sweetener, flavoring agents and perfume.

In addition to the active ingredient, the suspension may contain suspending agent, for example, ethoxylated isooctadecanol, polyoxyethylene sorbitol and sorbitan esters, microcrystalline cellulose, methanol aluminum and agar, or the combinations thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

Compounds of the present invention can be administrated alone, or in combination with other therapeutic agents (such as hypoglycemic agents).

When the pharmaceutical compositions are used, a safe and effective amount of compound of the present invention is applied to a mammal (such as human) in need of, wherein the dose of administration is a pharmaceutically effective dose. For a person weighed 60 kg, the daily dose is usually 1-2000 mg, preferably 20-500 mg. Of course, the particular dose should also depend on various factors, such as the route of administration, patient healthy status, which are well within the skills of an experienced physician.

Combination Therapy

The compounds of formula I may be used in combination with other drugs that are known to treat or ameliorate similar conditions. When administered in combination, the administration and dosage of the original drug remain unchanged while at the same time or subsequently taking the compound of formula I. When the compound of formula I is administered concurrently with one or more of the other drugs, it is preferred to use a pharmaceutical composition containing both one or more known drugs and compounds of formula I. The combination of drugs also involves the administration of a compound of formula I with one or more of the other known drugs in an overlapping period of time. When the compound of formula I is administered in combination with one or more of the other drugs, the doses of the compounds of formula I or known drugs may be lower than those in cases when they are administrated alone.

Drugs or active ingredients that may be administered in combination with a compound of formula I include, but are not limited to:
Estrogen receptor modulators, androgen receptor modulators, retinal-like receptor modulators, cytotoxic/cytostatic agents, antiproliferative agents, protein transferase inhibitors, HMG-CoA reductase inhibitors, HIV protein kinase inhibitors, reverse transcriptase inhibitors, angiogenesis inhibitors, cell proliferation and survival signal inhibitors, drugs that interfere with cell cycle checkpoint and apoptosis inducers, cytotoxic drugs, tyrosine protein inhibitors, EGFR inhibitors, VEGFR inhibitors, serine/threonine protein inhibitors, Bcr-Abl inhibitors, c-Kit inhibitors, Met inhibitors, Raf inhibitors, MEK inhibitors, MMP inhibitors, topoisomerase inhibitors, histidine deacetylase inhibitors, proteasome inhibitors, CDK inhibitors, Bcl-2 family protein inhibitors, MDM2 family protein inhibitors, IAP family protein inhibitors, STAT family protein inhibitors, PI3K inhibitors, AKT inhibitors, integrin blockers, interferon-α, interleukin-12, COX-2 inhibitors, p53, p53 activators, VEGF antibodies, EGF antibodies, and the like.

In one embodiment, drugs or active ingredients that may be administered in combination with a compound of formula I include, but are not limited to: aldesleukin, alendronic acid, interferon, alitretinoin, allopurinol, allopurinol sodium, palonosetron hydrochloride, hexamethylmelamine, aminoglutethimide, amifostine, amrubicin, amsacrine, anastrozole, dolasetron, aranesp, arglabin, arsenic trioxide, aromasin, 5-azacytidine, azathioprine, BCG vaccine or tice BCG vaccine, bestatin, betamethasone acetate, betamethasone sodium phosphate preparations, bexarotene, bleomycin sulfate, broxuridine, bortezomib, busulfan, calcitonin, alemtuzumab injection, capecitabine, carboplatin, casodex, cefesone, celmoleukin, daunorubicin, chlorambucil, cisplatin, cladribine, cladribine, chloroquinophosphate, cyclophosphamide, cytosine arabinoside, dacarbazine, actinomycin D, daunorubicin liposome, dexamethasone, dexamethasone phosphate, estradiol valerate, denileukin diftitox 2, depomedrol, deslorelin, dexrazoxane, diethylstilbestrol, diflucan, docetaxel, deoxifluridine, adriamycin, dronabinol, chin-166-chitosan complex, eligard, rasburicase, epirubicin hydrochloride, aprepitant, epirubicin, epoetin alfa, erythropoietin, eptaplatin, levamisole tablet, estradiol preparations, 17-β-estradiol, estramustine sodium phosphate, ethinyl estradiol, amifostine, hydroxyphosphate, etopophos, etoposide, fadrozole, tamoxifen preparations, filgrastim, finasteride, filgrastim, floxuridine, fluconazole, fludarabine, 5-fluoro-deoxyuridine nucleoside monophosphate, 5-fluorouracil, fluoxymesterone, flutamide, formestane, 1-β-D-arabinofuranosyl thiazolidin-5'-stearoyl phosphate, fotemustine, fulvestrant, gamma globulin, gemcitabine, gemtuzumab, imatinib mesylate, carmustine glutinous rice paper capsules, goserelin, granisetron hydrochloride, histrelin, hycamtin, hydrocortisone, erythro-hydroxy nonyladenine, hydroxyurea, ibritumomab tiuxetan, idarubicin, ifosfamide, interferon α, interferon-α2, interferon α-2A, interferon α-2B, interferon α-n1, interferon α-n3, interferon β, interferon γ-1a, interleukin-2, intron A, iressa, irinotecan, kytril, lentinan sulfate, letrozole, leucovorin, leuprorelin, leuprorelin acetate, 1-tetramisole, calcium levofolinate, left thyroxine sodium, left thyroxine sodium preparations, lomustine, lonidamine, dronabinol, nitrogen mustard, methylcobalamin, medroxyprogesterone acetate, megestrol acetate, melphalan, esterificated estrogen, 6-mercaptopurine, mesna, methotrexate, 5-aminolevulinic acid methyl ester, miltefosine, minocycline, mitomycin C, mitotane, mitoxantrone, trilostane, citrate adriamycin liposomes, nedaplatin, pegfilgrastim, oprelvekin, neupogen, nilutamide, tamoxifen, NSC-631570, recombinant human interleukin 1-β, octreotide, ondansetron hydrochloride, dehydrogenated cortisone oral solution, oxaliplatin, paclitaxel, prednisone sodium phosphate preparations, oncaspar, pegasys, pentostatin, picibanil, pilocarpine hydrochloride, pirarubicin, plicamycin, porfimer sodium, prednimustine, prednisolone steaglate, prednisone, premarin, procarbazine, recombinant human erythropoietin, raltitrexed, rebif, rhenium-186 etidronate, rituximab, redoxon-A, romurtide, pilocarpine hydrochloride tablets, octreotide, sargramostim, semustine, sizofiran, sobuzoxane, methylprednisolone sodium, paphos acid, stem cell therapy, streptozocin, strontium-89 chloride, levothyroxine sodium, tamoxifen, tamsulosin, tasonermin, tastolactone, taxotere, teceleukin, temozolomide, teniposide, testosterone propionate, methyltestosterone, thioguanine, thiotepa, thyroid stimulating hormone, tiludronic acid, topotecan, toremifene, tositumomab, trastuzumab, treosulfan, tretinoin, methotrexate tablets, trimethyl melamine, trimetrexate, triptorelin acetate, triptorelin pamoate, tegafur-uracil, uridine, valrubicin, vesnarinone, vinblastine, vincristine, vindesine, vinorelbine, virulizin, dextral razoxane, zinostatin stimalamer, ondansetron, paclitaxel protein stabilizer, acolbifene, interferon r-lb, affinitak, aminopterin, arzoxifene, asoprisnil, atamestane, atrasentan, BAY43-9006, avastin, CCI-779, CDC-501, celebrex, cetuximab, crisnatol, cyproterone acetate, decitabine, DN-101, adriamycin-MTC, dSLIM, dutasteride, edotecarin, eflornithine, exatecan, fenretinide, histamine dihydrochloride, histrelin hydrogel implants, holmium-166DOTMP, ibandronic acid, interferon γ, intron-PEG, ixabepilone, keyhole hemocyanin, L-651582, lanreotide, lasofoxifene, libra, lonafamib, miproxifene, minoxicate, MS-209, liposome MTP-PE, MX-6, nafarelin, nemorubicin, neovastat, nolatrexed, Olimson, onco-TCS, osidem, paclitaxel polyglutamate, pamidronate sodium, PN-401, QS-21, quazepam, R-1549, raloxifene, ranpirnase, 13-cis-retinoic acid, satraplatin, seocalcitol, T-138067, tarceva, docosahexaenoic acid paclitaxel, thymosin al, tetrazolylidene, tipifarnib, tirapazamine, TLK-286, toremifene, trans MID-lo7R, valspodar, vapreotide, vatalanib, verteporfin, vinflunine, Z-100 and zoledronic acid or the combinations thereof.

The technical features described above or in the examples can be arbitrary combined. All of the features disclosed in the specification in this case may be used in combination with any composition form; the various features disclosed in the specification can be replaced by any alternative feature that provided the same, equal or similar purpose. Therefore, unless otherwise stated, the disclosed feature is only general examples of equal or similar features.

The advantages of the present invention are:

(1) a novel 2-aminopyrimidine-based compound is provided.

(2) The compounds can effectively inhibit the growth of various tumor cells, and have an inhibitory effect on EGFR and IGF1R protease, which can be used for the preparation of anti-tumor medicines.

(3) The compounds can overcome the resistance to the existing drugs such as gefitinib and erlotinib, and are selective to wild type non-small cell lung cancer and have good pharmacokinetic properties.

The present invention will be further illustrated below with reference to the specific examples. It should be understood that these examples are only to illustrate the invention but not to limit the disclosure of the invention. The experimental methods without specific conditions in the following embodiments are generally carried out according to conventional conditions such as those described in Sambrook et al., Molecular Cloning: Laboratory Manual (New York: Cold Spring Harbor Laboratory Press, 1989), or in accordance with the conditions recommended by the manufacturer. Unless indicated otherwise, parts and percentage are calculated by weight. Unless otherwise defined, the technical terms and scientific terminology used herein are of the same meanings as with that familiar to all to those skilled in the art. In addition, any methods and materials similar or equal to that recorded can be applied in the method described in the present invention. The preferred embodiments and the materials described herein are for demonstration purposes only.

EXAMPLE 1

(E)-N-((3-((5-chloro-4-((naphthalen-2-yl)amino))pyrimidin-2-yl)amino)-4-methoxyphenyl)-4-(dimethylamino)-2-butenamide (CCB118563)

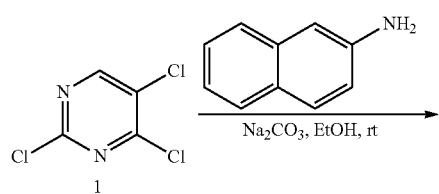

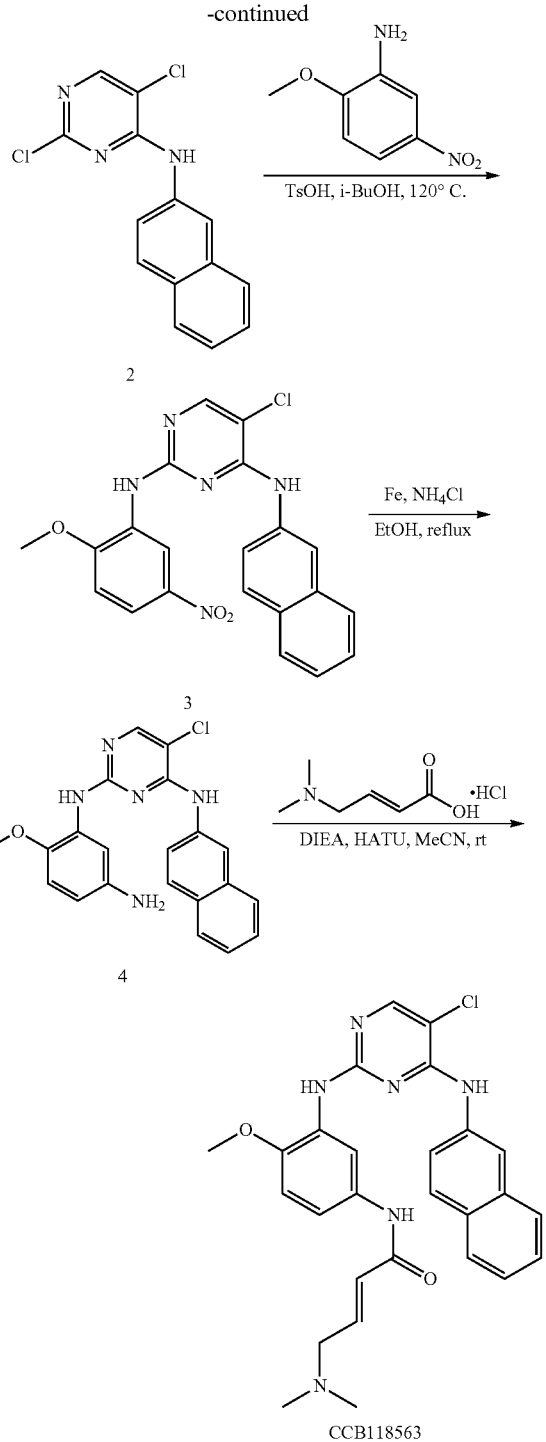

Step 1. 2,5-dichloro-N-(naphthalen-2-yl)pyrimidin-4-amine (2)

2,4,5-trichloropyrimidine (6 g, 32.7 mmol), 2-naphthylamine (4.92 g, 34.4 mmol), and sodium carbonate (6.94 g, 65.4 mmol) were dissolved in anhydrous ethanol (100 mL) and stirred overnight at room temperature. The ice water (300 mL) was added with stirring, and a large amount of solid was precipitated. It was filtered under reduced pressure and dried in vacuo to give a brown solid (8.38 g, yield 88%).

¹H NMR (400 MHz, DMSO-d6): δ 9.74 (s, 1H), 8.42 (s, 1H), 8.09 (d, J=1.6 Hz, 1H), 7.95-7.86 (m, 3H), 7.73 (d, J=8.8 Hz, 1H), 7.54-7.47 (m, 2H).
MS (ESI): m/z 291 [M+H]⁺.

Step 2. 5-Chloro-N2-(2-methoxy-5-nitrophenyl)-N⁴-(naphthyl-2-yl)pyrimidin-2,4-diamine (3)

2,5-dichloro-N-(naphthalen-2-yl)pyrimidin-4-amine (2) (3 g, 10.3 mmol), 2-methoxy-5-nitroaniline (1.91 g, 11.4 mmol), and p-toluenesulfonic acid monohydrate (2.95 g, 15.5 mmol) were added into a tube, and anhydrous sec-butanol (30 mL) was added. It was sealed and stirred overnight at 120° C. The mixture was cooled to room temperature, and 10% NaHCO₃ aqueous solution was added. The mixture was extracted with dichloromethane and spined to almost dried. Anhydrous ethanol was added and pulped. After filtration, the solid was dried in vacuo to give a yellow solid (3.96 g, yield: 91%).
¹H NMR (400 MHz, DMSO-d6): δ 9.09 (s, 1H), 8.84 (d, J=2.8 Hz, 1H), 8.27 (s, 2H), 8.21 (s, 1H), 7.95 (dd, J=8.8 Hz, 2.8 Hz, 1H), 7.83 (d, J=7.2 Hz, 1H), 7.80 (s, 2H), 7.68 (d, J=8.8 Hz, 1H), 7.46-7.39 (m, 2H), 7.23 (d, J=8.8 Hz, 1H), 3.95 (s, 3H).
MS (ESI): m/z 422 [M+H]⁺.

Step 3. N2-(5-amino-2-methoxyphenyl)-5-chloro-N⁴-(naphthalen-2-yl)pyrimidin-2,4-diamine (4)

5-Chloro-N2-(2-methoxy-5-nitrophenyl)-N4-(naphthyl-2-yl)pyrimidin-2,4-diamine (3) (1 g, 2.4 mmol) and iron powder (1.33 g, 24 mmol) were dissolved in ethanol (12 mL). Ammonium chloride saturated solution (1 mL) was added. The mixture was heated under reflux for 2 h and cooled to room temperature. The mixture was filtered through diatomite and spin dried. The residue was purified by column chromatography to give a solid (705 mg, yield: 75%).
¹H NMR (400 MHz, DMSO-d6): δ 8.95 (s, 1H), 8.25 (s, 1H), 8.13 (s, 1H), 7.89-7.78 (m, 5H), 7.49-7.40 (m, 2H), 7.15 (d, J=2.4 Hz, 1H), 6.73 (d, J=8.8 Hz, 1H), 6.24 (dd, J=8.8 Hz, 2.4 Hz, 1H), 4.26 (br, 2H), 3.67 (s, 3H).
MS (ESI): m/z 392 [M+H]⁺.

Step 4. (E)-N-((3-((5-chloro-4-((naphthalen-2-yl)amino))pyrimidin-2-yl)amino)-4-methoxyphenyl)-4-(dimethylamino)-2-butenamide (CCB118563)

N²-(5-amino-2-methoxyphenyl)-5-chloro-N⁴-(naphthalen-2-yl)pyrimidin-2,4-diamine (4) (500 mg, 1.28 mmol), (E)-4-(dimethylamino)but-2-enoic acid hydrochloride (254 mg, 1.53 mmol) and 2-(7-azobenzotriazole)-N,N,N',N'-tetramethyluronium hexafluorophosphate (727 mg, 1.91 mmol) were dissolved in acetonitrile (10 mL). Diisopropylethylamine (0.441 mL) was added, and the mixture was stirred overnight at room temperature. After it was spin dried, 10% NaHCO₃ solution (10 mL) was added. The mixture was extracted for three times with dichloromethane. The organic phases were combined and washed again with saturated brine. After it was spin dried, the residue was purified by column chromatography to give a solid (397 mg, yield: 62%).
¹H NMR (400 MHz, DMSO-d6): δ 9.88 (s, 1H), 8.88 (s, 1H), 8.28 (s, 1H), 8.15 (s, 2H), 7.97 (s, 1H), 7.82 (d, J=8.8 Hz, 1H), 7.77 (m, 2H), 7.67 (d, J=8.0 Hz, 1H), 7.53 (d, J=8.8 Hz, 1H), 7.42-7.35 (m, 2H), 7.00 (d, J=8.8 Hz, 1H), 6.68-6.61 (m, 1H), 6.17 (d, J=15.6 Hz, 1H), 3.76 (s, 3H), 3.01 (d, J=5.6 Hz, 2H), 2.14 (s, 6H).
MS (ESI): m/z 503 [M+H]⁺.

EXAMPLE 2

(E)-N-((3-((5-chloro-4-((quinolin-6-yl)amino))pyrimidin-2-yl)amino)-4-methoxyphenyl)-4-(dimethylamino)-2-butenamide (CCB145213)

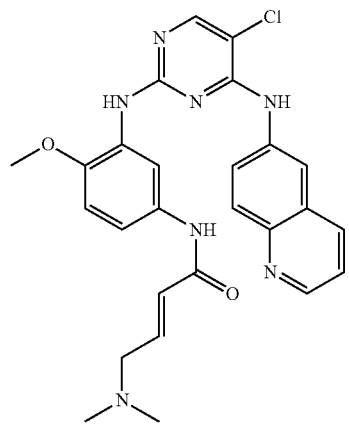 [SMILES: COc1ccc(NC(=O)/C=C/CN(C)C)cc1Nc1ncc(Cl)c(Nc2ccc3ncccc3c2)n1]

The synthetic method was as in Example 1.
¹H NMR (400 MHz, DMSO-d6) δ 9.85 (s, 1H), 9.00 (s, 1H), 8.73 (s, 1H), 8.39 (s, 1H), 8.27 (s, 1H), 8.18 (s, 1H), 8.07-8.01 (m, 2H), 7.98 (s, 1H), 7.87 (d, J=8.8 Hz, 2H), 7.39 (m, 1H), 7.02 (d, J=8.8 Hz, 1H), 6.64-6.58 (m, 1H), 6.12 (d, J=15.6 Hz, 1H), 3.76 (s, 3H), 3.00 (d, J=4.8 Hz, 2H), 2.14 (s, 6H).
MS (ESI); m/z 504 [M+H]⁺.

EXAMPLE 3

(E)-N-((3-((5-chloro-4-((quinolin-3-yl)amino))pyrimidin-2-yl)amino)-4-methoxyphenyl)-4-(dimethylamino)-2-butenamide (CCB145221)

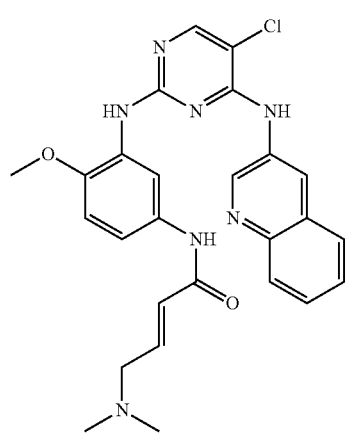 [SMILES: COc1ccc(NC(=O)/C=C/CN(C)C)cc1Nc1ncc(Cl)c(Nc2cnc3ccccc3c2)n1]

The synthetic method was as in Example 1.
¹H NMR (400 MHz, DMSO-d6) δ 9.81 (s, 1H), 9.17 (s, 1H), 9.15 (d, J=2.4 Hz, 1H), 8.71 (d, J=2.0 Hz, 1H), 8.28 (s, 1H), 8.19 (s, 1H), 7.97 (d, J=2.0 Hz, 1H), 7.91 (d, J=8.8 Hz, 1H), 7.69 (d, J 10=7.6 Hz, 1H), 7.60 (t, J=8.0 Hz, 1H), 7.56 (dd, J=8.8 Hz, 2.4 Hz, 1H), 7.49 (t, J=8.0 Hz, 1H), 7.01 (d, J=8.8 Hz, 1H), 6.64-6.57 (m, 1H), 6.13 (d, J=15.6 Hz, 1H), 3.76 (s, 3H), 3.01 (d, J=5.6 Hz, 2H), 2.15 (s, 6H).

MS (ESI): m/z 504 [M+H]$^+$.

EXAMPLE 4

(E)-N-((3-((5-chloro-4-((indol-5-yl)amino))pyrimidin-2-yl)amino)-4-methoxyphenyl)-4-(dimethylamino)-2-butenamide (CCB145231)

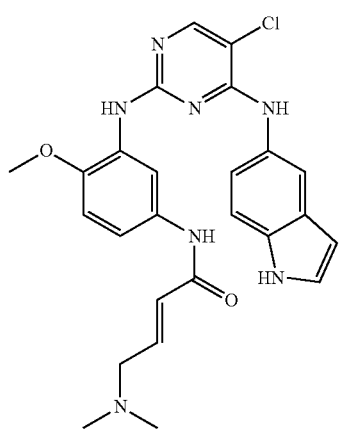 [SMILES: COc1ccc(NC(=O)/C=C/CN(C)C)cc1Nc1ncc(Cl)c(Nc2ccc3[nH]ccc3c2)n1]

The synthetic method was as in Example 1.

$^1$H NMR (400 MHz, DMSO-d6) δ 9.77 (s, 1H), 8.62 (s, 1H), 8.07 (s, 1H), 8.05 (s, 1H), 7.75 (s, 1H), 7.70 (s, 1H), 7.45 (d, J=8.8 Hz, 1H), 7.30-7.24 (m, 3H), 6.94 (d, J=8.8 Hz, 1H), 6.71-6.64 (m, 1H), 6.34 (s, 1H), 6.21 (d, J=15.6 Hz, 1H), 3.75 (s, 3H), 3.04 (d, J=6.0 Hz, 2H), 2.17 (s, 6H).

MS (ESI):m/z 492 [M+H]$^+$.

EXAMPLE 5

(E)-N-((3-((5-chloro-4-(N-methyl-(naphthalen-2-yl)amino))pyrimidin-2-yl)amino)-4-methoxyphenyl)-4-(dimethylamino)-2-butenamide (CCB145295)

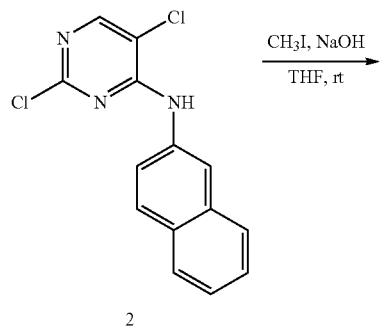

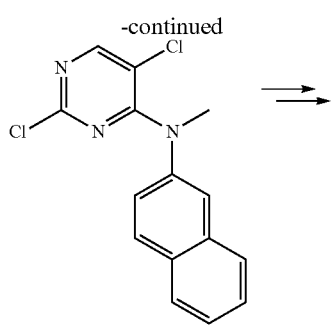

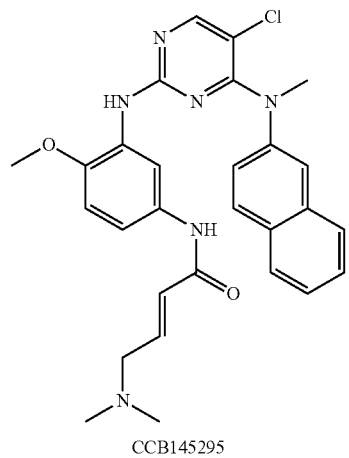 [SMILES: COc1ccc(NC(=O)/C=C/CN(C)C)cc1Nc1ncc(Cl)c(N(C)c2ccc3ccccc3c2)n1]

CCB145295

The synthesis of intermediate 5 was as follows:
2,5-dichloro-N-(naphthalen-2-yl)pyrimidin-4-amine (2) (3 g, 10.3 mmol), and sodium hydroxide (824 mg, 20.6 mmol) were dissolved in tetrahydrofuran (40 mL). Methyl iodide (0.96 mL, 15.45 mmol) was added dropwise in ice bath, warmed to room temperature and stirred for 2 h. After it was spin dried, water (10 mL) was added. The mixture was extracted for three times with dichloromethane and dried over anhydrous Na$_2$SO$_4$. After it was spin dried, the residue was purified by column chromatography to give a solid (1.57 g, yield: 50%).

The synthetic method of the final product CCB145295 from intermediate 5 was carried out as steps 2-4 in Example 1.

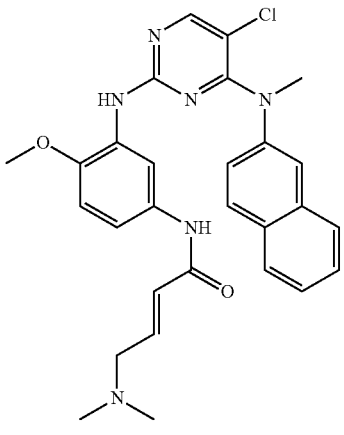

CCB145295

$^{1}$H NMR (400 MHz, DMSO-d6) δ 9.89 (s, 1H), 8.47 (s, 1H), 8.06 (s, 1H), 8.01 (s, 1H), 7.93 (d, J=8.8 Hz, 1H), 7.90 (d, J=7.2 Hz, 1H), 7.85 (d, J=7.2 Hz, 1H), 7.63 (s, 1H), 7.48 (m, 2H), 7.43 (d, J=8.8 Hz, 1H), 7.31 (d, J=8.8 Hz, 1H), 6.99 (d, J=8.8 Hz, 1H), 6.71-6.64 (m, 1H), 6.25 (d, J=15.6 Hz, 1H), 3.86 (s, 3H), 3.53 (s, 3H), 3.02 (d, J=5.6 Hz, 2H), 2.15 (s, 6H).

MS (ESI):m/z 517 [M+H]$^{+}$.

EXAMPLE 6

(E)-N-((3-((5-chloro-4-((naphthalen-2-yl)oxy))pyrimidin-2-yl)amino)-4-methoxyphenyl)-4-(dimethylamino)-2-butenamide (CCB145260)

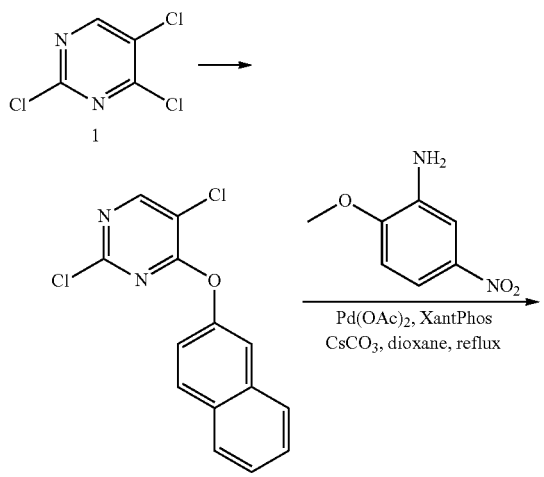

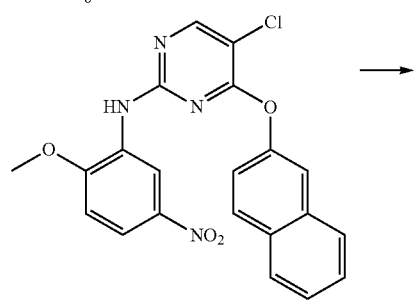

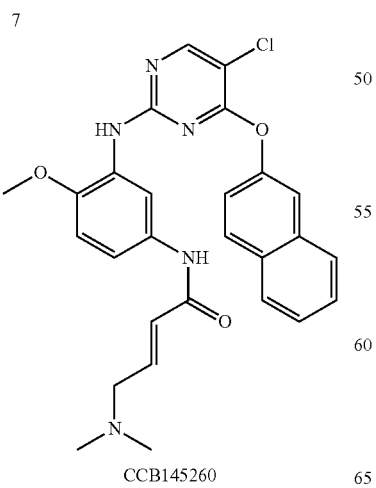

The synthetic method of intermediate 6 from starting material 1 was carried out as step 1 in Example 1.

Wherein, the synthesis of intermediate 7 was as follows:

Intermediate 6 (870 mg, 3 mmol), 2-methoxy-5-nitroaniline (504 mg, 3 mmol), palladium acetate (13.5 mg, 0.06 mmol), 4,5-bis(diphenylphosphino)-9,9-dimethylxanthene (87 mg, 0.15 mmol), cesium carbonate (1.96 g, 6 mmol) were dissolved in dioxane (20 mL). The mixture was displaced with argon three times, heated under reflux and stirred overnight. After it was naturally warmed to room temperature and spin dried, water (10 mL) was added. The mixture was extracted for three times with dichloromethane and dried over anhydrous Na$_2$SO$_4$. After it was spin dried, the residue was purified by column chromatography to give a solid (1.04 g, yield: 82%).

The synthetic method of the final product CCB145260 from intermediate 7 was carried out as steps 3-4 in Example 1.

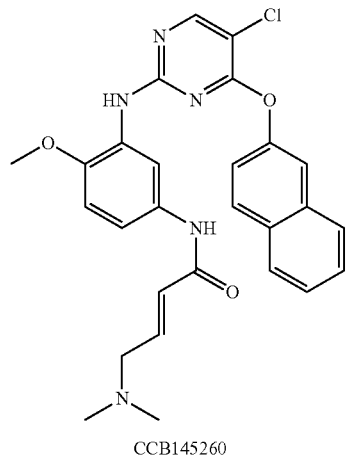 [SMILES: COc1ccc(NC(=O)/C=C/CN(C)C)cc1Nc1ncc(Cl)c(Oc2ccc3ccccc3c2)n1]

$^{1}$H NMR (400 MHz, DMSO-d6) δ 9.77 (s, 1H), 8.43 (s, 1H), 8.23 (s, 1H), 7.96 (d, J=8.8 Hz, 1H), 7.91 (m, 2H), 7.84 (s, 1H), 7.79 (d, J=2.0 Hz, 1H), 7.55-7.51 (m, 2H), 7.46 (dd, J=8.8 Hz, 2.0 Hz, 1H), 7.33 (dd, J=8.8 Hz, 2.0 Hz, 1H), 6.87 (d, J=8.8 Hz, 1H), 6.71-6.65 (m, 1H), 6.22 (d, J=15.6 Hz, 1H), 3.68 (s, 3H), 3.01 (d, J=6.0 Hz, 2H), 2.18 (s, 6H).

MS (ESI):m/z 504 [M+H]$^{+}$.

EXAMPLE 7

(E)-N-((3-((5-chloro-4-((naphthalen-2-yl)sulfenyl))pyrimidin-2-yl)amino)-4-methoxyphenyl)-4-(dimethylamino)-2-butenamide (CCB145291)

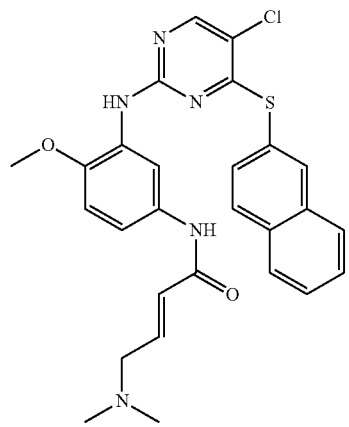 [SMILES: COc1ccc(NC(=O)/C=C/CN(C)C)cc1Nc1ncc(Cl)c(Sc2ccc3ccccc3c2)n1]

The synthetic method was as in Example 1.

¹H NMR (400 MHz, DMSO-d6) δ 9.73 (s, 1H), 8.27 (s, 2H), 8.16 (s, 1H), 7.90 (d, J=8.0 Hz, 2H), 7.82 (d, J=8.0 Hz, 1H), 7.66 (s, 1H), 7.60-7.54 (m, 3H), 7.29 (d, J=8.8 Hz, 1H), 6.71-6.65 (m, 2H), 6.20 (d, J=15.6 Hz, 1H), 3.57 (s, 3H), 3.05 (d, J=5.2 Hz, 2H), 2.18 (s, 6H).

MS (ESI):m/z 520 [M+H]⁺.

EXAMPLE 8

(E)-N-((3-(4-((naphthalen-2-yl)amino)pyrimidin-2-yl)amino)-4-methoxyphenyl)-4-(dimethylamino)-2-butenamide (CCB145242)

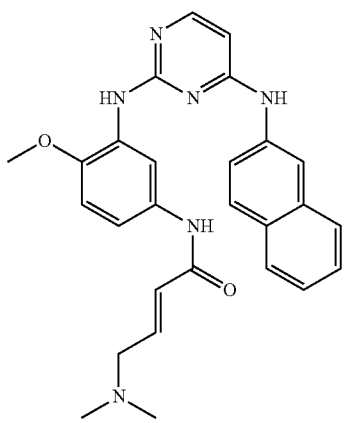 [SMILES: COc1ccc(NC(=O)/C=C/CN(C)C)cc1Nc1nccc(Nc2ccc3ccccc3c2)n1]

The synthetic method was as in Example 1.

¹H NMR (400 MHz, DMSO-d6) δ 9.84 (s, 1H), 9.34 (s, 1H), 8.72 (s, 1H), 8.26-8.25 (m, 2H), 7.85-7.84 (m, 2H), 7.79-7.76 (m, 2H), 7.52 (s, 1H), 7.47-7.39 (m, 2H), 7.21 (s, 1H), 7.09 (s, 1H), 6.70-6.63 (m, 1H), 6.21 (d, J=15.2 Hz, 1H), 3.02 (d, J=6.0 Hz, 2H), 2.15 (s, 6H), 1.91 (s, 3H).

MS (ESI):m/z 469 [M+H]⁺.

EXAMPLE 9

(E)-N-((3-((5-bromo-4-((naphthalen-2-yl)amino))pyrimidin-2-yl)amino)-4-methoxyphenyl)-4-(dimethylamino)-2-butenamide (CCB145286)

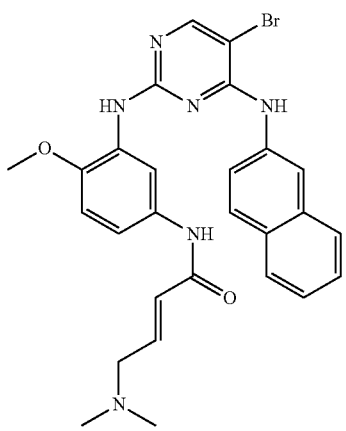

The synthetic method was as in Example 1.

¹H NMR (400 MHz, DMSO-d6) δ 9.83 (s, 1H), 8.61 (s, 1H), 8.24 (s, 1H), 8.22 (s, 1H), 8.15 (s, 1H), 7.96 (s, 1H), 7.80-7.78 (m, 3H), 7.67 (d, J=7.6 Hz, 1H), 7.51 (d, J=8.8 Hz, 1H), 7.43-7.35 (m, 2H), 6.99 (d, J=8.8 Hz, 1H), 6.68-6.61 (m, 1H), 6.15 (d, J=15.6 Hz, 1H), 3.75 (s, 3H), 3.01 (d, J=5.6 Hz, 2H), 2.15 (s, 6H).

MS (ESI); m/z 547 [M+H]⁺.

EXAMPLE 10

(E)-N-((3-((5-fluoro-4-((naphthalen-2-yl)amino))pyrimidin-2-yl)amino)-4-methoxyphenyl)-4-(dimethylamino)-2-butenamide (CCB145287)

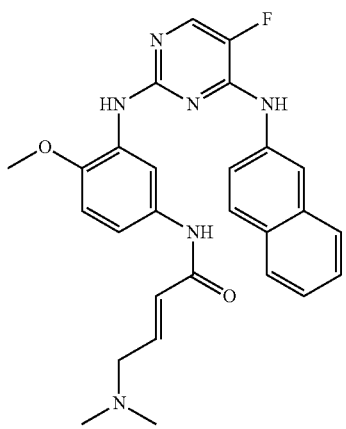 [SMILES: COc1ccc(NC(=O)/C=C/CN(C)C)cc1Nc1ncc(F)c(Nc2ccc3ccccc3c2)n1]

The synthetic method was as in Example 1.

¹H NMR (400 MHz, DMSO-d6) δ 9.85 (s, 1H), 9.50 (s, 1H), 8.43 (s, 1H), 8.12 (d, J=3.6 Hz, 1H), 8.07 (d, J=2.4 Hz, 1H), 7.97 (s, 1H), 7.84 (dd, J=8.8 Hz, 2.4 Hz, 1H), 7.79-7.76 (m, 2H), 7.67 (d, J=7.6 Hz, 1H), 7.53 (dd, J=8.8 Hz, 2.4 Hz, 1H), 7.40 (t, J=6.8 Hz, 1H), 7.35 (t, J=6.8 Hz, 1H), 7.00 (d, J=8.8 Hz, 1H), 6.67-6.60 (m, 1H), 6.15 (d, J=15.6 Hz, 1H), 3.79 (s, 3H), 3.00 (d, J=5.6 Hz, 2H), 2.14 (s, 6H).

MS (ESI); m/z 487 [M+H]⁺.

EXAMPLE 11

(E)-N-((3-((5-methyl-4-((naphthalen-2-yl)amino))pyrimidin-2-yl)amino)-4-methoxyphenyl)-4-(dimethylamino)-2-butenamide (CCB145289)

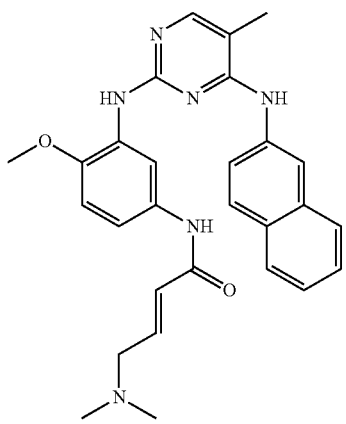 [SMILES: COc1ccc(NC(=O)/C=C/CN(C)C)cc1Nc1ncc(C)c(Nc2ccc3ccccc3c2)n1]

The synthetic method was as in Example 1.

¹H NMR (400 MHz, DMSO-d6) δ 9.79 (s, 1H), 8.44 (s, 1H), 8.31 (s, 1H), 8.20 (s, 1H), 7.93 (s, 1H), 7.86 (d, J=8.8 Hz, 1H), 7.79-7.76 (m, 2H), 7.70 (d, J=8.0 Hz, 1H), 7.60 (s, 1H), 7.47 (d, J=8.8 Hz, 1H), 7.40 (t, J=7.2 Hz, 1H), 7.36 (t,

J=7.2 Hz, 1H), 6.96 (d, J=8.8 Hz, 1H), 6.67-6.61 (m, 1H), 6.16 (d, J=15.2 Hz, 1H), 3.80 (s, 3H), 3.00 (d, J=5.6 Hz, 2H), 2.17 (s, 3H), 2.15 (s, 6H).
MS (ESI); m/z 483 [M+H]+.

EXAMPLE 12

(E)-N-((3-((5-methoxy-4-((naphthalen-2-yl)amino))pyrimidin-2-yl)amino)-4-methoxyphenyl)-4-(dimethylamino)-2-butenamide (CCB145268)

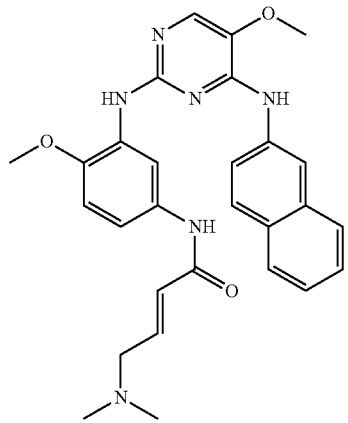 [SMILES: COc1ccc(NC(=O)/C=C/CN(C)C)cc1Nc1ncc(OC)c(Nc2ccc3ccccc3c2)n1]

The synthetic method was as in Example 1.
1H NMR (400 MHz, DMSO-d6) δ 9.84 (s, 1H), 8.92 (s, 1H), 8.49 (s, 1H), 8.27 (s, 1H), 7.90-7.87 (m, 2H), 7.79-7.76 (m, 2H), 7.70 (d, J=7.6 Hz, 1H), 7.58 (s, 1H), 7.45-7.32 (m, 3H), 6.97 (d, J=8.8 Hz, 1H), 6.67-6.61 (m, 1H), 6.17 (d, J=15.6 Hz, 1H), 3.90 (s, 3H), 3.82 (s, 3H), 3.03 (d, J=5.2 Hz, 2H), 2.16 (s, 6H).
MS (ESI): m/z 499 [M+H]+.

EXAMPLE 13

(E)-N-((3-((5-cyano-4-((naphthalen-2-yl)amino))pyrimidin-2-yl)amino)-4-methoxyphenyl)-4-(dimethylamino)-2-butenamide (CCB145293)

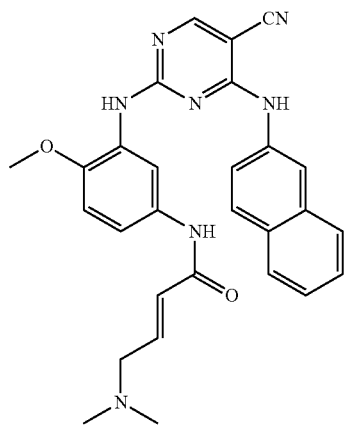 [SMILES: COc1ccc(NC(=O)/C=C/CN(C)C)cc1Nc1ncc(C#N)c(Nc2ccc3ccccc3c2)n1]

The synthetic method was as in Example 1.
1H NMR (400 MHz, DMSO-d6) δ 9.90 (s, 1H), 9.46 (br, 1H), 9.02 (br, 1H), 8.49 (s, 1H), 8.17 (br, 1H), 7.79 (s, 1H), 7.73 (s, 3H), 7.60-7.58 (m, 2H), 7.40-7.35 (m, 2H), 7.04 (d, J=9.2 Hz, 1H), 6.70-6.63 (m, 1H), 6.17 (d, J=15.6 Hz, 1H), 3.73 (s, 3H), 3.01 (d, J=5.2 Hz, 2H), 2.15 (s, 6H).
MS (ESI):m/z 494 [M+H]+.

EXAMPLE 14

(E)-N-((3-((5-trifluoromethyl-4-((naphthalen-2-yl)amino))pyrimidin-2-yl)amino)-4-methoxyphenyl)-4-(dimethylamino)-2-butenamide (CCB145274)

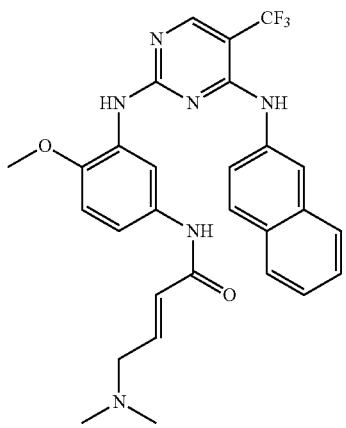 [SMILES: COc1ccc(NC(=O)/C=C/CN(C)C)cc1Nc1ncc(C(F)(F)F)c(Nc2ccc3ccccc3c2)n1]

The synthetic method was as in Example 1.
1H NMR (400 MHz, DMSO-d6) δ 9.83 (s, 1H), 8.63 (br, 1H), 8.56 (s, 1H), 8.36 (s, 1H), 8.07 (s, 1H), 7.83 (d, J=8.0 Hz, 1H), 7.78-7.67 (m, 4H), 7.51 (d, J=8.8 Hz, 1H), 7.42-7.39 (m, 2H), 6.99 (d, J=8.8 Hz, 1H), 6.69-6.63 (m, 1H), 6.17 (d, J=15.2 Hz, 1H), 3.72 (s, 3H), 3.03 (d, J=5.6 Hz, 2H), 2.16 (s, 6H).
MS (ESI):m/z 537 [M+H]+.

EXAMPLE 15

(E)-N-((3-((5-isopropyl-4-((naphthalen-2-yl)amino))pyrimidin-2-yl)amino)-4-methoxyphenyl)-4-(dimethylamino)-2-butenamide (CCB145283)

-continued

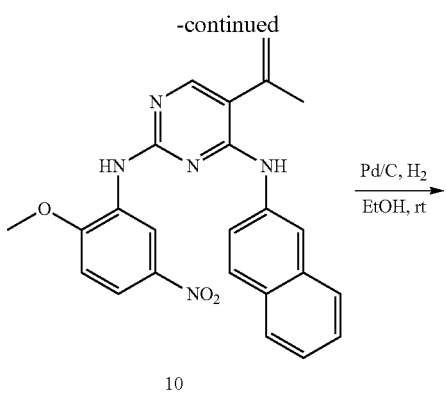

10

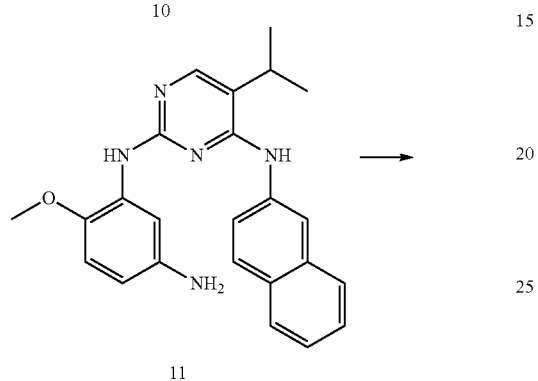

11

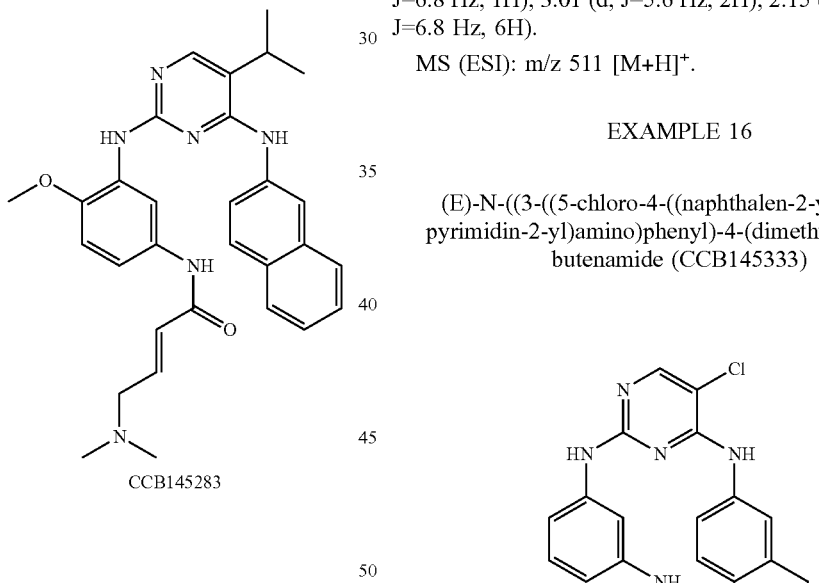

CCB145283

The synthetic method of intermediate 9 from starting material 8 was carried out as steps 1-2 in Example 1.
The synthesis of intermediate 11 was as follows:

Step 1. N2-(2-methoxy-5-nitrophenyl)-N$^4$-(naphthalen-2-yl)-5-isopropenylpyrimidine-2,4-diamine (Intermediate 10)

Intermediate 9 (771 mg, 1.66 mmol), 1,1'-bis(diphenylphosphino) ferrocene palladium dichloride (61 mg, 0.08 mmol), and potassium carbonate (686 mg, 4.97 mmol) were added into a tube. Dioxane/water (20 mL, v/v=3/1) was added and the mixture was displaced with argon three times.
Finally, isopropenylboronic acid pinacol ester (0.62 mL, 3.32 mmol) was added and the mixture was sealed and stirred overnight at 80° C. After it was cooled to room temperature, 10% NaHCO$_3$ aqueous solution was added. The mixture was extracted for three times with dichloromethane and dried over anhydrous Na$_2$SO$_4$. After it was spin dried, the residue was purified by column chromatography to give a solid (507 mg, yield: 71%).

Step 2. 5-isopropyl-N2-(2-methoxy-5-aminophenyl)-N4-(naphthalen-2-yl) pyrimidine-2,4-diamine (Intermediate 11)

Ethanol (10 mL) solution was added into a reaction flask of Intermediate 10 (500 mg, 1.17 mmol) and 10% Pd/C (50 mg). The mixture was displaced with hydrogen for three times, and reacted for 3 h at room temperature under a hydrogen balloon. The mixture was filtered through diatomite and spin dried. The residue was purified by column chromatography to give a solid (303 mg, yield: 65%).

The synthetic method of the final product CCB145283 from intermediate 11 was carried out as step 4 in Example 1.

$^1$H NMR (400 MHz, DMSO-d6):δ 9.76 (s, 1H), 8.51 (s, 1H), 8.24 (s, 1H), 8.23 (s, 1H), 8.02 (s, 1H), 7.85 (d, J=8.8 Hz, 1H), 7.77 (d, J=8.8 Hz, 2H), 7.71 (d, J=8.0 Hz, 1H), 7.56 (s, 1H), 7.44-7.33 (m, 3H), 6.95 (d, J=8.8 Hz, 1H), 6.67-6.60 (m, 1H), 6.15 (d, J=15.2 Hz, 1H), 3.79 (s, 3H), 3.27 (m, J=6.8 Hz, 1H), 3.01 (d, J=5.6 Hz, 2H), 2.15 (s, 6H), 1.26 (s, J=6.8 Hz, 6H).

MS (ESI): m/z 511 [M+H]$^+$.

EXAMPLE 16

(E)-N-((3-((5-chloro-4-((naphthalen-2-yl)amino))pyrimidin-2-yl)amino)phenyl)-4-(dimethylamino)-2-butenamide (CCB145333)

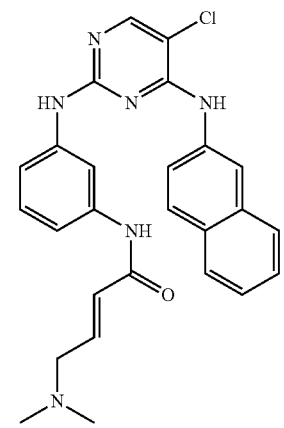 [SMILES: CN(C)C/C=C/C(=O)Nc1cccc(Nc2ncc(Cl)c(Nc3ccc4ccccc4c3)n2)c1]

The synthetic method was as in Example 1.

$^1$H NMR (400 MHz, DMSO-d6) δ 9.92 (s, 1H), 9.38 (s, 1H), 8.93 (br, 1H), 8.37 (s, 1H), 8.18 (s, 1H), 7.84 (s, 3H), 7.79 (s, 2H), 7.48-7.39 (m, 3H), 7.28 (d, J=8.0 Hz, 1H), 7.04 (t, J=8.0 Hz, 1H), 6.72-6.65 (m, 1H), 6.23 (d, J=15.6 Hz, 1H), 3.02 (d, J=5.2 Hz, 2H), 2.16 (s, 6H).

MS (ESI):m/z 473 [M+H]$^+$.

EXAMPLE 17

(E)-N-((3-((5-chloro-4-((naphthalen-2-ylamino))pyrimidin-2-yl)amino)-4-methylphenyl)-4-(dimethylamino)-2-butenamide (CCB145340)

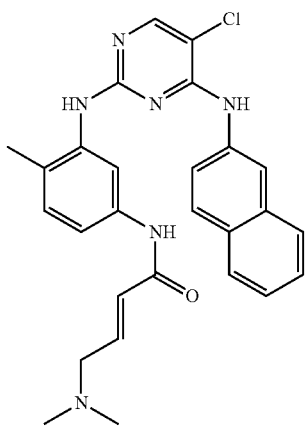 [SMILES: Cc1ccc(NC(=O)/C=C/CN(C)C)cc1Nc1ncc(Cl)c(Nc2ccc3ccccc3c2)n1]

The synthetic method was as in Example 1.
¹H NMR (400 MHz, DMSO-d6) δ 9.98 (s, 1H), 8.75 (s, 1H), 8.73 (s, 1H), 8.29 (s, 1H), 8.11 (s, 1H), 7.78-7.68 (m, 4H), 7.54-7.51 (m, 2H), 7.38-7.31 (m, 2H), 7.17 (d, J=8.4 Hz, 1H), 6.71-6.64 (m, 1H), 6.20 (d, J=15.6 Hz, 1H), 3.01 (d, J=5.6 Hz, 2H), 2.14 (s, 3H), 2.13 (s, 6H).
MS (ESI):m/z 487 [M+H]⁺.

EXAMPLE 18

(E)-N-((3-((5-chloro-4-((naphthalen-2-ylamino))pyrimidin-2-yl)amino)-4-fluorophenyl)-4-(dimethylamino)-2-butenamide (CCB145329)

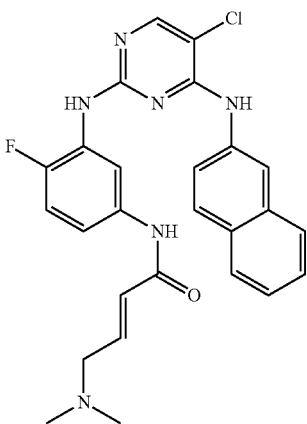 [SMILES: CN(C)C/C=C/C(=O)Nc1ccc(F)c(Nc2ncc(Cl)c(Nc3ccc4ccccc4c3)n2)c1]

The synthetic method was as in Example 1.
¹H NMR (400 MHz, DMSO-d6) δ 10.21 (s, 1H), 9.03 (s, 1H), 8.87 (s, 1H), 8.30 (s, 1H), 8.15 (s, 1H), 7.86 (d, J=6.8 Hz, 1H), 7.81-7.73 (m, 3H), 7.62 (d, J=8.0 Hz, 1H), 7.53 (s, 1H), 7.42-7.34 (m, 2H), 7.20 (t, J=9.6 Hz, 1H), 6.72-6.65 (m, 1H), 6.23 (d, J=15.6 Hz, 1H), 3.02 (d, J=5.2 Hz, 2H), 2.15 (s, 6H).
MS (ESI):m/z 491 [M+H]⁺.

EXAMPLE 19

(E)-N-((3-((5-chloro-4-((naphthalen-2-yl)amino))pyrimidin-2-yl)amino)-4-ethoxyphenyl)-4-(dimethylamino)-2-butenamide (CCB145373)

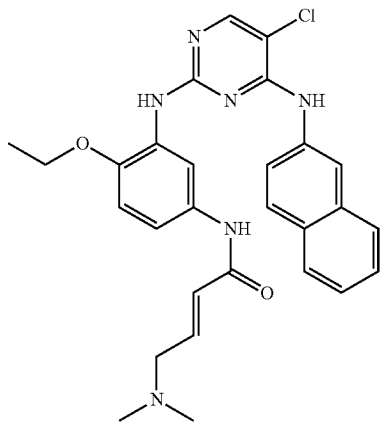

The synthetic method was as in Example 1.
¹H NMR (400 MHz, DMSO-d6) δ 9.81 (s, 1H), 8.90 (s, 1H), 8.31 (s, 1H), 8.17 (s, 1H), 8.08 (s, 1H), 8.00 (s, 1H), 7.82 (d, J=8.8 Hz, 1H), 7.77 (m, 2H), 7.64 (d, J=8.0 Hz, 1H), 7.49 (dd, J=8.8 Hz, 1.6 Hz, 1H), 7.41 (d, J=6.8 Hz, 1H), 7.38-7.34 (m, 1H), 6.98 (d, J=8.8 Hz, 1H), 6.72-6.60 (m, 1H), 6.14 (d, J=15.2 Hz, 1H), 4.01 (q, 2H), 3.01 (d, J=6.0 Hz, 2H), 2.15 (s, 6H), 1.27 (t, 3H).
MS (ESI): m/z 517 [M+H]⁺.

EXAMPLE 20

(E)-N-((3-((5-chloro-4-((naphthalen-2-yl)amino))pyrimidin-2-yl)amino)-4-isopropoxyphenyl)-4-(dimethylamino)-2-butenamide (CCB145384)

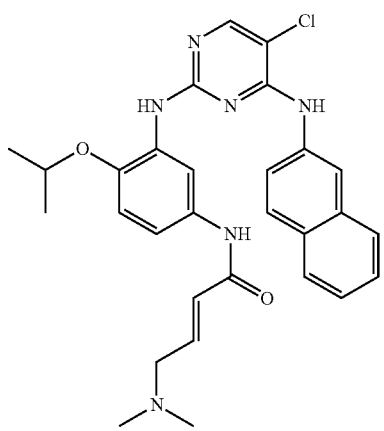 [SMILES: CC(C)Oc1ccc(NC(=O)/C=C/CN(C)C)cc1Nc1ncc(Cl)c(Nc2ccc3ccccc3c2)n1]

The synthetic method was as in Example 1.
¹H NMR (400 MHz, DMSO-d6):δ 9.80 (s, 1H), 8.93 (s, 1H), 8.32 (s, 1H), 8.17 (s, 1H), 8.05 (s, 1H), 7.98 (s, 1H), 7.83 (d, J=8.8 Hz, 1H), 7.77 (d, J=8.8 Hz, 2H), 7.65 (d, J=8.0 Hz, 1H), 7.47 (d, J=8.8 Hz, 1H), 7.43-7.35 (m, 2H), 7.00 (d, J=8.8 Hz, 1H), 6.67-6.60 (m, 1H), 6.14 (d, J=15.2 Hz, 1H), 4.51 (m, 1H), 3.01 (d, J=6.0 Hz, 2H), 2.15 (s, 6H), 1.24 (s, 3H), 1.22 (s, 3H).
MS (ESI): m/z 531 [M+H]⁺.

EXAMPLE 21

(E)-N-((3-((5-chloro-4-((naphthalen-2-yl)amino))pyrimidin-2-yl)amino)-5-methylphenyl)-4-(dimethylamino)-2-butenamide (CCB145344)

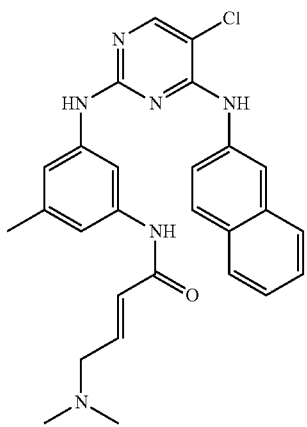 [SMILES: Cc1cc(NC(=O)/C=C/CN(C)C)cc(Nc2ncc(Cl)c(Nc3ccc4ccccc4c3)n2)c1]

The synthetic method was as in Example 1.

$^1$H NMR (400 MHz, DMSO-d6): δ 9.85 (s, 1H), 9.34 (s, 1H), 8.97 (s, 1H), 8.33 (s, 1H), 8.18 (s, 1H), 7.86-7.81 (m, 3H), 7.76 (d, J=8.0 Hz, 1H), 7.55 (s, 1H), 7.47-7.39 (m, 2H), 7.23 (s, 1H), 7.11 (s, 1H), 6.70-6.63 (m, 1H), 6.22 (d, J=15.2 Hz, 1H), 3.02 (d, J=5.6 Hz, 2H), 2.15 (s, 6H), 1.95 (s, 3H).
MS (ESI):m/z 487 [M+H]$^+$.

EXAMPLE 22

(E)-N-((5-((5-chloro-4-((naphthalen-2-yl)amino))pyrimidin-2-yl)amino)-2-methylphenyl)-4-(dimethylamino)-2-butenamide (CCB145346)

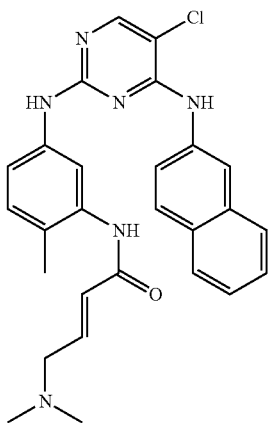 [SMILES: Cc1ccc(Nc2ncc(Cl)c(Nc3ccc4ccccc4c3)n2)cc1NC(=O)/C=C/CN(C)C]

The synthetic method was as in Example 1.

$^1$H NMR (400 MHz, DMSO-d6): δ 9.36 (s, 1H), 9.33 (s, 1H), 8.97 (s, 1H), 8.32 (s, 1H), 8.18 (s, 1H), 7.87-7.79 (m, 4H), 7.64 (s, 1H), 7.50-7.49 (m, 2H), 7.43 (t, J=7.2 Hz, 1H), 6.93 (d, J=8.0 Hz, 1H), 6.71-6.64 (m, 1H), 6.33 (d, J=15.2 Hz, 1H), 3.14 (d, J=4.0 Hz, 2H), 2.24 (s, 6H), 2.10 (s, 3H).
MS (ESI):m/z 487 [M+H]$^+$.

EXAMPLE 23

(E)-N-((5-((5-chloro-4-((naphthalen-2-yl)amino))pyrimidin-2-yl)amino)-2-fluoro-4-methoxyphenyl)-4-(dimethylamino)-2-butenamide (CCB145380)

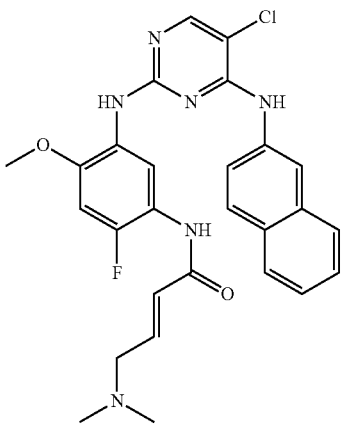 [SMILES: COc1cc(F)c(NC(=O)/C=C/CN(C)C)cc1Nc1ncc(Cl)c(Nc2ccc3ccccc3c2)n1]

The synthetic method was as in Example 1.

$^1$H NMR (400 MHz, DMSO-d6): δ 9.63 (s, 1H), 8.88 (s, 1H), 8.20 (s, 2H), 8.12 (s, 1H), 8.07 (d, J=8.0 Hz, 1H), 7.83-7.75 (m, 3H), 7.69 (d, J=8.0 Hz, 1H), 7.46-7.37 (m, 2H), 7.05 (d, J=12.4 Hz, 1H), 6.68-6.61 (m, 1H), 6.31 (d, J=15.2 Hz, 1H), 3.76 (s, 3H), 3.02 (d, J=5.6 Hz, 2H), 2.16 (s, 6H).
MS (ESI):m/z 521 [M+H]$^+$.

EXAMPLE 24

(E)-N-((3-((5-bromo-4-((naphthalen-2-yl)amino))pyrimidin-2-yl)amino)phenyl)-4-(dimethylamino)-2-butenamide (CCB145335)

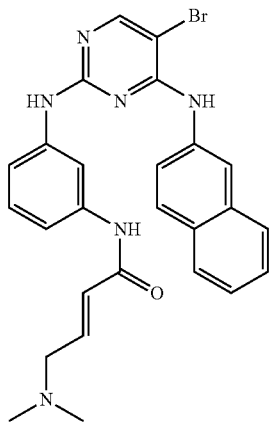 [SMILES: CN(C)C/C=C/C(=O)Nc1cccc(Nc2ncc(Br)c(Nc3ccc4ccccc4c3)n2)c1]

The synthetic method was as in Example 1.

$^1$H NMR (400 MHz, DMSO-d6): δ 9.98 (s, 1H), 9.41 (s, 1H), 8.71 (s, 1H), 8.32 (s, 1H), 8.26 (s, 1H), 7.85 (d, J=7.6 Hz, 1H), 7.79 (d, J=8.4 Hz, 1H), 7.48-7.42 (m, 3H), 7.27 (d, J=7.6 Hz, 1H), 6.99 (t, J=7.6 Hz, 1H), 6.70-6.66 (m, 1H), 6.24 (d, J=15.6 Hz, 1H), 3.03 (d, J=4.8 Hz, 2H), 2.16 (s, 6H).
MS (ESI): m/z 517 [M+H]$^+$.

EXAMPLE 25

(E)-N-((3-((5-bromo-4-((naphthalen-2-yl)amino))pyrimidin-2-yl)amino)-4-methylphenyl)-4-(dimethylamino)-2-butenamide (CCB145339)

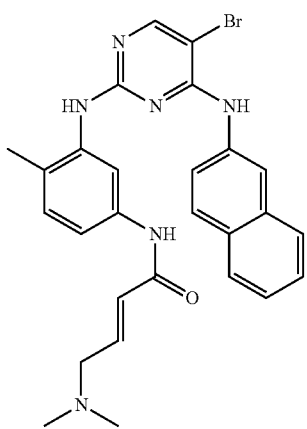 [SMILES: Cc1ccc(NC(=O)/C=C/CN(C)C)cc1Nc1ncc(Br)c(Nc2ccc3ccccc3c2)n1]

The synthetic method was as in Example 1.
$^1$H NMR (400 MHz, DMSO-d6):δ 10.02 (s, 1H), 8.79 (s, 1H), 8.47 (s, 1H), 8.25 (s, 1H), 8.20 (s, 1H), 7.73-7.68 (m, 4H), 7.53 (d, J=8.0 Hz, 2H), 7.37-7.34 (m, 2H), 7.17 (d, J=8.0 Hz, 1H), 6.70-6.66 (m, 1H), 6.22 (d, J=15.2 Hz, 1H), 3.07 (d, J=4.0 Hz, 2H), 2.18 (s, 6H), 2.14 (s, 3H).
MS (ESI): m/z 531 [M+H]$^+$.

EXAMPLE 26

(E)-N-((3-((5-bromo-4-((naphthalen-2-yl)amino))pyrimidin-2-yl)amino)-4-fluorophenyl)-4-(dimethylamino)-2-butenamide (CCB145330)

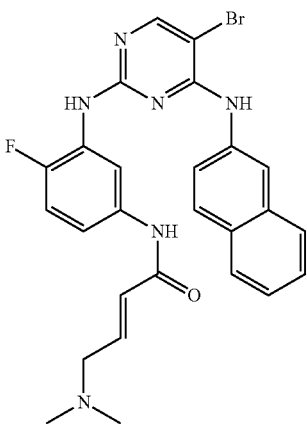 [SMILES: CN(C)C/C=C/C(=O)Nc1ccc(F)c(Nc2ncc(Br)c(Nc3ccc4ccccc4c3)n2)c1]

The synthetic method was as in Example 1.
$^1$H NMR (400 MHz, DMSO-d6):δ 10.14 (s, 1H), 9.03 (s, 1H), 8.59 (s, 1H), 8.24 (s, 1H), 8.22 (s, 1H), 7.84 (d, J=7.2 Hz, 1H), 7.78-7.73 (m, 3H), 7.63 (d, J=8.0 Hz, 1H), 7.52 (d, J=8.0 Hz, 1H), 7.43-7.34 (m, 2H), 7.19 (t, J=9.6 Hz, 1H), 6.72-6.65 (m, 1H), 6.21 (d, J=15.6 Hz, 1H), 3.03 (d, J=5.6 Hz, 2H), 2.15 (s, 6H).
MS (ESI): m/z 535 [M+H]$^+$.

EXAMPLE 27

(E)-N-((3-((5-bromo-4-((naphthalen-2-yl)amino))pyrimidin-2-yl)amino)-4-ethoxyphenyl)-4-(dimethylamino)-2-butenamide (CCB145374)

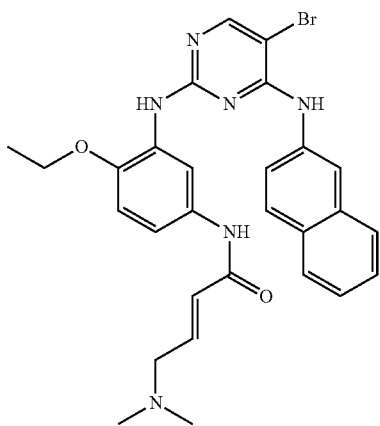 [SMILES: CCOc1ccc(NC(=O)/C=C/CN(C)C)cc1Nc1ncc(Br)c(Nc2ccc3ccccc3c2)n1]

The synthetic method was as in Example 1.
$^1$H NMR (400 MHz, DMSO-d6):δ 9.80 (s, 1H), 8.63 (s, 1H), 8.26 (s, 1H), 8.24 (s, 1H), 8.09 (s, 1H), 7.98 (s, 1H), 7.81-7.75 (m, 3H), 7.64 (d, J=7.6 Hz, 1H), 7.48 (d, J=8.8 Hz, 1H), 7.42-7.35 (m, 2H), 6.97 (d, J=8.8 Hz, 1H), 6.67-6.61 (m, 1H), 6.14 (d, J=15.6 Hz, 1H), 4.02 (q, 2H), 3.02 (d, J=6.0 Hz, 2H), 2.15 (s, 6H), 1.27 (t, 3H).
MS (ESI): m/z 561 [M+H]$^+$.

EXAMPLE 28

(E)-N-((3-((5-bromo-4-((naphthalen-2-yl)amino))pyrimidin-2-yl)amino)-4-isopropoxyphenyl)-4-(dimethylamino)-2-butenamide (CCB145385)

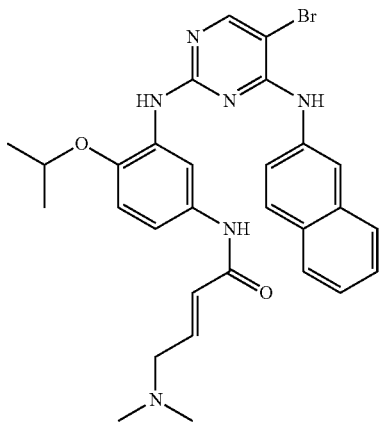

The synthetic method was as in Example 1.
$^1$H NMR (400 MHz, DMSO-d6):δ 9.79 (s, 1H), 8.66 (s, 1H), 8.27 (s, 1H), 8.25 (s, 1H), 8.03 (s, 1H), 7.98 (s, 1H), 7.81-7.76 (m, 3H), 7.65 (d, J=7.6 Hz, 1H), 7.45 (d, J=8.8 Hz, 1H), 7.43-7.35 (m, 2H), 7.00 (d, J=8.8 Hz, 1H), 6.67-6.60 (m, 1H), 6.14 (d, J=15.2 Hz, 1H), 4.51 (m, 1H), 3.01 (d, J=5.6 Hz, 2H), 2.15 (s, 6H), 1.23 (s, 3H), 1.22 (s, 3H).
MS (ESI): m/z 575 [M+H]$^+$.

EXAMPLE 29

(E)-N-((3-((5-bromo-4-((naphthalen-2-yl)amino))
pyrimidin-2-yl)amino)-5-methylphenyl)-4-(dimethylamino)-2-butenamide (CCB145342)

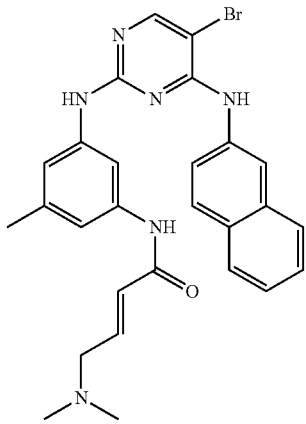

The synthetic method was as in Example 1.
¹H NMR (400 MHz, DMSO-d6): δ 9.84 (s, 1H), 9.34 (s, 1H), 8.72 (s, 1H), 8.26 (s, 2H), 7.85-7.84 (m, 2H), 7.79-7.76 (m, 2H), 7.52 (s, 1H), 7.47-7.39 (m, 2H), 7.21 (s, 1H), 7.09 (s, 1H), 6.70-6.63 (m, 1H), 6.22 (d, J=15.2 Hz, 1H), 3.02 (d, J=5.6 Hz, 2H), 2.15 (s, 6H), 1.91 (s, 3H).
MS (ESI):m/z 531 [M+H]⁺.

EXAMPLE 30

(E)-N-((5-((5-bromo-4-((naphthalen-2-yl)amino))
pyrimidin-2-yl)amino)-2-methylphenyl)-4-(dimethylamino)-2-butenamide (CCB145348)

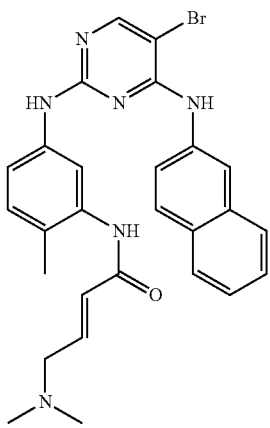 [SMILES: Cc1ccc(Nc2ncc(Br)c(Nc3ccc4ccccc4c3)n2)cc1NC(=O)/C=C/CN(C)C]

The synthetic method was as in Example 1.
¹H NMR (400 MHz, DMSO-d6): δ 9.32 (s, 2H), 8.71 (s, 1H), 8.25 (s, 2H), 7.88 (d, J=8.4 Hz, 2H), 7.80 (d, J=8.4 Hz, 2H), 7.61 (s, 1H), 7.51-7.42 (m, 3H), 6.88 (d, J=8.8 Hz, 1H), 6.70-6.63 (m, 1H), 6.31 (d, J=14.4 Hz, 1H), 3.03 (d, J=4.8 Hz, 2H), 2.17 (s, 6H), 2.09 (s, 3H).
MS (ESI):m/z 531 [M+H]⁺.

EXAMPLE 31

(E)-N-((5-((5-bromo-4-((naphthalen-2-yl)amino))
pyrimidin-2-yl)amino)-2-fluoro-4-methoxyphenyl)-
4-(dimethylamino)-2-butenamide (CCB145381)

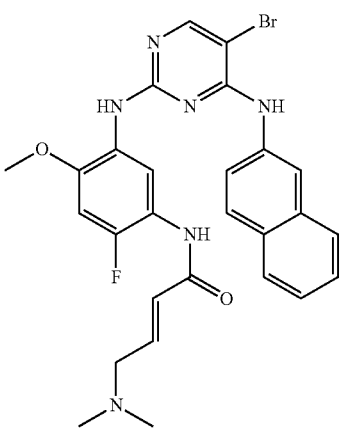

The synthetic method was as in Example 1.
¹H NMR (400 MHz, DMSO-d6): δ 9.63 (s, 1H), 8.61 (s, 1H), 8.20 (s, 2H), 8.16 (s, 1H), 8.06 (d, J=8.0 Hz, 1H), 7.80-7.75 (m, 3H), 7.69 (d, J=8.0 Hz, 1H), 7.46-7.37 (m, 2H), 7.04 (d, J=12.4 Hz, 1H), 6.68-6.61 (m, 1H), 6.30 (d, J=15.6 Hz, 1H), 3.75 (s, 3H), 3.02 (d, J=5.6 Hz, 2H), 2.16 (s, 6H).
MS (ESI):m/z 565 [M+H]⁺.

EXAMPLE 32

N-((3-((5-chloro-4-((naphthalen-2-yl)amino))pyrimidin-2-yl)amino)-4-methoxyphenyl)acrylamide (CCB120027)

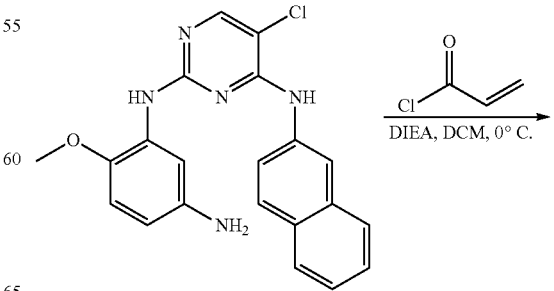

-continued

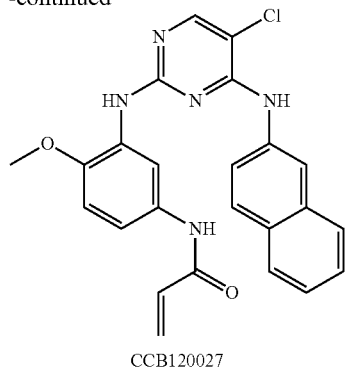

CCB120027

The synthetic method of intermediate 4 was carried out as in Example 1. The synthesis of the final product CCB120027 was as follows:

Intermediate 4 (780 mg, 2 mmol) was dissolved in dichloromethane (10 mL), and diisopropylethylamine (0.41 mL, 2.4 mmol) was added. The mixture was stirred for 5 minutes at 0° C., and acryloyl chloride (0.16 mL, 2 mmol) was added dropwise and continued to stirred for 2 h.

After it was spin dried, water (10 mL) was added. The mixture was extracted for three times with dichloromethane and dried over anhydrous Na$_2$SO$_4$. After it was spin dried, the residue was purified by column chromatography to give a solid (405 mg, yield: 45%).

$^1$H NMR (400 MHz, DMSO-d6) δ 9.94 (s, 1H), 8.89 (s, 1H), 8.28 (s, 1H), 8.15 (s, 2H), 7.99 (s, 1H), 7.83-7.78 (m, 3H), 7.68 (d, J=8.4 Hz, 1H), 7.54 (d, J=8.4 Hz, 1H), 7.41-7.37 (m, 2H), 7.01 (d, J=8.8 Hz, 1H), 6.34 (dd, J=16.8 Hz, 9.6 Hz, 1H), 6.18 (d, J=16.8 Hz, 1H), 5.67 (d, J=9.6 Hz, 1H), 3.77 (s, 3H).

MS (ESI):m/z 446 [M+H]$^+$.

EXAMPLE 33

(E)-N-((3-((5-chloro-4-((naphthalen-2-yl)amino))pyrimidin-2-yl)amino)-4-methoxyphenyl)-4-(piperidin-1-yl)-2-butenamide (CCB120024)

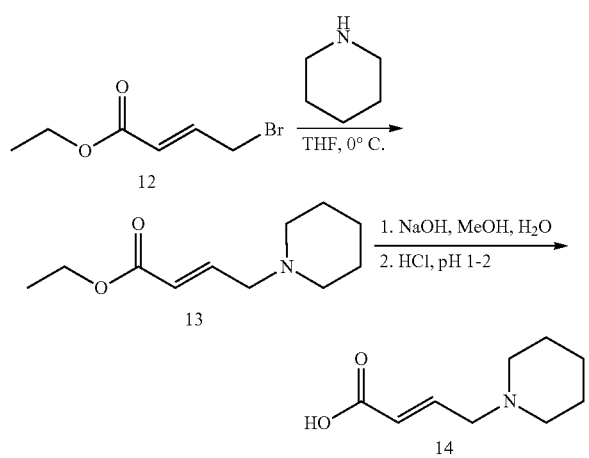

-continued

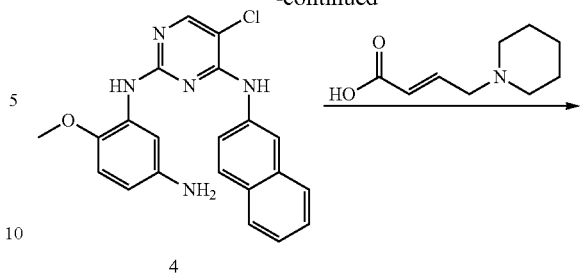

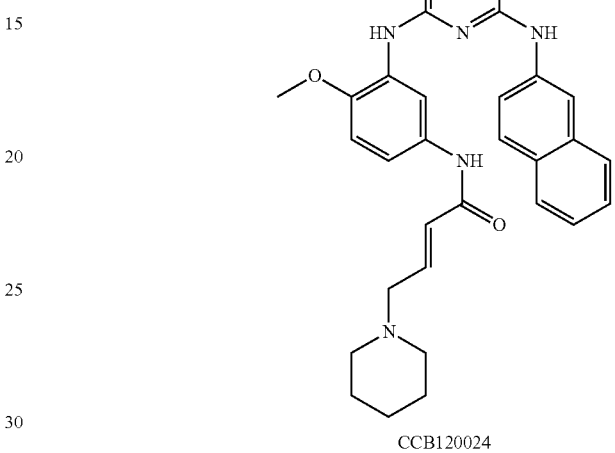

CCB120024

The synthesis of the intermediate 14 was as follows:

Step 1. (E)-4-(piperidin-1-yl)but-2-enoic acid ethyl ester (intermediate 13)

Material 12 (965 mg, 4 mmol) was dissolved in tetrahydrofuran (20 mL), and the mixture was stirred for 5 minutes at 0° C. Piperidine (1 mL, 10 mmol) was added dropwise and continued to stirred for 2 h at room temperature. After it was spin dried, the residue was dissolved in dichloromethane. The mixture was washed with saturated brine, dried over anhydrous Na$_2$SO$_4$. After it was spin dried, the residue was purified by column chromatography to give a liquid (673 mg, yield: 85%).

Step 2. (E)-4-(piperidin-1-yl)but-2-enoic acid (Intermediate 14)

10% NaOH solution (400 mg/4 mL) was added dropwise into a solution of intermediate 13 (650 mg, 3.3 mmol) in methanol (10 mL) and stirred for 1 h at 45° C. 6N HCl solution was added to adjust pH to 1-2. After it was spin dried, ethanol was added. After extraction filtration, the filtrate was spin dried. Isopropyl alcohol was added and extraction filtered again to get a solid directly used in the next step.

The synthetic method of the final product CCB120024 from intermediate 4 was carried out as step 4 in Example 1.

$^1$H NMR (400 MHz, DMSO-d6) δ 9.82 (s, 1H), 8.88 (s, 1H), 8.29 (s, 1H), 8.15 (s, 1H), 8.14 (s, 1H), 7.97 (d, J=2.4 Hz, 1H), 7.82 (dd, J=8.8 Hz, 1.6 Hz, 1H), 7.78-7.76 (m, 2H), 7.66 (d, J=8.0 Hz, 1H), 7.52 (dd, J=8.8 Hz, 2.4 Hz, 1H), 7.42-7.34 (m, 2H), 7.00 (d, J=8.8 Hz, 1H), 6.68-6.61 (m, 1H), 6.14 (d, J=15.2 Hz, 1H), 3.76 (s, 3H), 3.03 (d, J=5.6 Hz, 2H), 2.31 (br, 4H), 1.51-1.49 (br, 4H), 1.38 (br, 2H).

MS (ESI): m/z 543 [M+H]$^+$.

EXAMPLE 34

(E)-N-((3-((5-chloro-4-((naphthalen-2-yl)amino))pyrimidin-2-yl)amino)-4-methoxyphenyl)-4-(morpholin-1-yl)-2-butenamide (CCB120025)

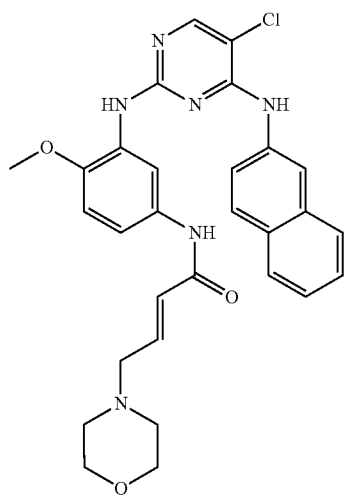 [SMILES: COc1ccc(NC(=O)/C=C/CN2CCOCC2)cc1Nc1ncc(Cl)c(Nc2ccc3ccccc3c2)n1]

The synthetic method was as in Example 33.

$^1$H NMR (400 MHz, DMSO-d6) δ 9.84 (s, 1H), 8.88 (s, 1H), 8.30 (s, 1H), 8.15 (s, 2H), 7.98 (d, J=2.4 Hz, 1H), 7.82 (dd, J=9.2 Hz, 2.0 Hz, 1H), 7.78-7.76 (m, 2H), 7.66 (d, J=7.2 Hz, 1H), 7.53 (dd, J=9.2 Hz, 2.0 Hz, 1H), 7.42-7.35 (m, 2H), 7.01 (d, J=8.8 Hz, 1H), 6.66-6.59 (m, 1H), 6.16 (d, J=15.6 Hz, 1H), 3.76 (s, 3H), 3.58 (m, 4H), 3.07 (d, J=5.6 Hz, 2H), 2.35 (br, 4H).

MS (ESI):m/z 545 [M+H]$^+$.

EXAMPLE 35

(E)-N-((3-((5-chloro-4-((naphthalen-2-yl)amino))pyrimidin-2-yl)amino)-4-methoxyphenyl)-4-(4-acetylpiperazin-1-yl)-2-butenamide (CCB120029)

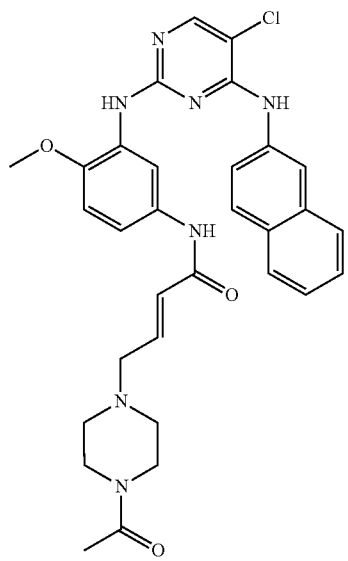 [SMILES: COc1ccc(NC(=O)/C=C/CN2CCN(C(C)=O)CC2)cc1Nc1ncc(Cl)c(Nc2ccc3ccccc3c2)n1]

The synthetic method was as in Example 33.

$^1$H NMR (400 MHz, DMSO-d6) δ 9.85 (s, 1H), 8.88 (s, 1H), 8.29 (s, 1H), 8.15 (s, 1H), 8.14 (s, 1H), 7.98 (d, J=2.0 Hz, 1H), 7.82 (dd, J=8.8 Hz, 2.0 Hz, 1H), 7.78-7.76 (m, 2H), 7.66 (d, J=7.6 Hz, 1H), 7.53 (dd, J=8.8 Hz, 2.0 Hz, 1H), 7.42-7.35 (m, 2H), 7.00 (d, J=8.8 Hz, 1H), 6.68-6.61 (m, 1H), 6.16 (d, J=15.2 Hz, 1H), 3.76 (s, 3H), 3.42 (m, 4H), 3.11 (d, J=5.6 Hz, 2H), 2.37 (m, 2H), 2.30 (m, 2H), 1.98 (s, 3H).

MS (ESI):m/z 586 [M+H]$^+$.

EXAMPLE 36

N-((3-((5-chloro-4-((naphthalen-2-yl)amino)pyrimidin-2-amino))pyrimidin-2-yl)amino)-5-morpholinemethylphenyl)acrylamide (CCB120106)

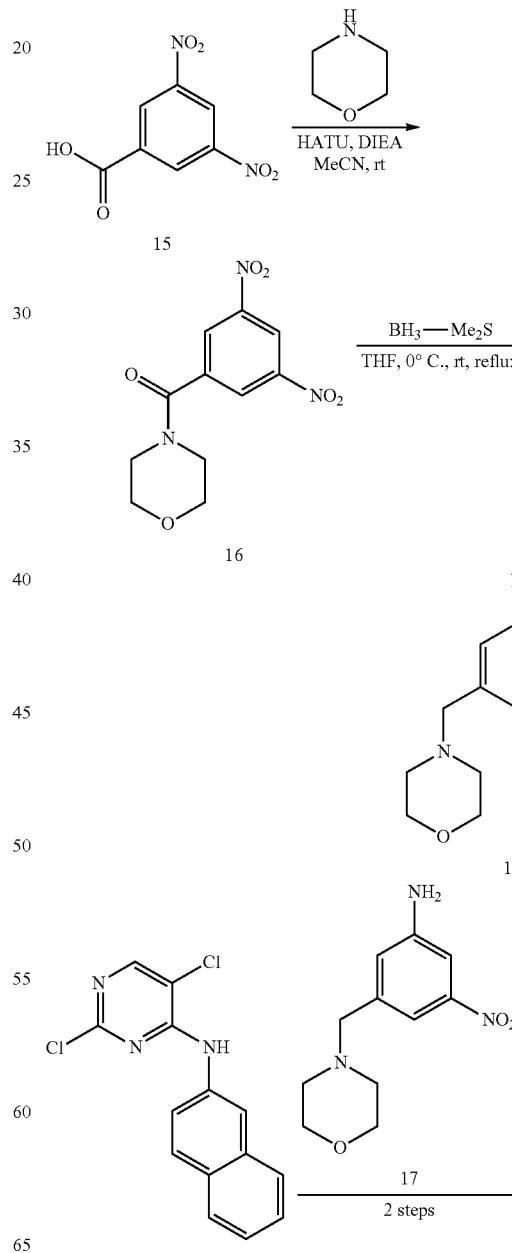

-continued

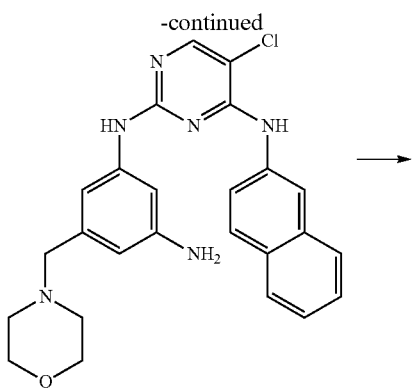

18

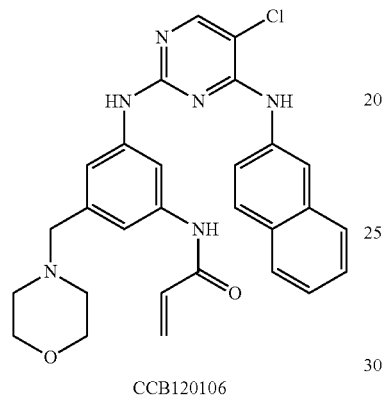

CCB120106

The synthetic method of intermediate 17 was as follows:

Step 1. (3,5-dinitrophenyl)(morpholine)methanone (Intermediate 16)

Material 15 (424 mg, 2 mmol), morpholine (0.174 mL), and 2-(7-azobenzotriazole)-N,N,N',N'-tetramethyluronium hexafluorophosphate (912 mg, 2 mmol) were dissolved in acetonitrile (10 mL). Diisopropylethylamine (1.04 mL) was added and the mixture was stirred overnight at room temperature. After it was spin dried, 10% NaHCO$_3$ solution (10 ml) was added and the mixture was extracted for three times with dichloromethane. The organic phases were combined and washed with saturated brine, dried and spin dried, and the residue was purified by column chromatography to give a solid (355 mg, yield: 63%).

Step 2. 3-(morpholinylmethyl)-5-nitroaniline (Intermediate 17)

The intermediate 16 (350 mg, 1.26 mmol) was dissolved in anhydrous THF (5 mL) and 2M BH$_3$-Me$_2$S solution (3.79 mL, 7.58 mmol) was slowly added dropwise at 0° C. The mixture was stirred for 3 h at room temperature and refluxed overnight. After natural cooled to room temperature, 6N HCl solution was added and stirred for 1 h and refluxed for 2 h at room temperature. 8N NaOH aqueous solution was added to adjust to neutral. The mixture was diluted with water, extracted for three times with ethyl acetate, saturated NaCl solution, dried, and spin dried. The residue was purified by column chromatography to give a solid (150 mg, yield: 50%).

The synthetic method of Intermediate 18 from intermediate 2 was carried out as steps 2-3 in example 1.

The synthetic method of the final product CCB120106 from intermediate 18 was carried out as example 32.

$^1$H NMR (400 MHz, DMSO-d6):δ 9.99 (s, 1H), 9.38 (s, 1H), 8.98 (s, 1H), 8.31 (s, 1H), 8.18 (s, 1H), 7.86-7.76 (m, 5H), 7.48-7.40 (m, 2H), 7.32 (s, 1H), 7.24 (s, 1H), 6.40 (dd, J=16.8 Hz, 10.0 Hz, 1H), 6.21 (dd, J=16.8 Hz, 2.0 Hz, 1H), 5.70 (dd, J=10.0 Hz, 2.0 Hz, 1H), 3.47 (m, 4H), 3.05 (s, 2H), 2.14 (s, 4H).

MS (ESI):m/z 515 [M+H]$^+$.

EXAMPLE 37

N-((3-((5-chloro-4-((naphthalen-2-yl)amino))pyrimidin-2-yl)amino)-5-(dimethylaminomethyl)phenyl)acrylamide (CCB120081)

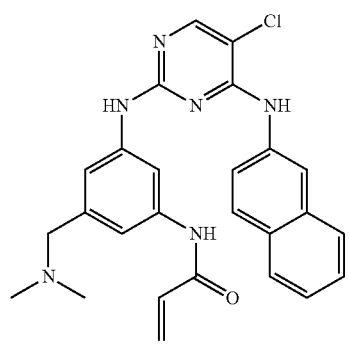 [SMILES: C=CC(=O)Nc1cc(CN(C)C)cc(Nc2ncc(Cl)c(Nc3ccc4ccccc4c3)n2)c1]

The synthetic method was as in Example 36.

$^1$H NMR (400 MHz, DMSO-d6) δ 9.98 (s, 1H), 9.38 (s, 1H), 8.97 (s, 1H), 8.32 (s, 1H), 8.19 (s, 1H), 7.86-7.78 (m, 4H), 7.74 (s, 1H), 7.48-7.40 (m, 2H), 7.31 (s, 1H), 7.25 (s, 1H), 6.40 (dd, J=16.8 Hz, 10.0 Hz, 1H), 6.20 (dd, J=16.8 Hz, 2.0 Hz, 1H), 5.69 (dd, J=10.0 Hz, 2.0 Hz, 1H), 2.99 (s, 2H), 1.98 (s, 6H).

MS (ESI): m/z 473 [M+H]$^+$.

EXAMPLE 38

N-((3-((5-chloro-4-((naphthalen-2-yl)amino))pyrimidin-2-yl)amino)-5-((N-methyl-N-dimethylaminoethyl)methylamine)phenyl)acrylamide (CCB120069)

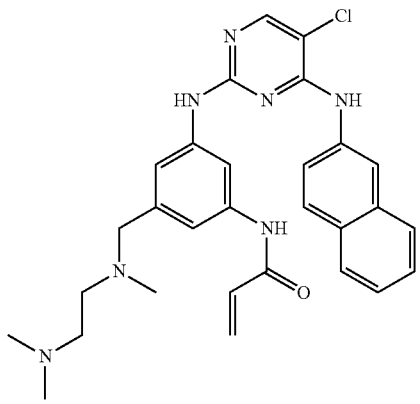 [SMILES: C=CC(=O)Nc1cc(CN(C)CCN(C)C)cc(Nc2ncc(Cl)c(Nc3ccc4ccccc4c3)n2)c1]

The synthetic method was as in Example 36.
¹H NMR (400 MHz, DMSO-d6) δ 9.99 (s, 1H), 9.38 (s, 1H), 8.96 (s, 1H), 8.33 (s, 1H), 8.18 (s, 1H), 7.85-7.80 (m, 3H), 7.78-7.77 (m, 2H), 7.47-7.39 (m, 2H), 7.32 (s, 1H), 7.23 (s, 1H), 6.41 (dd, J=16.8 Hz, 10.0 Hz, 1H), 6.21 (dd, J=16.8 Hz, 1.6 Hz, 1H), 5.69 (dd, J=10.0 Hz, 1.6 Hz, 1H), 3.07 (s, 2H), 2.23 (s, 4H), 2.06 (s, 6H), 1.96 (s, 3H).
MS (ESI): m/z 530 [M+H]⁺.

EXAMPLE 39

N-((3-((5-chloro-4-((naphthalene-2-yl)amino))pyrimidine-2-yl)amino)-5-((4-methylpiperazine-1-yl)methyl)phenyl)acrylamide (CCB120103)

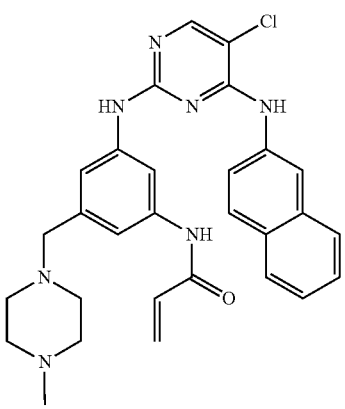 [SMILES: C=CC(=O)Nc1cc(CN2CCN(C)CC2)cc(Nc2ncc(Cl)c(Nc3ccc4ccccc4c3)n2)c1]

The synthetic method was as in Example 36.
¹H NMR (400 MHz, DMSO-d6) δ 9.98 (s, 1H), 9.38 (s, 1H), 8.97 (s, 1H), 8.32 (s, 1H), 8.18 (s, 1H), 7.85-7.83 (m, 3H), 7.79-7.77 (m, 2H), 7.47-7.40 (m, 2H), 7.29 (s, 1H), 7.22 (s, 1H), 6.40 (dd, J=16.8 Hz, 10.0 Hz, 1H), 6.20 (dd, J=16.8 Hz, 2.0 Hz, 1H), 5.70 (dd, J=10.0 Hz, 2.0 Hz, 1H), 3.06 (s, 2H), 2.19 (br, 8H), 2.11 (s, 3H).
MS (ESI): m/z 528 [M+H]⁺.

EXAMPLE 40

N-((3-((5-chloro-4-((naphthalen-2-yl)amino))pyrimidin-2-yl)amino)-5-((4-methylhomopiperazin-1-yl)methyl)phenyl)acrylamide (CCB120105)

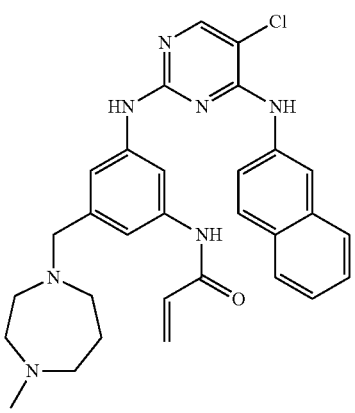 [SMILES: C=CC(=O)Nc1cc(CN2CCCN(C)CC2)cc(Nc2ncc(Cl)c(Nc3ccc4ccccc4c3)n2)c1]

The synthetic method was as in Example 36.
¹H NMR (400 MHz, Acetone-d6) δ 9.20 (br, 1H), 8.64 (br, 1H), 8.41 (s, 1H), 8.33 (br, 1H), 8.14 (s, 1H), 7.93 (s, 1H), 7.87-7.82 (m, 3H), 7.76 (d, J=8.0 Hz, 1H), 7.50-7.42 (m, 4H), 6.39 (dd, J=16.8 Hz, 10.0 Hz, 1H), 6.30 (dd, J=16.8 Hz, 2.0 Hz, 1H), 5.65 (dd, J=10.0 Hz, 2.0 Hz, 1H), 3.38 (s, 2H), 2.56-2.51 (m, 6H), 2.47-2.46 (m, 2H), 2.43 (s, 3H), 1.71-1.67 (m, 2H).
MS (ESI): m/z 542 [M+H]⁺.

EXAMPLE 41

N-((5-((5-chloro-4-((naphthalen-2-yl)amino))pyrimidin-2-yl)amino)-2-((N-methyl-N-dimethylaminoethyl)amino)-4-methoxyphenyl)acrylamide (CCB120067)

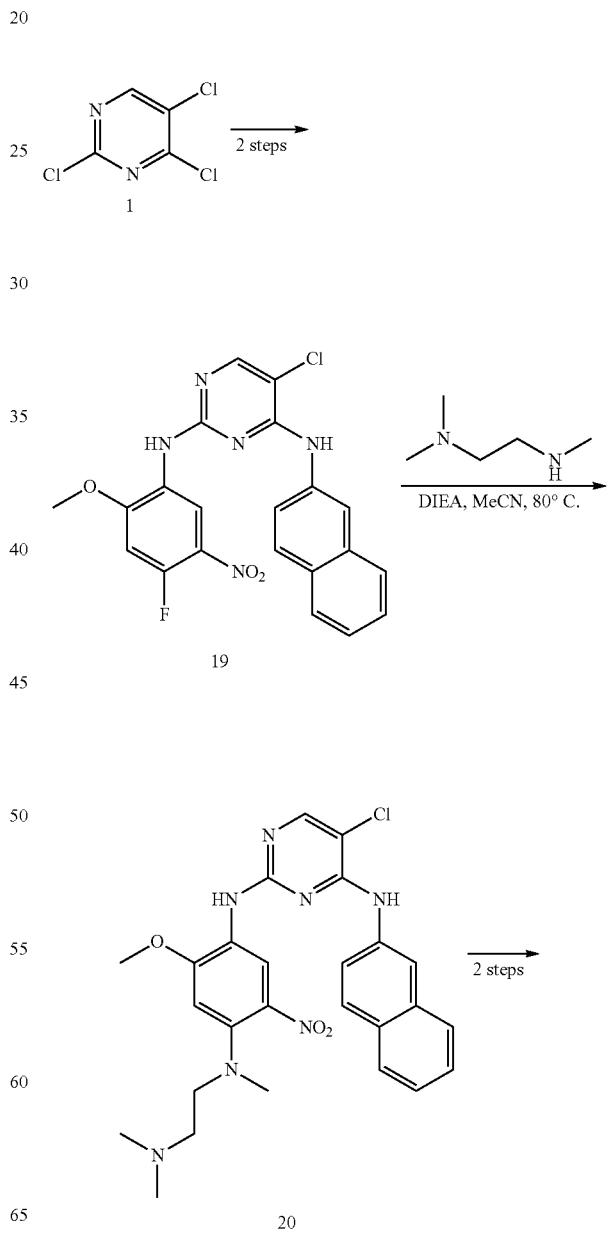

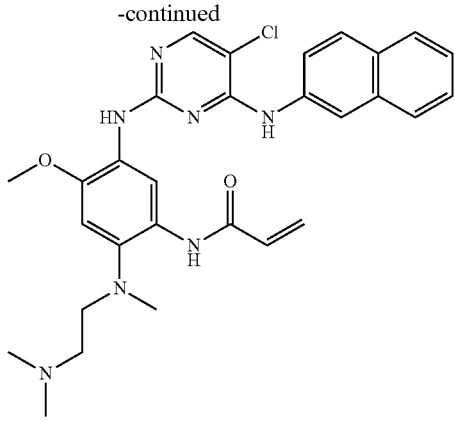

CCB120067

The synthetic method of intermediate 19 from material 1 was carried out as in steps 1-2 in Example 1.

The synthesis of intermediate 20 was as follows:

Intermediate 19 (330 mg, 0.75 mmol) was dissolved in MeCN (5 mL), and N,N-diisopropylethylamine (0.259 mL, 1.5 mmol) and trimethylethylenediamine (0.195 mL, 1.5 mmol) was added. The mixture was stirred for 2 h at 80° C. and spin dried. 10% NaHCO$_3$ solution (10 ml) was added and the mixture was extracted for three times with dichloromethane. The organic phases were combined and washed with saturated brine, dried and spin dried, and the residue was purified by column chromatography to give a solid (370 mg, yield: 95%).

The synthetic method of the final product CCB120067 from intermediate 20 was carried out as in Example 32.

$^1$H NMR (500 MHz, DMSO-d6) δ 10.02 (s, 1H), 8.80 (s, 1H), 8.46 (s, 1H), 8.26 (s, 1H), 8.23 (s, 1H), 8.11 (s, 1H), 7.81 (d, J=8.5 Hz, 1H), 7.76 (d, J=7.5 Hz, 1H), 7.72 (d, J=8.5 Hz, 1H), 7.64 (d, J=7.5 Hz, 1H), 7.42-7.35 (m, 2H), 7.00 (s, 1H), 6.34 (dd, J=17.0 Hz, 10.0 Hz, 1H), 6.14 (d, J=17.0 Hz, 1H), 5.68 (d, J=10.0 Hz, 1H), 3.75 (s, 3H), 2.88-2.86 (m, 2H), 2.72 (s, 3H), 2.31-2.29 (m, 2H), 2.19 (s, 6H).

MS (ESI): m/z 546 [M+H]$^+$.

EXAMPLE 42

N-((5-((5-chloro-4-((naphthalen-2-yl)amino))pyrimidin-2-yl)amino)-2-(4-acetylpiperazine)-4-methoxyphenyl)acrylamide (CCB120111)

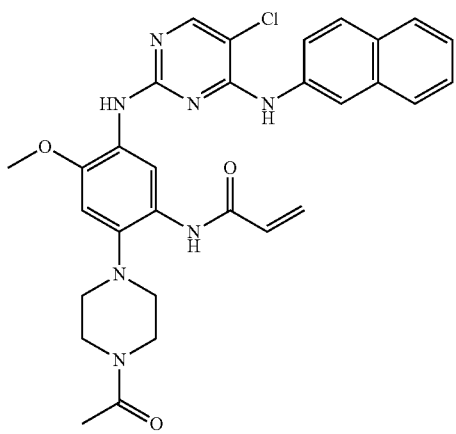 [SMILES: C=CC(=O)Nc1cc(Nc2ncc(Cl)c(Nc3ccc4ccccc4c3)n2)c(OC)cc1N1CCN(C(C)=O)CC1]

The synthetic method was as in Example 41.

$^1$H NMR (400 MHz, DMSO-d6) δ 9.03 (s, 1H), 8.81 (s, 1H), 8.25 (s, 1H), 8.23 (s, 1H), 8.22 (s, 1H), 8.11 (s, 1H), 7.81-7.74 (m, 3H), 7.62 (d, J=7.6 Hz, 1H), 7.43-7.36 (m, 2H), 6.89 (s, 1H), 6.62 (dd, J=16.8 Hz, 10.4 Hz, 1H), 6.15 (d, J=16.8 Hz, 1H), 5.68 (d, J=10.4 Hz, 1H), 3.75 (s, 3H), 3.66 (br, 4H), 2.85-2.80 (m, 4H), 2.06 (s, 3H).

MS (ESI); m/z 572 [M+H]$^+$.

EXAMPLE 43

N-((5-((5-chloro-4-((naphthalen-2-yl)amino))pyrimidin-2-yl)amino)-2-(4-methylpiperazine)-4-methoxyphenyl)acrylamide (CCB120115)

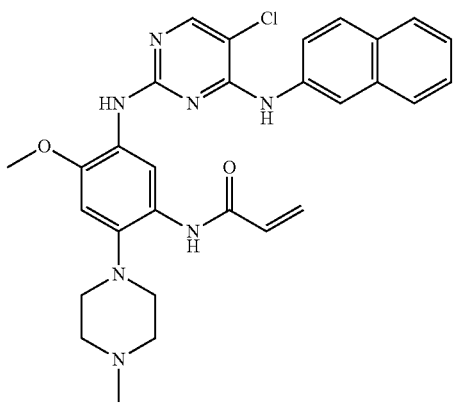 [SMILES: C=CC(=O)Nc1cc(Nc2ncc(Cl)c(Nc3ccc4ccccc4c3)n2)c(OC)cc1N1CCN(C)CC1]

The synthetic method was as in Example 41.

$^1$H NMR (400 MHz, DMSO-d6) δ 8.89 (s, 1H), 8.79 (s, 1H), 8.26 (s, 1H), 8.23 (s, 1H), 8.11 (s, 1H), 8.10 (s, 1H), 7.79-7.74 (m, 3H), 7.61 (d, J=7.2 Hz, 1H), 7.43-7.36 (m, 2H), 6.86 (s, 1H), 6.54 (dd, J=16.0 Hz, 10.0 Hz, 1H), 6.12 (d, J=16.0 Hz, 1H), 5.67 (d, J=10.0 Hz, 1H), 3.75 (s, 3H), 2.87 (s, 4H), 2.55 (s, 4H), 2.26 (s, 3H).

MS (ESI); m/z 544 [M+H]$^+$.

EXAMPLE 44

N-((5-((5-chloro-4-((naphthalen-2-yl)amino))pyrimidin-2-yl)amino)-2-morpholinyl-4-methoxyphenyl)acrylamide (CCB120117)

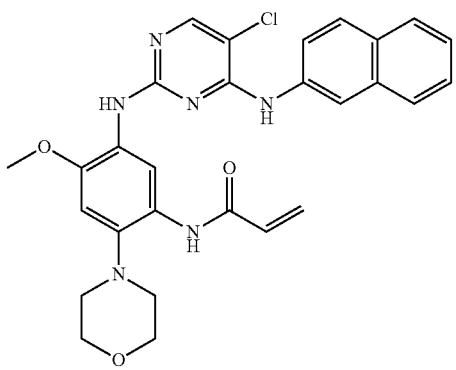 [SMILES: C=CC(=O)Nc1cc(Nc2ncc(Cl)c(Nc3ccc4ccccc4c3)n2)c(OC)cc1N1CCOCC1]

The synthetic method was as in Example 41.
¹H NMR (400 MHz, DMSO-d6) δ 9.00 (s, 1H), 8.81 (s, 1H), 8.26 (s, 1H), 8.23 (s, 1H), 8.17 (s, 1H), 8.11 (s, 1H), 7.82-7.74 (m, 3H), 7.63 (d, J=7.2 Hz, 1H), 7.43-7.36 (m, 2H), 6.88 (s, 1H), 6.59 (dd, J=16.8 Hz, 10.4 Hz, 1H), 6.14 (d, J=16.8 Hz, 1H), 5.67 (d, J=10.4 Hz, 1H), 3.81 (br, 4H), 3.76 (s, 3H), 2.87 (br, 4H).
MS (ESI); m/z 531 [M+H]⁺.

EXAMPLE 45

N-((5-((5-chloro-4-((naphthalen-2-yl)amino))pyrimidin-2-yl)amino)-2-(4-methylhomopiperazinyl)-4-methoxyphenyl)acrylamide (CCB120120)

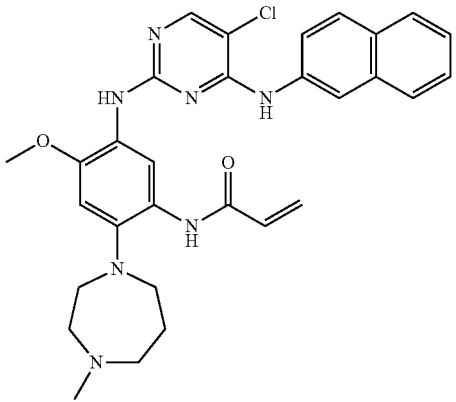 [SMILES: C=CC(=O)Nc1cc(Nc2ncc(Cl)c(Nc3ccc4ccccc4c3)n2)c(OC)cc1N1CCCN(C)CC1]

The synthetic method was as in Example 41.
¹H NMR (400 MHz, DMSO-d6) δ 9.06 (s, 1H), 8.78 (s, 1H), 8.27 (s, 1H), 8.20 (s, 1H), 8.10 (s, 1H), 7.98 (s, 1H), 7.81-7.74 (m, 3H), 7.63 (d, J=7.2 Hz, 1H), 7.43-7.36 (m, 2H), 6.85 (s, 1H), 6.51 (dd, J=16.8 Hz, 10.0 Hz, 1H), 6.13 (d, J=16.8 Hz, 1H), 5.67 (d, J=10.0 Hz, 1H), 3.74 (s, 3H), 3.16-3.14 (m, 4H), 2.69-2.67 (m, 4H), 2.33 (s, 3H), 1.89-1.86 (m, 2H).
MS (ESI): m/z 558 [M+H]⁺.

EXAMPLE 46

N-((5-((5 chloro-4-((naphthalen-2-yl)amino))pyrimidin-2-yl)amino)-2-(4-dimethylaminopiperidine)-4-methoxyphenyl)acrylamide (CCB120121)

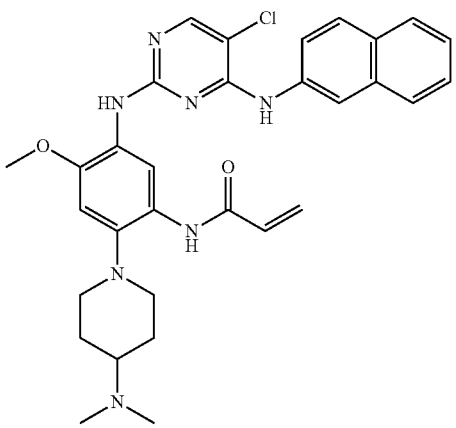 [SMILES: C=CC(=O)Nc1cc(Nc2ncc(Cl)c(Nc3ccc4ccccc4c3)n2)c(OC)cc1N1CCC(N(C)C)CC1]

The synthetic method was as in Example 41.
¹H NMR (400 MHz, DMSO-d6) δ 8.91 (s, 1H), 8.78 (s, 1H), 8.27 (s, 1H), 8.23 (s, 1H), 8.14 (s, 1H), 8.10 (s, 1H), 7.81-7.73 (m, 3H), 7.61 (d, J=7.2 Hz, 1H), 7.43-7.36 (m, 2H), 6.84 (s, 1H), 6.61 (dd, J=16.8 Hz, 10.4 Hz, 1H), 6.14 (d, J=16.8 Hz, 1H), 5.67 (d, J=10.4 Hz, 1H), 3.74 (s, 3H), 3.06-3.04 (m, 2H), 2.71-2.65 (m, 2H), 2.32 (s, 6H), 2.23-2.17 (m, 1H), 1.87-1.84 (m, 2H), 1.74-1.66 (m, 2H).
MS (ESI): m/z 572 [M+H]⁺.

EXAMPLE 47

N-((5-((5-chloro-4-((naphthalen-2-yl)amino))pyrimidin-2-yl)amino)-2-(3-dimethylaminopyrrolidin-1-yl)-4-methoxyphenyl)acrylamide (CCB120137)

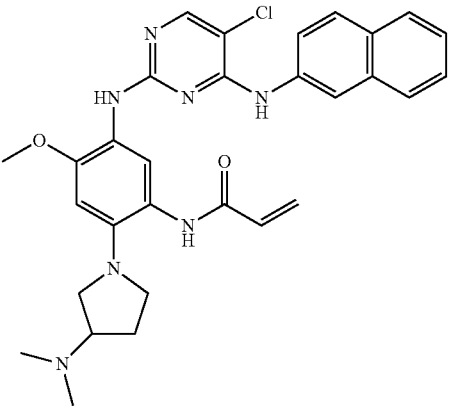 [SMILES: C=CC(=O)Nc1cc(Nc2ncc(Cl)c(Nc3ccc4ccccc4c3)n2)c(OC)cc1N1CCC(N(C)C)C1]

The synthetic method was as in Example 41.
¹H NMR (400 MHz, DMSO-d6): δ 9.26 (s, 1H), 8.73 (s, 1H), 8.29 (s, 1H), 8.14 (s, 1H), 8.07 (s, 1H), 7.82-7.76 (m, 3H), 7.65 (d, J=6.8 Hz, 1H), 7.43-7.36 (m, 3H), 6.51 (s, 1H), 6.45 (dd, J=16.8 Hz, 10.0 Hz, 1H), 6.13 (d, J=16.8 Hz, 1H), 5.64 (d, J=10.0 Hz, 1H), 3.73 (s, 3H), 3.42-3.35 (m, 1H), 3.24-3.16 (m, 3H), 2.72-2.68 (m, 1H), 2.17 (s, 6H), 2.13-2.09 (m, 1H), 1.77-1.72 (m, 1H).
MS (ESI): m/z 558 [M+H]⁺.

EXAMPLE 48

N-((5-((5-chloro-4-((naphthalen-2-yl)amino))pyrimidin-2-yl)amino)-2-(3-dimethylamino azetidin-1-yl)-4-methoxyphenyl)acrylamide (CCB120138)

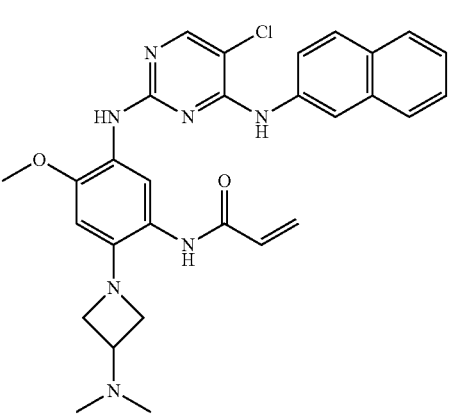 [SMILES: C=CC(=O)Nc1cc(Nc2ncc(Cl)c(Nc3ccc4ccccc4c3)n2)c(OC)cc1N1CC(N(C)C)C1]

The synthetic method was as in Example 41.

$^{1}$H NMR (400 MHz, DMSO-d6) δ 9.20 (s, 1H), 8.73 (s, 1H), 8.28 (s, 1H), 8.12 (s, 1H), 8.06 (s, 1H), 7.81-7.75 (m, 3H), 7.65 (d, J=7.6 Hz, 1H), 7.51 (t, J=7.6 Hz, 1H), 7.38 (t, J=7.6 Hz, 1H), 7.33 (s, 1H), 6.43 (dd, J=16.8 Hz, 10.4 Hz, 1H), 6.23 (s, 1H), 6.14 (d, J=16.8 Hz, 1H), 5.64 (d, J=10.4 Hz, 1H), 3.98 (t, J=7.2 Hz, 2H), 3.72 (s, 3H), 3.59 (t, J=7.2 Hz, 2H), 3.07 (m, 1H), 2.10 (s, 6H).

MS (ESI): m/z 544 [M+H]$^{+}$.

EXAMPLE 49

N-((5-((5-chloro-4-(naphthalene-2-ylamino)pyrimidine-2-yl)amino)-4-methoxy-2-(methyl(2-methylamino)ethyl)amino)phenyl)acrylamide (CCB4580030)

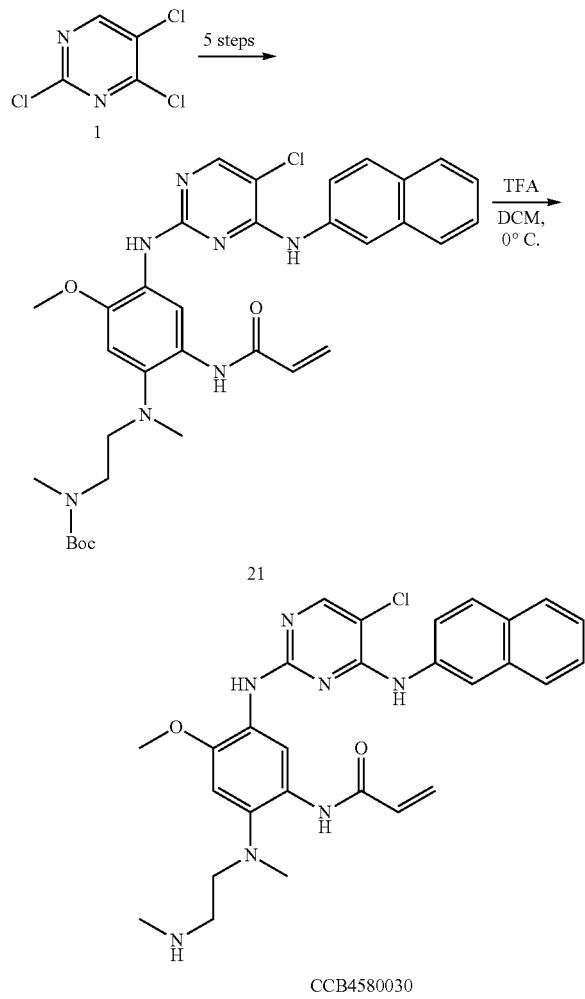

The synthetic method of intermediate 21 from material 1 was carried out as Example 41.

The synthesis of the final product CCB4580030 was as follows:

Intermediate 21 (378 mg, 0.60 mmol) was dissolved in DCM (5 mL). When it was cooled to 0° C., trifluoroacetic acid (446 μL, 6.0 mmol) was added dropwise. The mixture was warmed to room temperature, stirred for 2 h and spin dried. 10% NaHCO$_3$ solution (10 ml) was added and the mixture was extracted for three times with dichloromethane. The organic phases were combined and washed with saturated brine, dried and spin dried and the residue was purified by column chromatography to give a solid (293 mg, yield: 92%).

$^{1}$H NMR (400 MHz, DMSO-d6) δ 9.39 (s, 1H), 8.88 (s, 1H), 8.24-8.20 (m, 3H), 8.16 (s, 1H), 8.12 (s, 1H), 7.85-7.80 (m, 3H), 7.78-7.70 (m, 1H), 7.46-7.36 (m, 2H), 6.94 (s, 1H), 6.56 (dd, J=16.8 Hz, 10.4 Hz, 1H), 6.21 (d, J=16.8 Hz, 1H), 5.74 (d, J=10.4 Hz, 1H), 3.80 (s, 3H), 3.24-3.18 (m, 2H), 3.10-3.04 (m, 2H), 2.59 (s, 3H), 2.57 (s, 3H).

MS (ESI): m/z 532 [M+H]$^{+}$.

EXAMPLE 50

2-aminopyrimidine compound kinase inhibitory activity test

The enzyme substrate poly (glutamic acid, tyrosine)$_{4:1}$ (Sigma) was diluted with potassium-free PBS (10 mM sodium phosphate buffer, 150 mM NaCl, pH 7.2-7.4) to 20 μg/mL, plate coated with 125 μL/well, reacted for 12-16 hours at 37° C. After the liquid in the wells was discarded, the plates were washed three times with 200 μL/well of T-PBS (PBS containing 0.1% Tween-20), and each time for 5 minutes, and then dried for 1-2 hours in an oven at 37° C. 50 μL of ATP solution diluted with reaction buffer (50 mM HEPES pH 7.4, 50 mM MgCl$_2$, 5 mM MnCl$_2$, 0.2 mM Na$_3$VO$_4$, 1 mM DTT) was added into each well and the final concentration was 5 μM. The compounds were diluted with 1% DMSO to suitable concentrations and were added at 10 μL/well. Then different types of tyrosine kinase proteins (including EGFR$^{wt}$, EGFR$^{T790M/L858R}$ and IGF-1R, purchased from Millipore) diluted with 40 μL of reaction buffer were added. The above reaction system was reacted for 1 hour at 37° C. shaking table (100 rpm). Control wells with no enzyme and control wells with DMSO solvent were set in each experiment. After the reaction was completed, the plates were washed three times with T-PBS. The anti-phosphotyrosine primary antibody PY99 (Santa Cruz) was added at 100 μL/well and the antibody was diluted with T-PBS containing BSA 5 mg/mL by 1:1000. The mixture was reacted for 0.5 h at 37° C. shaking table, the plates were washed three times with T-PBS. The secondary antibody which was horseradish peroxidase-labeled goat anti-mouse IgG was added at 100 μL/well (the antibody was diluted with T-PBS containing BSA 5 mg/mL by 1:2000). The mixture was reacted for 0.5 h at 37° C. shaking table, the plates were washed three times with T-PBS. 2 l/mL of OPD coloring solution was added at 100 μL/well (diluted with 0.1 M citric acid-sodium citrate buffer (pH=5.4) containing 0.03% H$_2$O$_2$) and dark reacted for 1 to 10 minutes at 25° C. 2 M H$_2$SO$_4$ was added at 50 μL/well to terminate the reaction. Reading was carried out with an adjustable wavelength microplate enzyme-labeled instrument SPECTRA MAX 190 at 490 nm wavelength.

$$\text{Inhibition rate of the compound \%} = \frac{\text{Average } OD \text{ values of negative control group} - \text{Average } OD \text{ values of compound-added group}}{\text{Average } OD \text{ values of negative control group}} \times 100\%$$

The IC$_{50}$ value was calculated by the four-parameter fitting of the suppression curve. Table 1 lists the compound numbers and the results of the corresponding kinases activity.

TABLE 1 kinase inhibitory activity of compounds

| compound | IC$_{50}$ (nM) | | |
|---|---|---|---|
| | EGFR$^{WT}$ | EGFR$^{T790M/L858R}$ | IGF-1R |
| CCB118563 | 260.4 | 18.2 | 14.7 |
| CCB145213 | 615.2 | 43.5 | 37.1 |
| CCB145221 | 848.0 | 37.6 | 12.5 |
| CCB145231 | 295.4 | 30.8 | 38 |
| CCB145242 | 54.1 | 56.6 | 98.5 |
| CCB145260 | >10000 | 293.3 | 296.8 |
| CCB145268 | 225.1 | 102.1 | 182.4 |
| CCB145274 | 2068.8 | 31.3 | 41 |
| CCB145283 | 2288.2 | 150.7 | 85.2 |
| CCB145286 | 253.7 | 22.5 | 20.5 |
| CCB145287 | 130.7 | 32 | 150.5 |
| CCB145289 | 232.5 | 72.9 | 102.52 |
| CCB145291 | 10000 | 158.6 | 347.2 |
| CCB145295 | 93.9 | 47.2 | >1000 |
| CCB145293 | 173.0 | 22.6 | 193.1 |
| CCB145329 | 1400.3 | 55.7 | 198.2 |
| CCB145330 | 4145.7 | 32.4 | 146.4 |
| CCB145333 | 4750.8 | 24.2 | 169.6 |
| CCB145335 | 3892.7 | 35.7 | 90.6 |
| CCB145339 | 4482.1 | 73.2 | 48.3 |
| CCB145340 | 2219.5 | 28.7 | 116.7 |
| CCB145342 | 1876.9 | 44.2 | 127 |
| CCB145344 | 613.3 | 46.3 | 36.0 |
| CCB145346 | 1148.3 | 56.2 | 199.5 |
| CCB145348 | 470.1 | 42.5 | 156.7 |
| CCB145373 | 1459.2 | 25.6 | 162.7 |
| CCB145374 | 2825.0 | 11.3 | 86.4 |
| CCB145380 | 1060.0 | 6.7 | 194.7 |
| CCB145381 | 3543.8 | 7.5 | 102.5 |
| CCB145384 | 2682.3 | 265.8 | 272.2 |
| CCB145385 | 3617.5 | 177.1 | 315.6 |
| CCB120027 | 172.2 | 2.2 | 263.3 |
| CCB120024 | 318.5 | 1.9 | 35.4 |
| CCB120025 | 566.5 | 11.9 | 132.1 |
| CCB120029 | 695.2 | 19.1 | 99.4 |
| CCB120067 | 9.4 | 0.4 | 31.9 |
| CCB120111 | >100 | 21.5 | 19.8 |
| CCB120115 | 40.3 | 1.6 | 28.5 |
| CCB120117 | >100 | 9.4 | 18.7 |
| CCB120120 | 31.7 | 0.6 | 18.3 |
| CCB120121 | >100 | 1.3 | 13.7 |
| CCB120137 | 16.8 | 0.3 | 56.4 |
| CCB120138 | 4.3 | 0.6 | 426.1 |
| CCB120069 | 131.9 | 3.9 | 9.0 |
| CCB120081 | 170.0 | 5.1 | 85.8 |
| CCB120103 | 102.4 | 3.1 | 73.3 |
| CCB120105 | 136.6 | 1.2 | 77.3 |
| CCB120106 | >1000 | 4.1 | 137.5 |
| CCB4580030 | 3.1 | 2.2 | 7.8 |
| CO1686 | 532.7 | 10.8 | 1324.3 |
| AZD9291 | 152.6 | 7.7 | >1000 |

The result of the kinase activity test showed that, the 2-aminopyrimidine compound formed an irreversible Michael addition reaction with the protein cysteine site. Compounds of the present invention have high inhibitory activities against two EGFR kinase subtypes. Some of the compounds (for example, CCB120027, CCB120024, CCB120067, CCB120115, CCB120120, CCB120069, CCB120137) show potent kinase inhibitory activity. Compared to EGFR$^{WT}$, the compounds' inhibitory activities against EGFR$^{T790M/L858R}$ were stronger than 20-100 times, and stronger than that of the positive control compound CO1686 and AZD-9291 (EGFR inhibitors).

EXAMPLE 51

Inhibitory Effect of the Compound on the Proliferation of Human Epidermal Cancer A431 Cell Line with High Expression of Wild Type EGFR and Human Non-Small Cell Lung Cancer NCI-H1975 Cell Line with High Expression of EGFR$^{T790M/L858R}$ Cell lines: human epidermal carcinoma A431 cell line and human non-small cell lung cancer NCI-H1975 cell line was purchased from the American Standard Biology Collection Center (ATCC).

Methods: sulforhodamine B (SRB) method, which was as follows: certain number of different tumor cells in logarithmic growth phase were inoculated on 96-well culture plates. After cultured for 24 h to cell adherence, different concentrations of the test compounds of the invention were added. Each concentration was provided with three wells, and a corresponding concentration of DMSO solvent control and a cell-free zeroing well were set. After the cells were treated with the medicine for 72 h, the culture medium was discarded and 100 μL of 10% pre-cooled trichloroacetic acid solution was added to fix the cells. After placed for 1 h at 4° C., it was washed for 5 times with distilled water and dried naturally. Then 100 μL SRB (4 mg/mL) (Sigma) solution was added and stained for 15 min at room temperature. The staining solution was discarded and washed for 5 times with 1% glacial acetic acid and dried. Finally, 150 μL of 10 mM Tris solution (pH 10.5) was added and the OD value was measured at 515 nm with adjustable wavelength microplate enzyme-labeled instrument (VERSAmax™, Molecular Device Corporation, Sunnyvale, Calif., USA). The inhibition rates of the medicines on cell growth were calculated by the following formula:

Inhibition rate (%)=(OD value of control−OD value of dosing)/OD value of control×100%.

Based on the inhibitory effect of the 2-aminopyrimidine compounds on the growth of these cells, the half maximal inhibitory concentration (IC$_{50}$) values were calculated, as shown in Table 2.

TABLE 2

Cell activity of compounds

| compound | IC$_{50}$ (μM) | |
|---|---|---|
| | A431 | NCI-H1975 |
| CCB118563 | 1.127 | 0.306 |
| CCB145213 | 0.857 | 0.240 |
| CCB145221 | 0.646 | 0.170 |
| CCB145231 | 0.615 | 0.289 |
| CCB145242 | 1.035 | 0.885 |
| CCB145260 | 17.827 | 2.0413 |
| CCB145268 | 1.112 | 1.156 |
| CCB145274 | 1.220 | 0.682 |
| CCB145283 | 1.043 | 0.860 |
| CCB145286 | 1.116 | 0.416 |
| CCB145287 | 0.611 | 0.375 |
| CCB145289 | 0.839 | 1.002 |
| CCB145291 | 11.116 | 2.782 |
| CCB145295 | 1.081 | 1.177 |
| CCB145293 | 1.304 | 0.327 |
| CCB145329 | 20.524 | 1.060 |

TABLE 2-continued

Cell activity of compounds

| compound | IC$_{50}$ (μM) | |
|---|---|---|
| | A431 | NCI-H1975 |
| CCB145330 | 12.797 | 0.948 |
| CCB145333 | 6.218 | 0.632 |
| CCB145335 | 2.592 | 2.481 |
| CCB145339 | 2.188 | 0.959 |
| CCB145340 | 1.612 | 0.864 |
| CCB145342 | 0.942 | 1.265 |
| CCB145344 | 0.775 | 0.925 |
| CCB145346 | 1.042 | 0.598 |
| CCB145348 | 4.661 | 1.103 |
| CCB145373 | 6.263 | 1.179 |
| CCB145374 | 4.474 | 2.818 |
| CCB145380 | 1.673 | 0.429 |
| CCB145381 | 1.788 | 0.5083 |
| CCB145384 | 0.671 | 1.967 |
| CCB145385 | 7.583 | 5.743 |
| CCB120027 | >10 | 0.403 |
| CCB120024 | 6.926 | 0.319 |
| CCB120025 | ~10 | 0.895 |
| CCB120029 | ~10 | 1.051 |
| CCB120067 | 0.134 | 0.001-0.056 |
| CCB120111 | 1.098 | 0.051 |
| CCB120115 | 2.590 | 0.016 |
| CCB120117 | >10 | 0.272 |
| CCB120120 | 0.260 | 0.001-0.016 |
| CCB120121 | 0.324 | 0.004 |
| CCB120137 | 0.425 | 0.167 |
| CCB120138 | 0.912 | 0.164 |
| CCB120069 | 0.535 | 0.147 |
| CCB120081 | 0.037 | 0.016 |
| CCB120103 | 1.021 | 0.131 |
| CCB120105 | 0.576 | 0.151 |
| CCB120106 | 1.998 | 0.311 |
| CO1686 | 0.972 | 0.215 |

The results showed (see table 2) that the 2-aminopyrimidine compounds significantly inhibited the proliferation of NCI-H1975 cancer cells and the inhibitory activity of the compounds on A431 cells was much lower than its activity on NCI-H1975 cells, showing the selectivity of compounds. The inhibitory activity of some compounds on NCI-H1975 cells was superior to that of the positive control compound CO1686.

EXAMPLE 52

Figure 2:
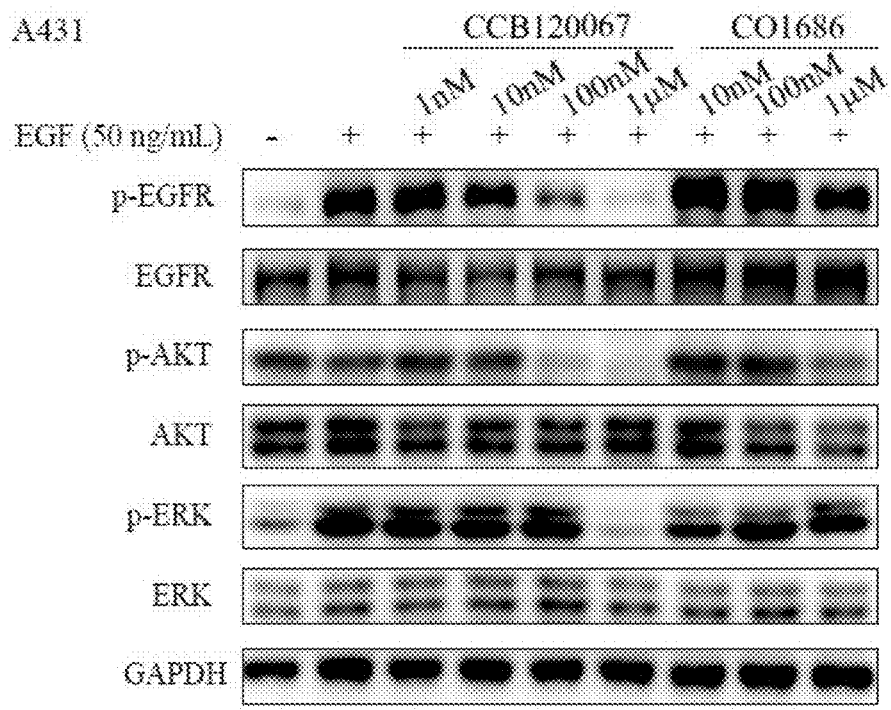
FIG. 2 shows the effect of compound CCB120067 and CO1686 on the phosphorylation of EGFR kinase and its downstream signaling pathway protein in A431 cells with wild-type EGFR high expression.

Effects of 2-Aminopyrimidine Compounds on Phosphorylation of EGFR Kinases and Activation of Downstream Signaling Pathway in NCI-H1975 Cells and A431 Cells The tests were performed using conventional Western Blot (immunoblotting test), as follows. A certain number of A431 cells and NCI-H1975 cells in the logarithmic growth phase were inoculated on 6-well plate and adherent cultured overnight in the incubator. Replaced with serum-free medium and starved for 24 h, a certain concentration of compound was added and reacted for 2 h. 50 ng/mL of EGF stimulating factor was added and reacted for 10 min. The cells were lysed with lysate and samples were collected, and then the samples were taken for SDS-PAGE electrophoresis. After electrophoresis, the protein was transferred to a nitrocellulose membrane by a semi-dry transfer system. The nitrocellulose membrane was placed in a blocking solution (5% skimmed milk diluted with TBS containing 0.1% Tween 20) for 2 h at room temperature, and then incubated overnight at 4° C. in a primary antibody solution (diluted with TBS containing 0.1% Tween 20 by 1:500). It was washed for three times with TBS containing 0.1% Tween 20 for 15 min each time. The membrane was placed in a secondary antibody solution (horseradish peroxidase labeled goat anti-rabbit IgG, diluted with TBS containing 0.1% Tween 20 by 1:2000) and reacted for 1 h at room temperature. After washed for three times as above, the membrane was dyed with ECL plus reagent and photoed using image Quant LAS 4000 camera. It can be seen from FIG. 1 that CCB120067 can significantly inhibit the phosphorylation of EGFR$^{T790M/L858R}$ and the activation of downstream signaling pathway protein AKT and ERK in NCI-H1975 cells in the 2-aminopyrimidine compounds, and the inhibitory activity is superior to that of the positive control compound CO1686. As shown in the figure, the inhibitory activity of CCB120067 at 1 nM concentration on phosphorylated EGFR$^{T790M/L858R}$ and its downstream phosphorylated Akt and Erk was comparable or slightly better than that of CO1686 at 100 nM concentration. In addition, it can be seen from FIG. 2 that the inhibitory activity of compound CCB120067 on phosphorylation of EGFR$^{wt}$ in A431 cells is weaker.

EXAMPLE 53

Inhibitory Effect of 2-Aminopyrimidine Compounds on Growth of Human Lung Cancer NCI-H1975 Nude Mice Subcutaneous Xenografts The tumor tissue in the growth stage was taken and cut into small pieces of about 1.5 mm$^3$, which were inoculated subcutaneously in nude mice under aseptic conditions. When the tumor was grown to about 100 mm$^3$, nude mice were random allocated. The dose of test compound CCB120067 was 10 mg/kg, while that of the positive control compound CO1686 was 100 mg/kg. The mice were gavage administered once a day for 11 days, and the solvent control group (injection water containing 1% Tween 80) was set. During the whole experiment, the diameter of the transplanted tumor was measured twice a week with a vernier caliper and the weights of the mice were weighed. The volume of tumor was calculated as follows:

$$TV = \tfrac{1}{2} \times a \times b^2 \text{ (Where } a,b \text{ respectively represent long and wide)}$$

Figure 3:
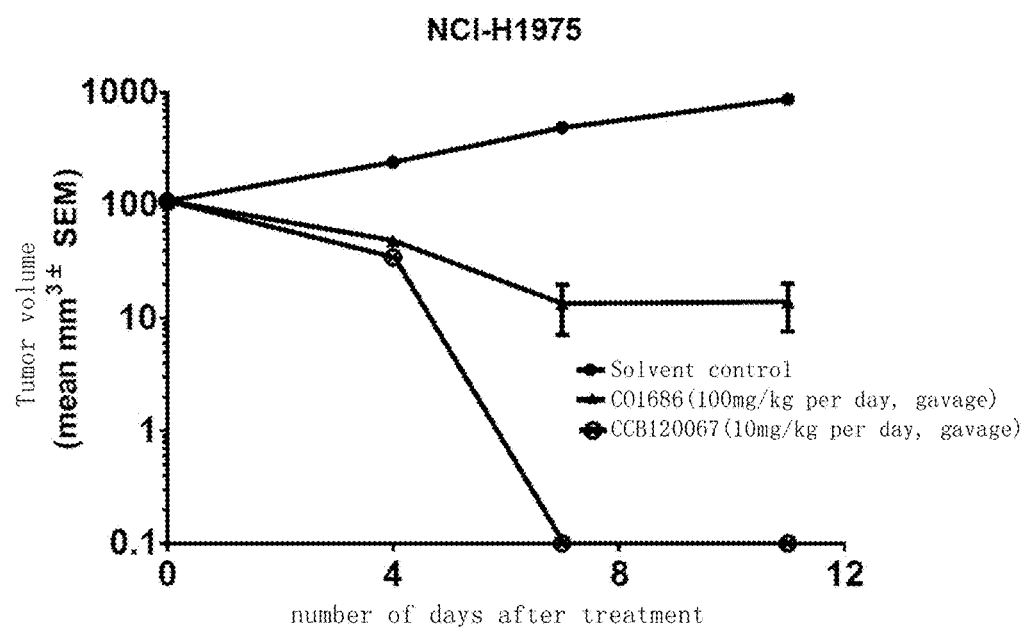
FIG. 3 shows the inhibitory effects of compounds CCB120067 and CO1686 on the growth of human lung cancer NCI-H1975 nude mice subcutaneous transplantation tumor.

The results were shown as FIG. 3. It can be seen from FIG. 3 that 10 mg/kg of CCB120067 (gavage administration) can significantly inhibit the growth of NCI-H1975 nude mice transplanted in the 2-aminopyrimidine compounds, and the tumor completely subsided after 7 days of administration. Compared to the positive control compounds, the inhibitory activity of CCB120067 at 10 mg/kg dose on the tumor growth was stronger than anti-tumor effect of CO1686 at 100 mg/kg dose.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of formula I, or a pharmaceutically acceptable salt or stereoisomer thereof:

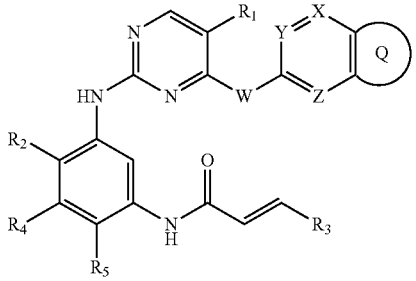

wherein $R_1$ and $R_2$ are each independently H, halogen, cyano, substituted or unsubstituted $C_1$-$C_6$ alkyl, substituted or unsubstituted $C_3$-$C_6$ cycloalkyl, substituted or unsubstituted $C_1$-$C_6$ alkoxy, and substituted or unsubstituted $C_3$-$C_6$ cycloalkoxy;

$R_3$ is H or —$(CH_2)_m NR_8R_9$; $R_4$ and $R_5$ are independently H, substituted or unsubstituted $C_1$-$C_6$ alkyl, substituted or unsubstituted $C_1$-$C_6$ alkoxy, halogen, —$(CH_2)_m NR_8R_9$, and —$(CH_2)_m CR_6R_8R_9$; wherein each m is independently 0, 1, 2 or 3; $R_6$ is H or $C_1$-$C_3$ alkyl; each $R_8$ and each $R_9$ are independently selected from H, substituted or unsubstituted $C_1$-$C_6$ alkyl, or $R_8$, $R_9$ and attached N or C together form an unsubstituted or substituted 3-8 membered monocyclic or fused ring containing 1, 2 or 3 heteroatoms selected from O, N, S;

W is NH, N($C_1$-$C_3$ alkyl), O or S;

X, Y, Z are each independently N or —$CR_{10}$, wherein $R_{10}$ is H, halogen, substituted or unsubstituted $C_1$-$C_3$ alkyl, or substituted or unsubstituted $C_1$-$C_3$ alkoxy;

is a substituted or unsubstituted 5 to 7 membered aromatic ring containing 0, 1, 2 or 3 heteroatoms selected from O, N or S;

wherein each substituted independently means substituted by substituents selected from the group consisting of: halogen, hydroxy, amino, $C_1$-$C_3$ alkyl, $C_1$-$C_3$ alkoxy, —NH($C_1$-$C_3$ alkyl), —N($C_1$-$C_3$ alkyl)($C_1$-$C_3$ alkyl), and —C(=O)($C_1$-$C_3$ alkyl).

2. The compound of claim 1, wherein,
$R_1$ and $R_2$ are each independently H, halogen, cyano, $C_1$-$C_6$ alkyl, $C_1$-$C_6$ alkoxy, $C_3$-$C_6$ cycloalkyl, $C_3$-$C_6$ cycloalkoxy, $C_1$-$C_6$ haloalkyl or $C_1$-$C_6$ haloalkoxy.

3. The compound of claim 1, wherein,

is phenyl, furanyl, thienyl, pyrrolyl, pyrazolyl, thiazolyl, isothiazolyl, oxazolyl, isoxazolyl, pyrazinyl, pyridazinyl, pyridyl, imidazolyl or pyrimidinyl.

4. The compound of claim 1, wherein the compound of formula I has one or more of the following characteristics:

(1) $R_3$ is H, —$(CH_2)_s N(C_1$-$C_3$ alkyl)($C_1$-$C_3$ alkyl), or

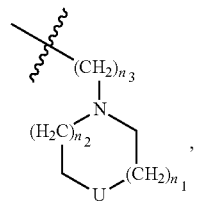

wherein s is 1 or 2 or 3;

(2) $R_4$ is H, $C_1$-$C_3$ alkyl, $C_1$-$C_3$ haloalkyl, $C_1$-$C_3$ alkoxy, $C_1$-$C_3$ haloalkoxy, halogen, —$(CH_2)_m NR_8R_9$, or

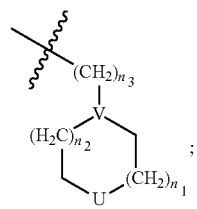

(3) $R_5$ is H, $C_1$-$C_3$ alkyl, $C_1$-$C_3$ haloalkyl, $C_1$-$C_3$ alkoxy, $C_1$-$C_3$ haloalkoxy, halogen, —$(CH_2)_m NR_8R_9$,

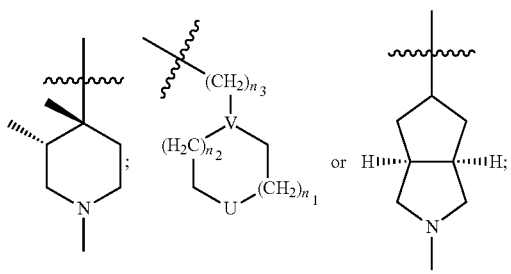

wherein each m is independently 0, 1, 2 or 3;
each $R_8$ and each $R_9$ are independently selected from H, substituted or unsubstituted $C_1$-$C_3$ alkyl, the term substituted means substituted by substituents selected from the group consisting of: halogen, —NH($C_1$-$C_3$ alkyl), —N($C_1$-$C_3$ alkyl)($C_1$-$C_3$ alkyl), and —C(=O)($C_1$-$C_3$ alkyl);
each $n_1$, each $n_2$, and each $n_3$ are independently 0, 1, 2 or 3;
each V is independently CH, C($C_1$-$C_3$ alkyl) or N;
each U is independently none, O, S, $CR_{11}R_{12}$ or $NR_{13}$, wherein $R_{11}$, $R_{12}$, $R_{13}$ are independently H, $C_1C_3$ alkyl, $C_3$-$C_6$ cycloalkyl, —NH($C_1$-$C_3$ alkyl), —N($C_1$-$C_3$ alkyl)($C_1$-$C_3$ alkyl) or —C(=O)($C_1$-$C_3$ alkyl).

5. The compound of claim 4, wherein the compound of formula I has one or more of the following characteristics:
(1) $R_3$ is H,

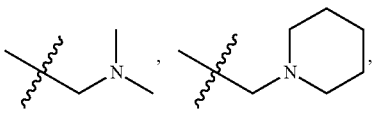

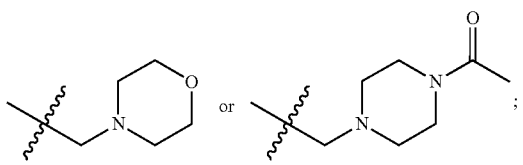

(2) R₄ is H, —CH₃,

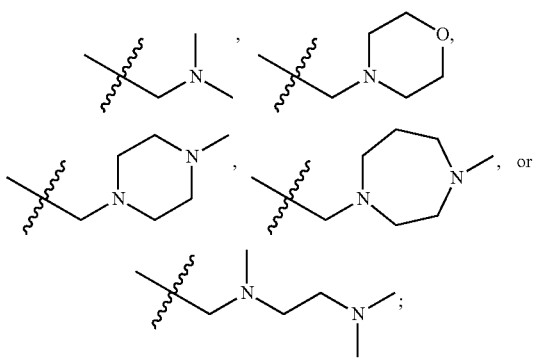

(3) R₅ is H, —CH₃, F,

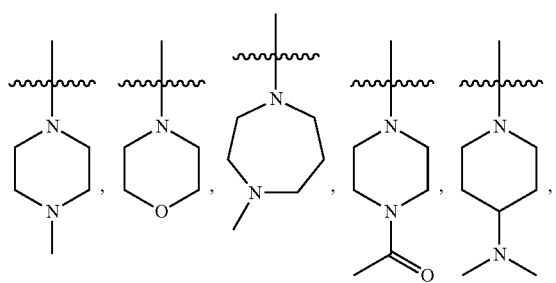

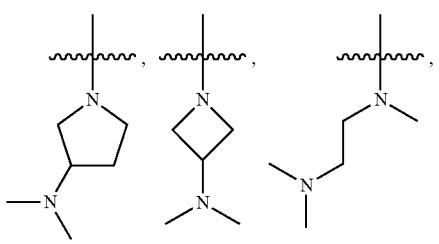

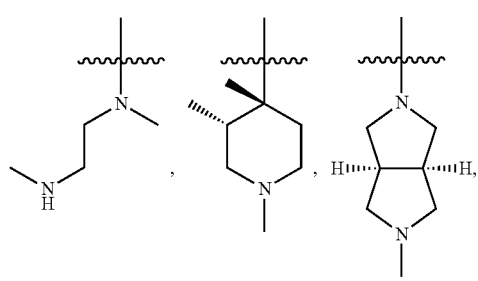

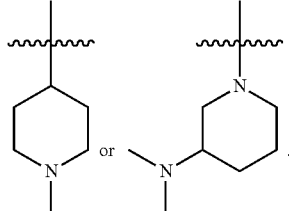

6. The compound of claim 1, wherein the compound of formula I is:
(E)-N-((3-((5-chloro-4-((naphthalen-2-yl)amino))pyrimidine-2-yl)amino)-4-methoxyphenyl)-4-(dimethylamino)-2-butenamide;
(E)-N-((3-((5-chloro-4-((quinoline-6-yl)amino))pyrimidine-2-yl)amino)-4-methoxyphenyl)-4-(dimethylamino)-2-butenamide;
(E)-N-((3-((5-chloro-4-((quinoline-3-yl)amino))pyrimidine-2-yl)amino)-4-methoxyphenyl)-4-(dimethylamino)-2-butenamide;
(E)-N-((3-((5-chloro-4-((indole-5-yl)amino))pyrimidine-2-yl)amino)-4-methoxyphenyl)-4-(dimethylamino)-2-butenamide;
(E)-N-((3-((5-chloro-4-(N-methyl-(naphthalen-2-yl)amino))pyrimidine-2-yl)amino)-4-methoxyphenyl)-4-(dimethylamino)-2-butenamide;
(E)-N-((3-((5-chloro-4-((naphthalen-2-yl)oxy))pyrimidine-2-yl)amino)-4-methoxyphenyl)-4-(dimethylamino)-2-butenamide;
(E)-N-((3-((5-chloro-4-((naphthalen-2-yl)thioro))pyrimidine-2-yl)amino)-4-methoxyphenyl)-4-(dimethylamino)-2-butenamide;
(E)-N-((3-(4-((naphthalen-2-yl)amino)pyrimidine-2-yl)amino)-4-methoxyphenyl)-4-(dimethylamino)-2-butenamide;
(E)-N-((3-((5-bromo-4-((naphthalen-2-yl)amino))pyrimidine-2-yl)amino)-4-methoxyphenyl)-4-(dimethylamino)-2-butenamide;
(E)-N-((3-((5-fluoro-4naphthalen-2-yl)amino))pyrimidine-2-yl)amino)-4-methoxyphenyl)-4-(dimethylamino)-2-butenamide;
(E)-N-((3-((5-methyl-4-((naphthalen-2-yl)amino))pyrimidine-2-yl)amino)-4-methoxyphenyl)-4-(dimethylamino)-2-butenamide;
(E)-N-((3-((5-methoxy-4-((naphthalen-2-yl)amino))pyrimidine-2-yl)amino)-4-methoxyphenyl)-4-(dimethylamino)-2-butenamide;
(E)-N-((3-((5-cyano-4-((naphthalen-2-yl)amino))pyrimidine-2-yl)amino)-4-methoxyphenyl)-4-(dimethylamino)-2-butenamide;
(E)-N-((3-((5trifluoromethyl-4-((naphthalen-2-yl)amino))pyrimidine-2-yl)amino)-4-methoxyphenyl)-4-(dimethylamino)-2-butenamide;
(E)-N-((3-((5-isopropyl-4-((naphthalen-2-yl)amino))pyrimidine-2-yl)amino)-4-methoxyphenyl)-4-(dimethylamino)-2-butenamide;
(E)-N-((3-((5-chloro-4-((naphthalen-2-yl)amino))pyrimidine-2-yl)amino)phenyl)-4-(dimethylamino)-2-butenamide;
(E)-N-((3-((5-chloro-4-((naphthalen-2-yl)amino))pyrimidine-2-yl)amino)-4-methylphenyl)-4-(dimethylamino)-2-butenamide;
(E)-N-((3-((5-chloro-4-((naphthalen-2-yl)amino))pyrimidine-2-yl)amino)-4-fluorophenyl)-4-(dimethylamino)-2-butenamide;

(E)-N-((3-((5-chloro-4-((naphthalen-2-yl)amino))pyrimidine-2-yl)amino)-4-ethoxyphenyl)-4-(dimethylamino)-2-butenamide;
(E)-N-((3-((5-chloro-4-((naphthalen-2-yl)amino))pyrimidine-2-yl)amino)-4-isopropoxyphenyl)-4dimethylamino)-2-butenamide;
(E)-N-((3-((5-chloro-4-((naphthalen-2-yl)amino))pyrimidine-2-yl)amino)-5-methylphenyl)-4-(dimethylamino)-2-butenamide;
(E)-N-((5-((5-chloro-4-((naphthalen-2-yl)amino))pyrimidine-2-yl)amino)-2-methylphenyl)-4-(dimethylamino)-2-butenamide;
(E)-N-((5-((5-chloro-4-((naphthalen-2-yl)amino))pyrimidine-2-yl)amino)-2fluoro-4-methoxyphenyl)-4-(dimethylamino)-2-butenamide;
(E)-N-((3-((5-bromo-4-((naphthalen-2-yl)amino))pyrimidine-2-yl)amino)phenyl)-4-(dimethylamino)-2-butenamide;
(E)-N-((3-((5-bromo-4-((naphthalen-2-yl)amino))pyrimidine-2-yl)amino)-4-methylphenyl)-4-(dimethylamino)-2-butenamide;
(E)-N-((3-((5-bromo-4-((naphthalen-2-yl)amino))pyrimidine-2-yl)amino)-4-fluorophenyl)-4-(dimethylamino)-2-butenamide;
(E)-N-((3-((5-bromo-4-((naphthalen-2-yl)amino))pyrimidine-2-yl)amino)-4-ethoxyphenyl)-4-(dimethylamino)-2-butenamide;
(E)-N-((3-((5-bromo-4-((naphthalen-2-yl)amino))pyrimidine-2-yl)amino)-4-isopropoxyphenyl)-4-(dimethylamino)-2-butenamide;
(E)-N-((3-((5-bromo-4-((naphthalen-2-yl)amino))pyrimidine-2-yl)amino)-5-methylphenyl)-4-(dimethylamino)-2-butenamide;
(E)-N-((5-((5-bromo-4-((naphthalen-2-yl)amino))pyrimidine-2-yl)amino)-2-methylphenyl)-4-(dimethylamino)-2-butenamide;
(E)-N-((5-((5-bromo-4-((naphthalen-2-yl)amino))pyrimidine-2-yl)amino)-2-fluoro-4-methoxyphenyl)-4-(dimethylamino)-2-butenamide;
N-((3-((5-chloro-4-((naphthalen-2-yl)amino))pyrimidine-2-yl)amino)-4-methoxyphenyl)acrylamide;
(E)-N-((3-((5-chloro-4-((naphthalen-2-yl)amino))pyrimidine-2-yl)amino)-4-methoxyphenyl)-4-(piperidine-1-yl)-2-butenamide;
(E)-N-((3-((5-chloro-4-((naphthalen-2-yl)amino))pyrimidine-2-yl)amino)-4-methoxyphenyl)-4-(morpholine-1-yl)-2-butenamide;
(E)-N-((3-((5-chloro-4naphthalen-2-yl)amino))pyrimidine-2-yl)amino)-4-methoxyphenyl)-4-(4-acetylpiperazine-1-yl)-2-butenamide;
N-((3-((5-chloro-4-((naphthalen-2-yl)amino))pyrimidine-2-yl)amino)-5-morpholine methylphenyl)acrylamide;
N-((3-((5-chloro-4-((naphthalen-2-yl)amino))pyrimidine-2-yl)amino)-5-(dimethylaminomethyl)phenyl)acrylamide;
N-((3-((5-chloro-4-((naphthalen-2-yl)amino))pyrimidine-2-yl)amino)-5-((N-methyl-N-dimethylaminoethyl)methylamine)phenyl)acrylamide;
N-((3-((5-chloro-4-((naphthalen-2yl)amino))pyrimidine-2-yl)amino)-5-((4-methylpiperazine-1-yl)methyl)phenyl)acrylamide;
N-((35chloro-4-((naphthalen-2-yl)amino))pyrimidine-2-yl)amino)-5-((4-methylhomopiperazine-1-yl)methyl)phenyl)acrylamide;
N-((5-((5-chloro-4-((naphthalen-2-yl)amino))pyrimidine-2-yl)amino)-2-((N-methyl-N-dimethylaminoethyl)amino)-4-methoxyphenyl)acrylamide;
N-((5-((5-chloro-4-((naphthalen-2-yl)amino))pyrimidine-2-yl)amino)-2-(4-acetylpiperazine)-4-methoxyphenyl)acrylamide;
N-((5-((5-chloro-4-((naphthalen-2-yl)amino))pyrimidine-2-yl)amino)-2-(4-methylpiperazine)-4-methoxyphenyl)acrylamide;
N-((5-((5-chloro-4-((naphthalen-2-yl)amino))pyrimidine-2-yl)amino)-2-morpholinyl-4-methoxyphenyl)acrylamide;
N-((5-((5-chloro-4-((naphthalen-2-yl)amino))pyrimidine-2-yl)amino)-2-(4-methylhomopiperazinyl)-4-methoxyphenyl)acrylamide;
N-((5-((5-chloro-4-((naphthalen-2-yl)amino))pyrimidine-2-yl)amino)-2-(4-dimethylaminopiperidine)-4-methoxyphenyl)acrylamide;
N-((5-((5-chloro-4-((naphthalen-2-yl)amino))pyrimidine-2-yl)amino)-2-(3-dimethylaminopyrrolidine-1-yl)-4-methoxyphenyl)acrylamide;
N-((5-((5-chloro-4-((naphthalen-2-yl)amino))pyrimidine-2-yl)amino)-2-(3-dimethylamino azetidine-1-yl)-4-methoxyphenyl)acrylamide; or N-((5-((5-chloro-4-(naphthalen-2-ylamino)pyrimidine-2-yl)amino)-4-methoxy-2-(methyl(2-methylamino)ethyl)amino)phenyl)acrylamide.

7. A method of preparing the compound of claim 1, comprising reacting a compound of formula III or a salt thereof with a compound of formula A or a salt thereof, or with a compound of formula B or a salt thereof so as to obtain a compound of formula I,

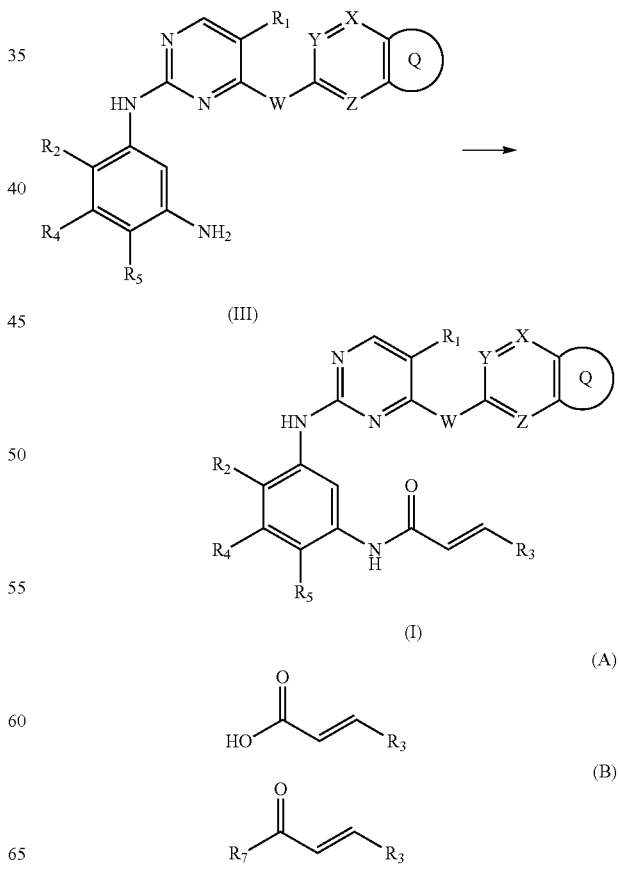

wherein $R_1$, $R_2$, $R_3$, $R_4$, $R_5$, W, X, Y and Z and

are defined as in claim 1;
$R_7$ is halogen, —OCOR$_{14}$ or OR$_{14}$, $R_{14}$ is $C_1$-$C_6$ alkyl, $C_1$-$C_6$ haloalkyl, $C_6$-$C_{10}$ aryl or $C_6$-$C_{10}$ aryl $C_1$-$C_6$ alkyl, preferably $C_1$-$C_3$ alkyl, $C_1$-$C_3$ haloalkyl, phenyl or phenyl $C_1$-$C_3$ alkyl.

8. A pharmaceutical composition comprising a compound of formula I of claim 1, or a pharmaceutically acceptable salt or stereoisomer thereof; and pharmaceutically acceptable carriers.

9. A method for inhibiting epidermal growth factor receptor (EGFR) in a subject, comprising administering to a subject having a tumor an effective amount of a compound of formula I of claim 1, or a pharmaceutically acceptable salt or stereoisomer thereof.

10. The method of claim 9, wherein the tumor is selected from the group consisting of non-small cell lung cancer, small cell lung cancer, lung adenocarcinoma, lung squamous cell carcinoma, pancreatic cancer, breast cancer, prostate cancer, liver cancer, skin cancer, epithelial cell carcinoma, gastrointestinal stromal tumor, leukemia, histiocytic lymphoma, nasopharyngeal carcinoma, head and neck cancer, colon cancer, rectal cancer, and glioma.

11. A compound of formula III or a salt thereof:

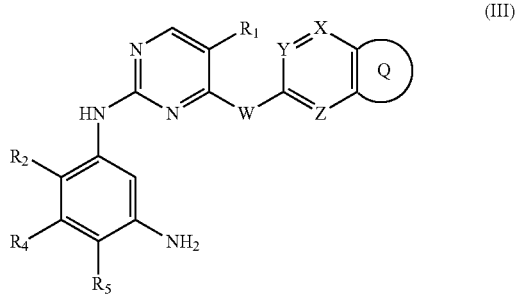

(III)

wherein $R_1$, $R_2$, $R_4$, $R_5$,

W, X, Y and Z are defined as claim 1, with the proviso that the compound of formula III does not include the following structure:

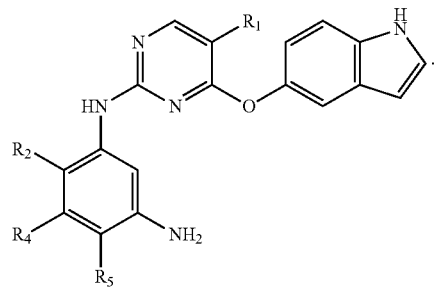

12. The method of claim 9, wherein the compound of formula I, or the pharmaceutically acceptable salt or stereoisomer thereof, is formulated in a pharmaceutical composition, which further comprises a pharmaceutically acceptable carrier.

13. The method of claim 9, wherein the subject is a human patient having tumor cells expressing the EGFR$^{T790M/L858R}$ kinase.

14. A method for treating lung cancer, comprising administering to a subject in need thereof an effective amount of a compound of formula I of claim 1, or a pharmaceutically acceptable salt or stereoisomer thereof.

15. The method of claim 14, wherein the lung cancer is non-small cell lung cancer.

* * * * *